United States Patent
Al-Awar et al.

(10) Patent No.: US 7,414,063 B2
(45) Date of Patent: Aug. 19, 2008

(54) INHIBITORS OF AKT (PROTEIN KINASE B)

(75) Inventors: Rima Salim Al-Awar, Raleigh, NC (US); David Anthony Barda, Indianapolis, IN (US); Albert Gerard Dee, Indianapolis, IN (US); Kenneth James Henry, Jr., Carmel, IN (US); Sajan Joseph, Indianapolis, IN (US); Ho-Shen Lin, Indianapolis, IN (US); Jose Eduardo Lopez, Fishers, IN (US); Michael Enrico Richett, Indianapolis, IN (US); Carmen Somoza, Alcobendas (ES)

(73) Assignee: Eli Lilly and Company, Indianapolis, IN (US)

( * ) Notice: Subject to any disclaimer, the term of this patent is extended or adjusted under 35 U.S.C. 154(b) by 86 days.

(21) Appl. No.: 10/547,969

(22) PCT Filed: Mar. 25, 2004

(86) PCT No.: PCT/US2004/006093

§ 371 (c)(1),
(2), (4) Date: Oct. 4, 2006

(87) PCT Pub. No.: WO2004/094386

PCT Pub. Date: Nov. 4, 2004

(65) Prior Publication Data

US 2007/0043040 A1    Feb. 22, 2007

Related U.S. Application Data

(60) Provisional application No. 60/458,988, filed on Mar. 28, 2003.

(51) Int. Cl.
*C07D 217/02* (2006.01)
*A61K 31/47* (2006.01)

(52) U.S. Cl. .................. 514/307; 546/139; 546/148

(58) Field of Classification Search ................ 546/139, 546/148; 514/307
See application file for complete search history.

(56) References Cited

U.S. PATENT DOCUMENTS

| | | | |
|---|---|---|---|
| 4,457,757 | A | 7/1984 | Molteno |
| 4,525,589 | A | 6/1985 | Hidaka et al. |
| 4,678,783 | A | 7/1987 | Hidaka et al. |
| 5,747,507 | A | 5/1998 | Ikegaki et al. |

FOREIGN PATENT DOCUMENTS

| | | |
|---|---|---|
| EP | 0 520 336 | 6/1992 |
| JP | 06 100540 | 4/1994 |
| WO | WO 01/64238 | 9/2001 |
| WO | WO 01/91754 | 12/2001 |
| WO | WO 02/50019 | 6/2002 |
| WO | WO 02/083064 | 10/2002 |

*Primary Examiner*—Zinna N Davis
(74) *Attorney, Agent, or Firm*—Danica Hostettler; Elizabeth A. McGraw

(57) ABSTRACT

The present invention relates to compounds Formula (I): as inhibitors of AKT activity, which are useful for the treatment of susceptible neoplasms and viral infections.

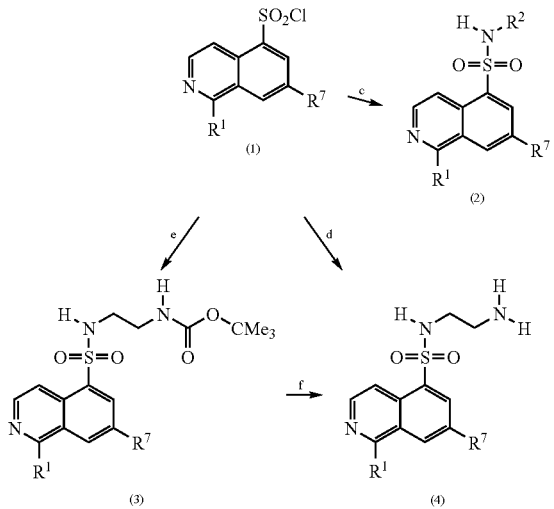

12 Claims, No Drawings

INHIBITORS OF AKT (PROTEIN KINASE B)

This application is a United States national phase entry, pursuant to 35 U.S.C. 371, of PCT/US/2004/006093, filed Mar. 25, 2004, which claims the benefit of priority under Title 35 United States Code, section 119(e), of Provisional Patent Application No. 60/458,988 filed Mar. 28, 2003; the disclosure of which is incorporated herein by reference.

The present invention provides compounds of Formula (I), compositions thereof, and a method of inhibiting Protein Kinase B (Akt) that comprises administering to a patient in need thereof an effective amount of a compound of Formula (I). In addition, the present invention relates to processes for preparing the compounds of Formula (I) and intermediates thereof.

BACKGROUND OF THE INVENTION

Protein kinases are involved in the signal transduction pathways linking growth factors, hormones and other cell regulation molecules to cell growth, survival and metabolism under both normal and pathological conditions. One such protein kinase, protein kinase B (also known as Akt), is a serine/threonine kinase that plays a central role in promoting the proliferation and survival of a wide range of cell types, thereby protecting cells from apoptosis (programmed cell death) (Khwaja, *Nature* 33-34 (1990)). Three members of the Akt/PKB subfamily of second-messenger regulated serine/threonine protein kinases have been identified and are termed Akt1/PKBα, Akt2/PKBβ, and Akt3/PKBγ. A number of proteins involved in cell proliferation and survival have been described as substrates of Akt in cells. Two examples of such substrates include glycogen synthase kinase-3 (GSK3) and Forkhead transcription factors (FKs). See Brazil and Hemmings, *Trends in Biochemical Sciences* 26, 675-664.

A number of protein kinases and phosphatases regulate the activity of Akt; For instance, activation of Akt is mediated by phosphatidylinositol 3-kinase (PI3-K), which initiates the binding of second messenger phospholipids to the pleckstrin homology (PH) binding domain of Akt. The binding anchors Akt to plasma membrane and results in phosphorylation and activation of the enzyme. Amplifications of the catalytic subunit of PI3-K, p110α, or mutations in the PI3-K regulatory subunit, p85α, lead to activation of Akt in several types of human cancer. (Vivanco and Sawyers, *Nature Reviews in Cancer* (2002) 2: 489-501.

The tumor suppressor, PTEN, is a critical negative regulator of Akt activation by PI3-K. Myers et al. *Proc. Nat. Acad. Sci.* 95, *USA* (1998) 13513-13518. Inactivating mutations in the Pten gene have been found at high frequencies in a large number of human tumors and tumor cell lines, including prostate cancer, breast cancer, ovarian cancer, glioblastoma, melanoma and other cancer types. Inactivation of the PTEN protein results in elevated levels of phosphorylated Akt and increased Akt activity in tumor cells. Li, et al., *Science* (1997) 275: 1943-1947; Guldberg, et al., *Cancer Research* (1997) 57: 3660-3663; Risinger, et al., *Cancer Research* (1997) 57: 4736-4738; Vivanco and Sawyers, *Nature Reviews in Cancer* (2002) 2: 489-501. In addition to overactivation of Akt due to defects in PTEN, direct amplication and/or overexpression of Akt2 and Akt3 have been found in human neoplasia, for example ovarian, pancreatic, prostate and breast cancer cells (Cheung et al., *Proc. Nat. Acad. Sci. USA* (1992) 89:9267-9271; Cheung et al., *Proc. Nat. Acad. Sci. USA* (1996) 93:3636-3641; Nakatani et al., J. Biol. Chem. (1999) 274: 21528-21532).

The critical role of Akt in cell proliferation and survival is further strengthened by studies showing that germline knockout of Akt1 results in partial embryonic lethality. The surviving littermates display stunted growth, increased organismal apoptosis, and early deaths. (Cho et al., *J. Biol. Chem.* (2001) 276: 38349-38520; Chen et al., *Genes Dev.* (2001) 15: 2203-2208). It has also been demonstrated that pharmacological inactivation of Akt induces apoptosis in cultured human ovarian cancer cells (Yuan et al., *Oncogene* 19, 2324-2340, 2000) and decreases growth of a human ovarian carcinoma xenograft in mice (Hu et al., *Clin. Cancer Res.* 6, 880-886, 2000).

Recent studies have also demonstrated the role of the PI3-K/AKT pathway in the life cycle of numerous viruses. Some viral proteins have been shown to directly activate the PI3-K/Akt pathway, thus providing an environment favorable for viral replication. These include the Tat protein of human immunodeficiency virus (HIV), Protein X of hepatitis B virus, and NS5A of hepatitis C virus (Borgatti et al., *Eur. J. Immunol.* (1997) 27: 2805-2811; Lee et al., *J. Biol. Ciem.* (2001) 276: 16969-16977; He et al., *J. Virol.* (2002) 76: 9207-9217). The PI3-K/Akt pathway is also required for initiation and completion of the replication cycle of human cytomegalovirus (HCMV). In fact, pharmacological inactivation of this pathway results in abortive production of HCMV and survival of the host cells (Johnson et al., *J. Virol.* (2001) 75: 6022-6032).

Because of its pivotal role in the regulation of cell survival, Akt provides a novel therapeutic target for the effective treatment of various disorders, particularly cancer and viral infections. However, such treatment requires the development of potent, selective inhibitors of Akt. Thus, the present invention provides a class of novel inhibitors of Akt, compositions comprising these compounds, and methods of using the compounds.

BRIEF SUMMARY OF THE INVENTION

The present invention provides compounds of Formula (I):

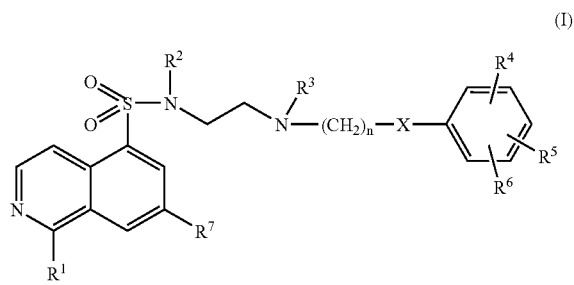

(I)

wherein:
$R^1$ is hydrogen, halo, amino or hydroxy;
$R^2$ is hydrogen, $C_1$-$C_4$ alkyl, or $C_2$-$C_4$ alkenyl,
  wherein said $C_1$-$C_4$ alkyl is optionally substituted with carboxyl, trifluoro, benzyl, acetamide, $C_1$-$C_4$ alkoxycarbonyl, substituted $C_1$-$C_4$alkoxycarbonyl, wherein the substitution is $C_1$-$C_4$ alkyl, or —$NR^9R^{10}$,
wherein $R^9$ and $R^{10}$ are each independently hydrogen or $C_1$-$C_4$ alkyl;
$R^3$ is hydrogen, or $C_1$-$C_4$ alkyl;
$R^4$ is hydrogen, halo, $C_1$-$C_4$ alkyl, or $C_1$-$C_4$alkoxy;
$R^5$ is hydrogen, halo, $C_1$-$C_4$ alkyl, $C_1$-$C_4$ alkoxy, trifluoromethyl, or nitro, or R⁴ and R⁵, together with the carbon atoms to which they are attached, form a benzo-fused ring;
R⁶ is selected from the group consisting of hydrogen, halo, C₁-C₄ alkyl, C₂-C₄ alkenyl, C₁-C₄ alkoxy, trifluoromethyl, nitro, cyano, C₃-C₆ cycloalkyl, phenyl, phenoxy, phenethyl, benzyl, benzoyl, isoxazolyl, furyl, thienyl, and methylsulfonyl;
  wherein said C₁-C₄ alkyl group may be substituted by N-morpholino, piperidine, pyrrolidine, or NR⁹R¹⁰;
  wherein said thienyl group may be substituted by halo or C₁-C₄ alkyl;
  and wherein said phenyl, benzoyl or benzyl group may be substituted with one to two substituents independently selected from the group consisting of halo, C₁-C₄ alkyl, C₁-C₄ alkoxy, CF₃, amino, nitro, hydroxy, methylsulfonylamino, sulfonamido, and C(O)R¹¹;
  wherein R¹¹ is selected from the group comprising N-morpholino, hydroxy or NR⁹R¹⁰;
X is —O—, —S(O)ₚ—, or —NR⁸—;
n is 2 or 3;
p is 0, 1, or 2;
R⁷ is hydrogen, methyl, ethynyl, phenyl, thienyl or pyrazole;
  wherein said phenyl, thienyl or pyrazole may be substituted by hydroxy, halo or amino;
R⁸ is hydrogen, C₁-C₄ alkyl, benzyl or tert-butyl ester;
or a pharmaceutically acceptable salt thereof.

Another embodiment of the invention is compounds of the formula (II):

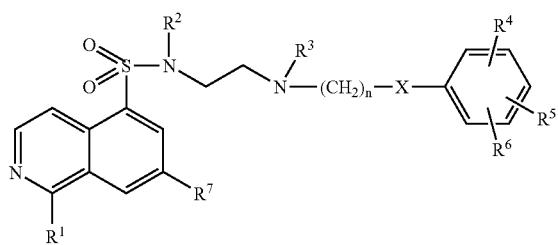

(II)

wherein:
R¹ is hydrogen, or hydroxy;
R² is hydrogen, C₁-C₄ alkyl, or C₂-C₄ alkenyl,
  wherein said C₁-C₄ alkyl is optionally substituted with carboxyl, C₁-C₄ alkoxycarbonyl, or —NR⁹R¹⁰;
  R⁹ and R¹⁰ are each independently hydrogen or C₁-C₄ alkyl;
R³ is hydrogen, or C₁-C₄ alkyl;
R⁴ is hydrogen, halo, C₁-C₄ alkyl, or C₁-C₄ alkoxy;
R⁵ is hydrogen, halo, C₁-C₄ alkyl, C₁-C₄ alkoxy, trifluoromethyl, or nitro;
  or R⁴ and R⁵, together with the carbon atoms to which they are attached, form a benzo-fused ring;
R⁶ is selected from the group consisting of hydrogen, halo, C₁-C₄ alkyl, C₂-C₄ alkenyl, C₁-C₄ alkoxy, trifluoromethyl, nitro, cyano, C₃-C₆ cycloalkyl, phenyl, phenoxy, phenethyl, benzyl, benzoyl, isoxazolyl, furyl, and thienyl;
  wherein said phenyl or benzyl groups is optionally substituted with one to two substituents independently selected from the group consisting of halo, C₁-C₄ alkyl, and C₁-C₄ alkoxy;
X is —O—, —S(O)ₚ—, or —NR⁸—;
n is 2 or 3;
p is 0, 1, or 2;
R⁷ is hydrogen or phenyl;
R⁸ is hydrogen or C₁-C₄ alkyl;
or a pharmaceutically acceptable salt thereof.

The compounds of Formula (I) are inhibitors of Akt. Because these compounds inhibit the effects of Akt activation, the compounds are useful in the treatment of disorders related to Akt activity. Thus, the compounds of Formula (I) are antiviral and antineoplastic agents.

The present compounds are believed to be useful in treating carcinomas such as neoplasms of the central nervous system: glioblastoma multiforme, astrocytoma, oligodendroglial tumors, ependymal and choroid plexus tumors, pineal tumors, neuronal tumors, medulloblastoma, schwannoma, meningioma, meningeal sarcoma; neoplasms of the eye: basal cell carcinoma, squamous cell carcinoma, melanoma, rhabdomyosarcoma, retinoblastoma; neoplasms of the endocrine glands: pituitary neoplasms, neoplasms of the thyroid, neoplasms of the adrenal cortex, neoplasms of the neuroendocrine system, neoplasms of the gastroenteropancreatic endocrine system, neoplasms of the gonads; neoplasms of the head and neck: head and neck cancer, oral cavity, pharynx, larynx, odontogenic tumors; neoplasms of the thorax: large cell lung carcinoma, small cell lung carcinoma, non-small cell lung carcinoma, neoplasms of the thorax, malignant mesothelioma, thymomas, primary germ cell tumors of the thorax; neoplasms of the alimentary canal: neoplasms of the esophagus, neoplasms of the stomach, neoplasms of the liver, neoplasms of the gallbladder, neoplasms of the exocrine pancreas, neoplasms of the small intestine, veriform appendix and peritoneum, adneocarcinoma of the colon and rectum, neoplasms of the anus; neoplasms of the genitourinary tract: renal cell carcinoma, neoplasms of the renal pelvis and ureter, neoplasms of the bladder, neoplasms of the urethra, neoplasms of the prostate, neoplasms of the penis, neoplasms of the testis; neoplasms of the female reproductive organs: neoplasms of the vulva and vagina, neoplasms of the cervix, addenocarcinoma of the uterine corpus, ovarian cancer, gynecologic sarcomas; neoplasms of the breast; neoplasms of the skin: basal cell carcinoma, squamous cell carcinoma, dermatofibrosarcoma, Merkel cell tumor; malignant melanoma; neoplasms of the bone and soft tissue: osteogenic sarcoma, malignant fibrous histiocytoma, chondrosarcoma, Ewing's sarcoma, primitive neuroectodermal tumor, angiosarcoma; neoplasms of the hematopoietic system: myelodysplastic sydromes, acute myeloid leukemia, chronic myeloid leukemia, acute lymphocytic leukemia, HTLV-1 and T-cell leukemia/lymphoma, chronic lymphocytic leukemia, hairy cell leukemia, Hodgkin's disease, non-Hodgkin's lymphomas, mast cell leukemia; and neoplasms of children: acute lymphoblastic leukemia, acute myelocytic leukemias, neuroblastoma, bone tumors, rhabdomyosarcoma, lymphomas, renal tumors.

Thus, in one embodiment, the present invention provides a method for the treatment of susceptible neoplasms comprising: administering to a patient in need thereof an effective amount of a compound of Formula (I), or a pharmaceutically acceptable salt thereof. That is, the present invention provides for the use of a compound of Formula (I), or a pharmaceutical composition thereof, for the treatment of susceptible neoplasms.

In another aspect, the present invention provides for the use of a compound of Formula (I), or a pharmaceutically acceptable salt thereof, in the manufacture of a medicament for inhibiting Akt activity. Thus, the present invention provides for the use of a compound of Formula (I), or a pharmaceutically acceptable salt thereof, in the manufacture of a medicament for the treatment of susceptible neoplasms by means of the method described above.

The compounds of the present invention are particularly useful for the treatment of neoplasms that exhibit defects in PTEN, neoplasms with deregulated PI3-Kinase activity, or neoplasms that exhibit elevated Akt activity. Specifically, the compounds of Formula (I) are useful for the treatment of neuroblastoma, melanoma, breast cancer, prostate cancer, ovarian cancer, liver cancer, lung cancer, and cancers of the digestive tract, kidney, endometrium, or thyroid.

In particular, the present compounds are believed to be useful in treating solid tumors. Thus, the compounds of the present invention are useful for the treatment of prostate cancer, ovarian cancer, and breast cancer.

In a preferred embodiment, the present invention provides a method for treating prostate cancer comprising: administering to a patient in need thereof an effective amount of a compound of Formula (I), or a pharmaceutically acceptable salt thereof.

In another preferred embodiment, the present invention provides a method for treating ovarian cancer comprising: administering to a patient in need thereof an effective amount of a compound of Formula (I), or a pharmaceutically acceptable salt thereof.

In another preferred embodiment, the present invention provides a method for treating breast cancer comprising: administering to a patient in need thereof an effective amount of a compound of Formula (I), or a pharmaceutically acceptable salt thereof.

In another embodiment, the present invention provides a method for inhibiting Akt activity comprising: administering to a patient in need thereof an effective amount of a compound of Formula (I), or a pharmaceutically acceptable salt thereof.

In another embodiment, the present invention provides a method for the treatment of viral infections comprising: administering to a patient in need thereof an effective amount of a compound of Formula (I), or a pharmaceutically acceptable salt thereof. Thus, the present invention provides for the use of a compound of Formula (I), or a pharmaceutical composition thereof, as antiviral agents.

In a further embodiment, this invention provides a pharmaceutical composition comprising, as an active ingredient, a compound of Formula (I), or a pharmaceutically acceptable salt thereof, in combination with one or more pharmaceutically acceptable carriers, diluents, or excipients.

In another embodiment, the present invention relates to a method of making a compound represented by Formula (I), and intermediates thereof.

DETAILED DESCRIPTION OF THE INVENTION

The terms and abbreviations used in the preparations and examples have their normal meanings unless otherwise designated. For example "° C." refers to degrees Celsius; "N" refers to normal or normality; "mol" refers to mole or moles; "h" refers to hour(s); "eq" refers to equivalent; "g" refers to gram or grams; "L" refers to liter or liters; "M" refers to molar or molarity; "brine" refers to a saturated aqueous sodium chloride solution; "MS" refers to mass spectrometry; "NMR" refers to nuclear magnetic resonance spectroscopy; "TLC" refers to thin layer chromatography; "ACN" refers to acetonitrile; "DMF" refers to N,N-dimethylformamide; "DMSO" refers to dimethylsulfoxide; "Et$_2$O" refers to diethyl ether; "EtOAc" refers to ethyl acetate; "MeOH" refers to methanol; "EtOH" refers to ethanol; "iPrOH" refers to isopropanol; "TEA" refers to triethylamine; "TFA" refers to trifluoroacetic acid; "THF" refers to tetrahydrofuran; "DIBAL-H" refers to diisobutylaluminum hydride.

As used herein, the term "$C_1$-$C_4$ alkyl" refers to straight or branched, monovalent, saturated aliphatic chains of 1 to 4 carbon atoms and includes, but is not limited to, methyl, ethyl, propyl, isopropyl, butyl, isobutyl, sec-butyl, and tert-butyl. The terms "$C_1$-$C_3$ alkyl" and "$C_1$-$C_2$ alkyl" are encompassed within the definition of "$C_1$-$C_4$ alkyl."

"$C_2$-$C_4$ alkenyl" refers to a straight or branched hydrocarbon chain of 2 to 4 carbon atoms with at least one carbon-carbon double bond. Examples of $C_2$-$C_4$ alkenyl groups include, but are not limited to, ethenyl (vinyl), propen-1-yl, propen-2-yl (isoprenyl), propen-3-yl (allyl), 2-methyl-propen-3-yl, 2-buten-4-yl, 2-methyl-propen-1-yl, and 1-buten-1-yl.

"$C_1$-$C_4$ alkoxy" represents a $C_1$-$C_4$ alkyl group, as defined above, linked to the parent molecule through an oxygen atom. Typical $C_1$-$C_4$ alkoxy groups include methoxy, ethoxy, propoxy, isopropoxy, butoxy, sec-butoxy, tert-butoxy, and the like. The term "$C_1$-$C_4$ alkoxy" includes within its definition the term "$C_1$-$C_3$ alkoxy" and "$C_1$-$C_2$ alkoxy."

"$C_1$-$C_4$ alkoxycarbonyl" represents a straight or branched $C_1$-$C_4$ alkoxy chain, as defined above, that is attached via the oxygen atom of the alkoxy to a carbonyl moiety. Typical $C_1$-$C_4$ alkoxycarbonyl groups include methoxycarbonyl, ethoxycarbonyl, propoxycarbonyl, isopropoxycarbonyl, butoxycarbonyl, t-butoxycarbonyl and the like. It will be understood that the $C_1$-$C_4$ alkoxycarbonyl may be substituted on the carbonyl carbon by $C_1$-$C_4$ alkyl.

"$C_3$-$C_6$ cycloalkyl" represents a saturated hydrocarbon ring structure containing from three to six carbon atoms. Typical $C_3$-$C_6$ cycloalkyl groups include cyclopropyl, cyclopentyl, cyclohexyl, and the like.

"Halo," "halogen," and "halide" represent a chloro, fluoro, bromo or iodo atom. Preferred halogens include chloro and fluoro.

As used herein, a "benzo-fused ring" refers to a bicyclic ring in which $R^4$ and $R^5$ form a ring that is ortho-fused to the phenyl ring to which they are attached. It will be understood that when $R^4$ and $R^5$ form a benzo-fused ring, $R^6$ may be a substituent on any position of the bicyclic ring that allows substitution. Preferred benzo-fused rings of the present invention include naphthalene, benzofuran, and benzodioxole.

The term "Pg" refers to an alcohol, carboxyl, or amino protecting group. Typical protecting groups include tetrahydropyranyl (THP), silanes such as trimethylsilane (TMS), tert-butyldimethylsilane (TBDMS), and tert-butyldiphenylsilane (TBDPS), methoxymethyl (MOM), benzyl (Bn), p-methoxybenzyl, formyl, acetyl (Ac), and tert-butoxycarbonyl (t-BOC). Typical carboxyl protecting groups may include methyl, ethyl, and tert-butyl. The selection and use of protecting groups is well known and appreciated in the art. See for example, *Protecting Groups in Organic Synthesis*, Theodora Greene (Wiley-Interscience); *Protecting Groups*, Philip J. Kocienski, Thieme Medical Publishers, inc: New York 1994, chapters 2, 4, 6.

This invention includes the pharmaceutically acceptable salts of the compounds of Formula (I). A compound of this invention can possess a sufficiently basic functional group, which can react with any of a number of inorganic and organic acids, to form a pharmaceutically acceptable salt.

The term "pharmaceutically-acceptable salt" as used herein, refers to a salt of a compound of the above Formula (I). It should be recognized that the particular counterion forming a part of any salt of this invention is usually not of a critical nature, so long as the salt as a whole is pharmacologically acceptable and as long as the counterion does not contribute undesired qualities to the salt as a whole.

The compounds of Formula (I) and the intermediates described herein form pharmaceutically-acceptable acid addition salts with a wide variety of organic and inorganic acids and include the physiologically-acceptable salts which are often used in pharmaceutical chemistry. Such salts are also part of this invention. A pharmaceutically-acceptable acid addition salt is formed from a pharmaceutically-acceptable acid, as is well known in the art. Such salts include the pharmaceutically acceptable salts listed in *Journal of Phar-* maceutical Science, 66, 2-19 (1977), which are known to the skilled artisan. See also, The Handbook of Pharmaceutical Salts; Properties, Selection, and Use. P. H. Stahl and C. G. Wermuth (ED.s), Verlag, Zurich (Switzerland) 2002.

Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartarate, and the like. Preferred salts of the compounds of Formula (I) include hydrochloride salts, and oxalic acid salts.

As used herein, the term "patient" refers to a mammal that is afflicted with one or more disorders associated with Akt activity. It will be understood that the most preferred patient is a human. It is also understood that this invention relates specifically to the inhibition of mammalian Akt/PKB.

It is recognized that one skilled in the art may affect the disorders associated with Akt activity by treating a patient presently afflicted with the disorders with an effective amount of the compound of Formula (I). Thus, the terms "treatment" and "treating" are intended to refer to all processes wherein there may be a slowing, interrupting, arresting, controlling, or stopping of the progression of the disorders described herein, but does not necessarily indicate a total elimination of all symptoms.

As used herein, the term "effective amount" of a compound of Formula (I) refers to an amount that is effective in treating the disorders described herein.

As with any group of pharmaceutically active compounds, some groups are preferred in their end use application.

A preferred embodiment of the invention is as follows:
$R^1$ is hydrogen or hydroxy;
$R^2$ is hydrogen, $C_1$-$C_4$ alkyl or a substituted $C_1$-$C_4$ alkyl, wherein the substitution is $NR^9R^{10}$, especially wherein $R^9$ and $R^{10}$ are methyl;
$R^3$ is hydrogen;
n is 2;
X is O or N;
$R^5$ is halo, nitro, hydroxy, $C_1$-$C_4$ alkyl and $CF_3$;
$R^6$ is halo, $C_1$-$C_4$alkyl, nitro, $CF_3$, benzoyl, ortho-phenyl, or ortho-benzyl, which phenyl or benzyl is optionally substituted with one to two substituents independently selected from the group consisting of halo, $C_1$-$C_4$ alkyl, $C_1$-$C_4$ alkoxy, nitro and sulfonamide;
$R^7$ is phenyl or hydroxyphenyl;
and the pharmaceutically acceptable salts thereof.

A more preferred embodiment of the invention is as follows:
$R^1$ is hydrogen or hydroxy;
$R^2$ is hydrogen or $C_1$-$C_4$ alkyl;
$R^3$ is hydrogen;
n is 2;
X is O;
$R^7$ is 3-hydroxyphenyl or 4-hydroxyphenyl;
and the pharmaceutically acceptable salts thereof.

The skilled artisan will appreciate that additional preferred embodiments may be selected by combining the preferred embodiments above, or by reference to the examples given herein.

The compounds of the present invention can be prepared by a variety of procedures, some of which are illustrated in the schemes and examples below. The schemes and examples should in no way be understood to be limiting in any way as to how the compounds may be made.

The skilled artisan will appreciate that the introduction of certain substituents will create asymmetry in the compounds of Formula (I). The present invention contemplates all stereoisomers, enantiomers, and mixtures of enantiomers, including racemates and diastereomers. It is preferred that the compounds of the invention containing chiral centers are single enantiomers.

It will be recognized by one of skill in the art that the individual steps in the following schemes may be varied to provide the compounds of Formula (I). The particular order of steps required to produce the compounds of Formula (I) is dependent upon the particular compound being synthesized, the starting compound, and the relative lability of the substituted moieties.

Scheme 1

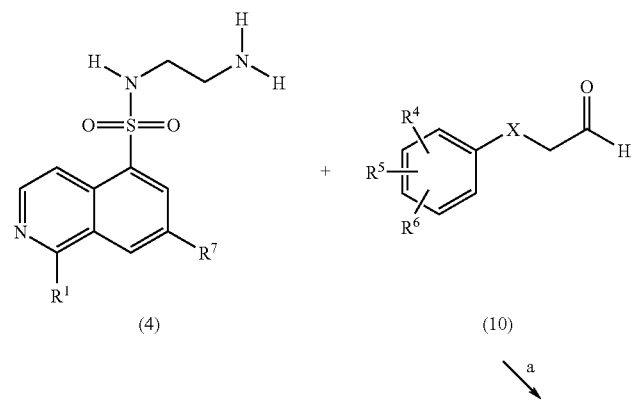

-continued

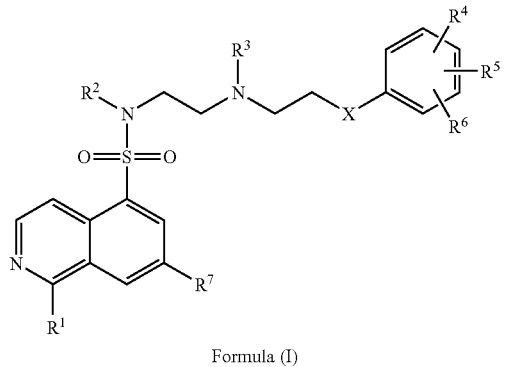

Formula (I)

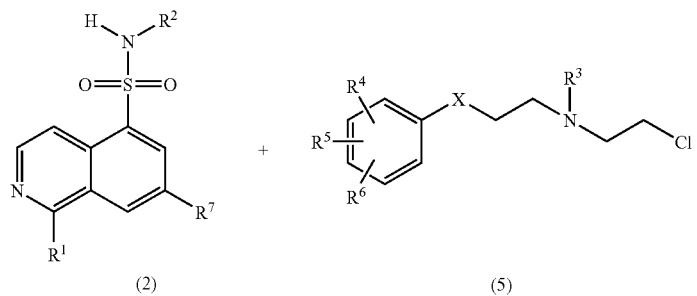

As depicted in Scheme 1, step a, a two-step procedure is used to give compounds of Formula (I) in which $R^2$ and $R^3$ are hydrogen. The compound of Formula (10) is added to a stirred mixture of 4 Å molecular sieve and the compound of Formula (4) in anhydrous $CH_3OH$, followed by stirring for 16 hours to form imines in situ. Without isolation, the imines are reduced to the corresponding desired amines by sodium borohydryde. The product of Formula (I) can be isolated and purified by techniques well known in the art, such as precipitation, filtration, extraction, evaporation, trituration, chromatography, or recrystallization.

Alternatively, as shown in step b, a compound of Formula (2) is coupled with a compound of Formula (5) to give compounds of Formula (I). The skilled artisan will appreciate that compounds of Formula (5) may be prepared by following known literature procedures. See Pharmazie, (1980) 35(2): 80-84. Thus O-alkylation of commercial phenols with methyl bromoacetate, DIBAL-H reduction, mesylate formation, ethanolamine displacement and thionyl chloride reaction give compounds of Formula (5).

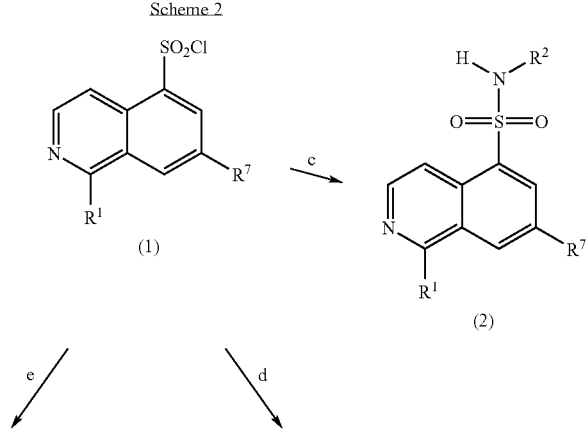

Scheme 2

-continued

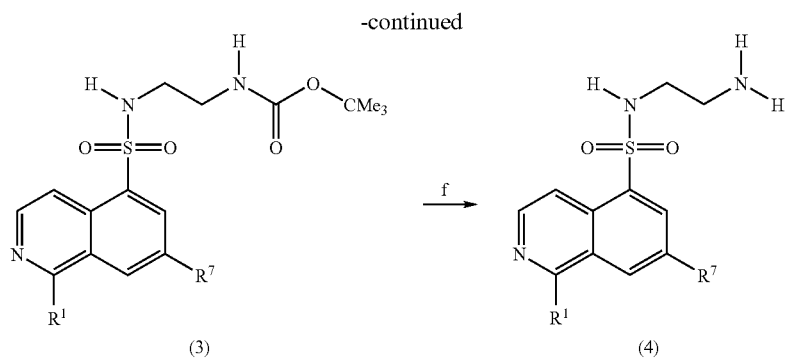

As shown in Scheme 2, step c, the compounds of Formula (2) are prepared by addition of the isoquinoline compound of Formula (1) to the appropriate alkylamine in a solvent, such as $CH_2Cl_2$. The product is isolated and purified by techniques well known to the skilled artisan, as described above.

The compounds of Formula (4) may be made directly from the isoquinoline of Formula (1), as shown in step d. The isoquinoline sulfonyl chloride of Formula (1) is added in small portions to a stirred solution of ethylenediamine in a solvent such as $CH_2Cl_2$, THF, 1,4-dioxane, or preferably, $CHCl_3$. The mixture is filtered, dried, and chromatographed by methods well known to the skilled artisan to give the compound of Formula (4).

Alternatively, the compound of Formula (1) may be added to a solution of (2-amino-ethyl)-carbamic acid tert-butyl ester and TEA, pyridine, or N,N-diisopropylethylamine in anhydrous $CH_2Cl_2$ under $N_2$. The mixture is stirred at ambient temperature for about 4 hours. The mixture is filtered, dried, and chromatographed by methods well-known to the skilled artisan to give the compound of Formula (3).

The compound of Formula (3) is de-protected by methods well known to the skilled artisan, as depicted in Step f.

Scheme 3

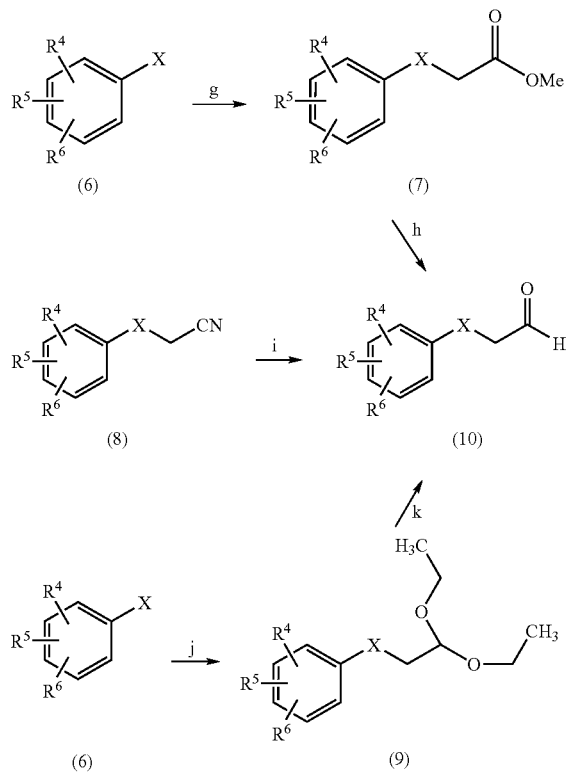

Compounds of Formula (10) may be prepared by a variety of routes, as depicted in Scheme 3. A brief description of each route is given below.

In step g, potassium carbonate is added to a solution of Formula (6) and methyl bromoacetate in a solvent such as acetonitrile, or preferably DMF. The mixture is extracted by standard techniques, for example with ethyl acetate/water or with xylene. The product is dried, filtered, concentrated, and chromatographed by techniques well known in the art.

The skilled artisan will recognize that when $R^6$ is a suitable leaving group, such as bromo, the substituent may be transformed to other $R^6$ groups, such as phenyl, isoxazolyl, furyl, or thienyl by Suzuki coupling methodology.

In step h, DIBAL-H is added dropwise to a solution of the compound of Formula (7) in a solvent, preferably $CH_2Cl_2$, at $-78°$ C. under $N_2$. The solution is stirred, followed by addition of methanol and diethyl ether. The cold bath is removed, and a HCl solution is added in small portions. The organic layer is separated, dried, filtered and concentrated to give the compound of Formula (10) and its methyl hemiacetal.

Alternatively, as shown in step i, DIBAL-H is added dropwise to a stirred solution of the compound of Formula (8) in anhydrous $CH_2Cl_2$, preferably at $-78°$ C., under $N_2$. The solution is then stirred at $0°$ C. for 1-2 hours. The reaction is quenched with addition of MeOH, followed by successive additions of diethyl ether and HCl in small portions. The organic layer is separated, dried, filtered and concentrated by techniques well known to the skilled artisan.

Compounds of Formula (6) may also be transformed to compounds of Formula (10) via the diethoxy compound of Formula (9). Briefly, as shown in step j, potassium carbonate is added to a solution of the compound of Formula (6) and bromoacetaldehyde diethyl acetal in a solvent such as DMF. The mixture is stirred at $85°$ C. under $N_2$ for about 72 hours. The mixture is cooled to ambient temperature, followed by addition of water and EtOAc. The compound of Formula (9) is separated, dried, filtered, and concentrated by techniques well known to the skilled artisan.

As depicted in step k, to a stirred solution of the compound of Formula (9) in diethyl ether is added HCl. The solution is stirred vigorously, with subsequent addition of diethyl ether in order to drive the reaction. The reaction of step k gives the product of Formula (10) and its ethyl hemiacetal.

Similarly, by use of the appropriate starting materials, as would be known by those skilled in the art, compounds wherein $R^6$ is an amine or amide may also be prepared.

PREPARATIONS

Preparation 1

Isoquinoline-5-sulfonyl chloride hydrochloride

Anhydrous DMF (1.5 mL) is added dropwise to a stirred suspension of isoquinoline-5-sulfonic acid (28.3 g, 135 mmol) in thionyl chloride (150 mL, 2.06 mole) at ambient temperature under nitrogen. The resultant mixture is heated to reflux for 2.5 hours. After being cooled to ambient temperature, the mixture is concentrated under vacuum to give a yellowish powder. The powder is suspended in dry $CH_2Cl_2$ (200 mL), sonicated, filtered and dried at 40° C. under vacuum to give 29.2 g (111 mmol, 82% yield) of the title compound. $^1$H NMR (TFA-$d_1$): δ8.48 (t, J=7.9 Hz, 1H), 9.13-9.14 (m, 2H), 9.29 (d, J=7.9 Hz, 1H), 9.57 (d, J=7.0 Hz, 1H), 10.26 (s, 1H).

Preparation 2

Isoquinoline-5-sulfonic acid (2-amino-ethyl)-amide

Powdered isoquinoline-5-sulfonyl chloride-hydrochloride (5.57 g, 21.1 mmol) is added in small portions to a stirred solution of ethylenediamine (45.0 mL, 673 mmol) in $CHCl_3$ (400 mL) at ambient temperature under nitrogen. The resultant mixture is stirred for 1 hour. After filtration and concentration in vacuo, the crude product is chromatographed on silica (gradient 5-10% $CH_3OH$ in $CH_2Cl_2$, then 0-16% 2M $NH_3/CH_3OH$ in $CH_2Cl_2$) to give 4.71 g (18.7 mmol, 89% yield) of the title compound. ESIMS: m/z 252 (M+H)$^+$.

Preparation 3

(2-bromo-phenoxy)-acetic acid methyl ester

Powdered potassium carbonate (3.84 g, 27.8 mmol) is added to a stirred solution of 2-bromophenol (3.20 g, 18.5 mmol) and methyl bromoacetate (3.11 g, 20.3 mmol) in anhydrous DMF (20 mL). The resultant mixture is stirred at ambient temperature under nitrogen for 16 hours. Water (140 mL) and EtOAc (120 mL) are added to the mixture and the two-layered solution is stirred vigorously for 3 minutes. The organic layer is separated, dried over $MgSO_4$, filtered and concentrated. The crude product is chromatographed oh silica (gradient 2-8% EtOAc in hexane) to give 4.39 g (17.9 mmol, 97% yield) of the title compound. EIMS: m/z 244 (M$^+$, $^{79}$Br), 246 (M$^+$, $^{81}$Br).

Using a procedure similar to Preparation 3, with the appropriate starting materials, the following compounds may be prepared and isolated.

| Prep. # | Compound | Data |
|---|---|---|
| 4 | (2-chloro-phenoxy)-acetic acid methyl ester | EIMS: m/z 200(M$^+$, $^{35}$Cl), 202(M$^+$, $^{37}$Cl). |
| 5 | (2-methyl-phenoxy)-acetic acid methyl ester | EIMS: m/z 180(M$^+$). |
| 6 | (2-trifluoromethyl-phenoxy)-acetic acid methyl ester | EIMS: m/z 234(M$^+$). |
| 7 | (2-tert-butyl-phenoxy)-acetic acid methyl ester | EIMS: m/z 222(M$^+$). |
| 8 | [2-(2-methyl-allyl)-phenoxy]-acetic acid methyl ester | ESIMS: m/z 221(M+H)$^+$ |
| 9 | (biphenyl-2-yloxy)-acetic acid methyl ester | EIMS: m/z 242(M$^+$). |
| 10 | (2-benzyl-phenoxy)-acetic acid methyl ester | EIMS: m/z. 256(M$^+$). Analysis for $C_{16}H_{16}O_3$: calcd: C, 74.98; H, 6.29; found: C, 75.25; H, 6.40.. |
| 11 | [2-(4-methyl-benzyl)-phenoxy]-acetic acid methyl ester | EIMS: m/z. 270(M$^+$). Analysis for $C_{17}H_{18}O_3$: calcd: C, 75.53; H, 6.71; found: C, 75.18; H, 6.65. |
| 12 | [2-(4-methoxy-benzyl)-phenoxy]-acetic acid methyl ester | EIMS: m/z. 286(M$^+$). |
| 13 | (2-phenethyl-phenoxy)-acetic acid methyl ester | EIMS: m/z. 270(M$^+$). |
| 14 | (2-methoxy-phenoxy)-acetic acid methyl ester | EIMS: m/z 196(M$^+$). |
| 15 | (2-phenoxy-phenoxy)-acetic acid methyl ester | EIMS: m/z 258(M$^+$). |
| 16 | (3-chloro-phenoxy)-acetic acid methyl ester | EIMS: m/z 200(M$^+$, $^{35}$Cl), 202(M$^+$, $^{37}$Cl). |
| 17 | (3-bromo-phenoxy)-acetic acid methyl ester | EIMS: m/z 244(M$^+$, $^{79}$Br), 246(M$^+$, $^{81}$Br). |
| 18 | (3-methyl-phenoxy)-acetic acid methyl ester | EIMS: m/z 180(M$^+$). |
| 19 | (3-trifluoromethyl-phenoxy)-acetic acid methyl ester | EIMS: m/z 234(M$^+$). |
| 20 | (biphenyl-3-yloxy)-acetic acid methyl ester | EIMS: m/z 242(M$^+$). |
| 21 | (3-benzyl-phenoxy)-acetic acid methyl ester | EIMS: m/z 256(M$^+$). |
| 22 | (3-methoxy-phenoxy)-acetic acid methyl ester | EIMS: m/z 196(M$^+$). |
| 23 | (4-fluoro-phenoxy)-acetic acid methyl ester | EIMS: m/z 184(M$^+$). |
| 24 | (4-bromo-phenoxy)-acetic acid methyl ester | EIMS: m/z 244(M$^+$, $^{79}$Br), 246(M$^+$, $^{81}$Br). |

-continued

| Prep. # | Compound | Data |
|---|---|---|
| 25 | (4-iodo-phenoxy)-acetic acid methyl ester | EIMS: m/z 292(M$^+$). |
| 26 | (4-methyl-phenoxy)-acetic acid methyl ester. | EIMS: m/z 180(M$^+$). |
| 27 | (4-trifluoromethyl-phenoxy)-acetic acid methyl ester | EIMS: m/z 234(M$^+$). |
| 28 | (biphenyl-4-yloxy)-acetic acid methyl ester | EIMS: m/z 242(M$^+$). |
| 29 | (4-benzyl-phenoxy)-acetic acid methyl ester | EIMS: m/z 256(M$^+$). |
| 30 | (4-nitro-phenoxy)-acetic acid methyl ester | EIMS: m/z 211(M$^+$). |
| 31 | (4-methoxy-phenoxy)-acetic acid methyl ester | EIMS: m/z 196(M$^+$). |
| 32 | (4-phenoxy-phenoxy)-acetic acid methyl ester | EIMS: m/z 258(M$^+$). Analysis for $C_{15}H_{14}O_4$: calcd: C, 69.76; H, 5.46; found: C, 69.76; H, 5.42. |
| 33 | (2,4-dichloro-phenoxy)-acetic acid methyl ester | EIMS: m/z 234(M$^+$, $^{35}$Cl, $^{35}$Cl), 236(M$^+$, $^{35}$Cl, $^{37}$Cl), 238(M$^+$, $^{37}$Cl, $^{37}$Cl). Analysis for $C_9H_8Cl_2O_3$: calcd: C, 45.99; H, 3.43; found: C, 45.77; H, 3.21. |
| 34 | (2-bromo-4-chloro-phenoxy)-acetic acid methyl ester | EIMS: m/z 278(M$^+$, $^{79}$Br, $^{35}$Cl), 280(M$^+$, $^{81}$Br, $^{35}$Cl or $^{79}$Br, $^{37}$Cl), 282(M$^+$, $^{81}$Br, $^{37}$Cl). Analysis for $C_9H_8BrClO_3$: calcd: C, 38.67; H, 2.88; found: C, 38.52; H, 2.49. |
| 35 | (4-Chloro-2-methyl-phenoxy)-acetic acid methyl ester | EIMS: m/z 214(M$^+$, $^{35}$Cl), 216(M$^+$, $^{37}$Cl). |
| 36 | (2-allyl-4-chloro-phenoxy)-acetic acid methyl ester | EIMS: m/z 240(M$^+$, $^{35}$Cl), 242(M$^+$, $^{37}$Cl). |
| 37 | (4-chloro-2-cyclohexyl-phenoxy)-acetic acid methyl ester | EIMS: m/z 282(M$^+$, $^{35}$Cl), 284(M$^+$, $^{37}$Cl). |
| 38 | (2-benzyl-4-chloro-phenoxy)-acetic acid methyl ester | EIMS: m/z 290(M$^+$, $^{35}$Cl), 292(M$^+$, $^{37}$Cl). |
| 39 | [2-(4-chloro-benzyl)-4-chloro-phenoxy]-acetic acid methyl ester | EIMS: m/z 324(M$^+$, $^{35}$Cl, $^{35}$Cl), 326(M$^+$, $^{35}$Cl, $^{37}$Cl), 328(M$^+$, $^{37}$Cl, $^{37}$Cl). |
| 40 | [4-chloro-2-(2,4-dichloro-benzyl)-phenoxy]-acetic acid methyl ester | EIMS: m/z 358(M$^+$, $^{35}$Cl, $^{35}$Cl, $^{35}$Cl), 360(M$^+$, $^{35}$Cl, $^{35}$Cl, $^{37}$Cl), 362(M$^+$, $^{35}$Cl, $^{37}$Cl, $^{37}$Cl). |
| 41 | (4-chloro-2-isoxazol-5-yl-phenoxy)-acetic acid methyl ester | ESIMS: m/z 268[(M+H)$^+$, $^{35}$Cl], 270[(M+H)$^+$, $^{37}$Cl]. |
| 42 | (4-chloro-2-methoxy-phenoxy)-acetic acid methyl ester | EIMS: m/z 230(M$^+$, $^{35}$Cl), 232(M$^+$, $^{37}$Cl). Analysis for $C_{10}H_{11}ClO_4$: calcd: C, 52.08; H, 4.81; found: C, 51.76; H, 4.74. |
| 43 | (3,4-dichloro-phenoxy)-acetic acid methyl ester | EIMS: m/z 234(M$^+$, $^{35}$Cl, $^{35}$Cl), 236(M$^+$, $^{35}$Cl, $^{37}$Cl), 238(M$^+$, $^{37}$Cl, $^{37}$Cl). |
| 44 | (4-chloro-3-methyl-phenoxy)-acetic acid methyl ester | EIMS: m/z 214(M$^+$, $^{35}$Cl), 216(M$^+$, $^{37}$Cl). |
| 45 | (4-bromo-2-chloro-phenoxy)-acetic acid methyl ester | EIMS: m/z 278(M$^+$, $^{35}$Cl, $^{79}$Br), 280(M$^+$, $^{35}$Cl, $^{81}$Br or $^{37}$Cl, $^{79}$Br), 282(M$^+$, $^{37}$Cl, $^{81}$Br). Analysis for $C_9H_8BrClO_3$: calcd: C, 38.67; H, 2.88; found: C, 38.99; H, 2.81. |
| 46 | (2,4-dibromo-phenoxy)-acetic acid methyl ester | EIMS: m/z 322(M$^+$, $^{79}$Br, $^{79}$Br), 324(M$^+$, $^{79}$Br, $^{81}$Br), 326(M$^+$, $^{81}$Br, $^{81}$Br). Analysis for $C_9H_8Br_2O_3$: calcd: C, 33.37; H, 2.49; found: C, 33.51; H, 2.51. |
| 47 | (4-bromo-3-methyl-phenoxy)-acetic acid methyl ester | EIMS: m/z 258(M$^+$, $^{79}$Br), 260(M$^+$, $^{81}$Br). Analysis for $C_{10}H_{11}BrO_3$: calcd: C, 46.36; H, 4.28; found: C, 45.98; H, 4.22. |
| 48 | (4-bromo-2-nitro-phenoxy)-acetic acid methyl ester | EIMS: m/z 289(M$^+$, $^{79}$Br), 291(M$^+$, $^{81}$Br). Analysis for $C_9H_8BrNO_5$: calcd: C, 37.27; H, 2.78; N, 4.83; found: C, 37.38; H, 2.78; N, 4.80. |
| 49 | (4-bromo-2-isoxazol-5-yl-phenoxy)-acetic acid methyl ester | ESIMS: m/z 312[(M+H)$^+$, $^{79}$Br], 314[(M+H)$^+$, $^{81}$Br]. Analysis for $C_{12}H_{10}BrNO_4$: calcd: C, 46.18; H, 3.23; N, 4.49; found: C, 46.04; H, 3.26; N, 4.40. |
| 50 | (4-bromo-2-methoxy-phenoxy)-acetic acid methyl ester | EIMS: m/z 274(M$^+$, $^{79}$Br), 276(M$^+$, $^{81}$Br). Analysis for $C_{10}H_{11}BrO_4$: calcd: C, 43.66; H, 4.03; found: C, 43.88; H, 4.05. |

-continued

| Prep. # | Compound | Data |
|---|---|---|
| 51 | (2-chloro-4-nitro-phenoxy)-acetic acid methyl ester | EIMS: m/z 245($M^+$, $^{35}Cl$), 247($M^+$, $^{37}Cl$). Analysis for $C_9H_8ClNO_5$: calcd: C, 44.01; H, 3.28; N, 5.70; found: C, 44.06; H, 3.29; N, 5.61. |
| 52 | (2-bromo-4-nitro-phenoxy)-acetic acid methyl ester | EIMS: m/z 289($M^+$, $^{79}Br$), 291($M^+$, $^{81}Br$). Analysis for $C_9H_8BrNO_5$: calcd: C, 37.27; H, 2.78; N, 4.83; found: C, 37.08; H, 2.59; N, 4.75. |
| 53 | (2-chloro-4-trifluoromethyl-phenoxy)-acetic acid methyl ester | EIMS: m/z 268($M^+$, $^{35}Cl$), 270($M^+$, $^{37}Cl$). Analysis for $C_{10}H_8ClF_3O_3$: calcd: C, 44.71; H, 3.00; found: C, 44.90; H, 3.08. |
| 54 | (2-bromo-4-trifluoromethyl-phenoxy)-acetic acid methyl ester | EIMS: m/z 312($M^+$, $^{79}Br$), 314($M^+$, $^{81}Br$). Analysis for $C_{10}H_8BrF_3O_3$: calcd: C, 38.37; H, 2.58; found: C, 38.13; H, 2.42. |
| 55 | (4-chloro-2,6-dimethyl-phenoxy)-acetic acid methyl ester | EIMS: m/z 228($M^+$, $^{35}Cl$), 230($M^+$, $^{37}Cl$). Analysis for $C_{11}H_{13}ClO_3$: calcd: C, 57.78; H, 5.73; found: C, 57.94; H, 5.43. |
| 56 | (2, 4-dichloro-6-methyl-phenoxy)-acetic acid methyl ester | EIMS: m/z 248($M^+$, $^{35}Cl$), 250($M^+$, $^{35}Cl$, $^{37}Cl$), 252($M^+$, $^{37}Cl$, $^{37}Cl$). Analysis for $C_{10}H_{10}Cl_2O_3$: calcd: C, 48.22; H, 4.05; found: C, 48.16; H, 4.08: |
| 57 | (4-chloro-2-isopropyl-5-methyl-phenoxy)-acetic acid methyl ester | EIMS: m/z 256($M^+$, $^{35}Cl$), 258($M^+$, $^{37}Cl$). Analysis for $C_{13}H_{17}ClO_3$: calcd: C, 60.82; H, 6.67; found: C, 60.81; H, 6.57. |
| 58 | (4-bromo-2,6-dimethyl-phenoxy)-acetic acid methyl ester | EIMS: m/z 272($M^+$, $^{79}Cl$), 274($M^+$, $^{81}Cl$). |
| 59 | (4-bromo-3,5-dimethyl-phenoxy)-acetic acid methyl ester | EIMS: m/z 272($M^+$, $^{79}Br$), 274($M^+$, $^{81}Br$). Analysis for $C_{11}H_{13}BrO_3$: calcd: C, 48.37; H, 4.80; found: C, 48.44; H, 4.75. |
| 60 | (benzofuran-5-yloxy)-acetic acid methyl ester | EIMS: m/z 206($M^+$). |
| 61 | (benzo[1,3]dioxol-5-yloxy)-acetic acid methyl ester | EIMS: m/z 210($M^+$). |
| 62 | (4-chloro-naphthalen-1-yloxy)-acetic acid methyl ester | EIMS: m/z 250($M^+$, $^{35}Cl$), 252($M^+$, $^{37}Cl$). |
| 63 | (4-bromo-phenylsulfanyl)-acetic acid methyl ester | EIMS: m/z 260($M^+$, $^{79}Br$), 262($M^+$, $^{81}Br$). Analysis for $C_9H_9BrO_2S$: calcd: C, 41.40; H, 3.47; found: C, 41.19; H, 3.47. |
| 64 | [(4-Chloro-phenyl)-methyl-amino]-acetic acid methyl ester | EIMS: m/z 213($M^+$, $^{35}Cl$), 215($M^+$, $^{37}Cl$). |

Preparation 65

4-(2,2-di-ethoxy-ethoxy)-benzonitrile

Powdered potassium carbonate (5.18 g, 37.7 mmol) is added to a stirred solution of 4-cyanophenol (2.00 g, 16.8 mmol) and bromoacetaldehyde diethyl acetal (4.53 mL, 30.3 mmol) in anhydrous DMF (20 mL). The resultant mixture is stirred at 85° C. under nitrogen for 3 days. The mixture is cooled to ambient temperature; then water (100 mL) and EtOAc (100 mL) are added to the mixture. The organic layer is separated, dried over $MgSO_4$, filtered and concentrated. The oil is chromatographed on silica (gradient 5-20% EtOAc in hexane) to give 2.80 g (11.9 mmol, 71% yield) of the title compound. $^1H$ NMR ($CDCl_3$): δ1.24 (t, J=7.1 Hz, 6H), 3.60-3.68 (m, 2H), 3.73-3.81 (m, 2H), 4.04 (d, J=5.2 Hz, 2H), 4.83 (t, J=5.2 Hz, 1H), 6.97 (br d, J=9.2 Hz, 2H), 7.58 (br d, J=9.2 Hz, 2H); Analysis for $C_{13}H_{17}NO_3$: calcd: C, 66.36; H, 7.28; N, 5.95; found: C, 66.41; H, 7.34; N, 6.01.

Preparation 66

(4-chloro-2-propyl-phenoxy)-acetic acid methyl ester

Add 5% Pt/C sulfided (250 mg) to a stirred solution of (2-allyl-4-chloro-phenoxy)-acetic acid methyl ester (587 mg, 2.44 mmol) in EtOAc (10 mL) at ambient temperature under nitrogen. The mixture is flushed with hydrogen for 1 minute then stirred vigorously under hydrogen (balloon) for 1 hour. After filtration and concentration, 584 mg (100% yield) of the title compound is obtained as oil. EIMS: m/z 242 ($M^+$, $^{35}Cl$), 244($M^+$, $^{37}Cl$). Analysis for $C_{12}H_{15}ClO_3$: calcd: C, 59.39; H, 6.23; found: C, 59.01; H, 6.14.

Preparation 67

(5-chloro-biphenyl-2-yloxy)-acetic acid methyl ester

An aqueous $Na_2CO_3$ solution (2M, 18.5 mL) is added to a stirred solution of (2-bromo-4-chloro-phenoxy)-acetic acid methyl ester (5.03 g, 18.0 mmol), phenylboronic acid (2.24 g, 18.4 mmol) and tetrakis(triphenylphosphine)palladium (0) (1.04 g, 0.900 mmol) in 1,4-dioxane (50 mL) at ambient temperature under argon. The resultant mixture is heated at 95° C. for 24 hours. At ambient temperature, 5N HCl (18.5 mL) is added to the mixture, followed by the addition of EtOAc (70 mL) and saturated aqueous NaCl solution (50 mL). The organic layer is separated, dried over $MgSO_4$, filtered and concentrated. After chromatography on silica gel ($CH_2Cl_2$ followed by 0.5% HOAc/1% MeOH/98.5%

CH₂Cl₂), 1.30 g (4.70 mmol, 26% yield) of the title compound and 2.41 g of the corresponding acid are obtained. The acid is dissolved in MeOH (5 mL)/CH₂Cl₂ (20 mL), and the solution is treated dropwise with (trimethylsilyl)diazomethane (2M in hexane, 8.8 mL). After stirring for 1 hour, the mixture is concentrated and chromatographed on silica gel (1:1 CH₂Cl₂/hexane) to give another 2.68 g of the title compound (9.68 mmol, 80% total yield) as oil. $^1$H NMR (CDCl₃): δ3.77 (s, 3H), 4.58 (s, 2H), 6.80 (d, J=8.8 Hz, 1H), 7.21-7.26 (m, 1H), 7.33-7.37 (m, 2H), 7.42 (br t, J=7.4 Hz, 2H), 7.56 (d, J=6.9 Hz, 2H).

Using a method similar to Preparation 67, the following compounds may be prepared and isolated.

| Prep. # | Compound | Data |
|---|---|---|
| 68 | (5-chloro-3'-fluoro-biphenyl-2-yloxy)-acetic acid methyl ester | EIMS: m/z 294(M⁺, $^{35}$Cl), 296(M⁺, $^{37}$Cl). |
| 69 | (5,2'-dichloro-biphenyl-2-yloxy)-acetic acid methyl ester | EIMS: m/z 310(M⁺, $^{35}$Cl, $^{35}$Cl), 312(M⁺, $^{35}$Cl, $^{37}$Cl), 314(M⁺, $^{37}$Cl, $^{37}$Cl). |
| 70 | (5,3'-dichloro-biphenyl-2-yloxy)-acetic acid methyl ester | EIMS: m/z 310(M⁺, $^{35}$Cl, $^{35}$Cl), 312(M⁺, $^{35}$Cl, $^{37}$Cl), 314(M⁺, $^{37}$Cl, $^{37}$Cl). |
| 71 | (5,4'-dichloro-biphenyl-2-yloxy)-acetic acid methyl ester | EIMS: m/z 310(M⁺, $^{35}$Cl, $^{35}$Cl), 312(M⁺, $^{35}$Cl, $^{37}$Cl), 314(M⁺, $^{37}$Cl, $^{37}$Cl). |
| 72 | (4-chloro-2-furan-2-yl-phenoxy)-acetic acid methyl ester | $^1$H NMR(CDCl₃): δ3.80(s, 3H), 4.66(s, 2H), 6.47(dd, J=3.4Hz and 2.0Hz, 1H), 6.68-6.72(m, 2H), 7.26(d, J=3.4Hz, 1H), 7.43(d, J=2.0Hz, 1H), 7.82(d, J=2.9Hz, 1H). |
| 73 | (4-chloro-2-thiophen-2-yl-phenoxy)-acetic acid methyl ester | EIMS: m/z 282(M⁺, $^{35}$Cl), 284(M⁺, $^{37}$Cl). |
| 74 | (4-chloro-2-thiophen-3-yl-phenoxy)-acetic acid methyl ester | EIMS: m/z 282(M⁺, $^{35}$Cl), 284(M⁺, $^{37}$Cl). Analysis for C₁₃H₁₁ClO₃S: calcd: C, 55.22; H, 3.92; found: C, 55.31; H, 3.88. |

Preparation 75

4-bromo-1-(2,2-dimethoxy-ethoxy)-2-methyl-benzene

Powdered potassium carbonate (3.36 g, 24.3 mmol) is added to a stirred solution of 4-bromo-2-methylphenol (3.03 g, 16.2 mmol) and bromoacetaldehyde dimethyl acetal (3.56 g, 21.1 mmol) in anhydrous DMF (20 mL). The resultant mixture is stirred at 85° C. under nitrogen for 24 hours. The mixture is cooled to ambient temperature; then water (100 mL) and EtOAc (100 mL) are added to the mixture. The organic layer is separated, dried over MgSO₄, filtered and concentrated. The oil is chromatographed on silica (gradient 5-20% EtOAc in hexane) to give 1.78 g (6.47 mmol, 40% yield) of the title compound. EIMS: m/z 274 (M⁺, $^{79}$Br), 276 (M⁺, $^{81}$Br). Analysis for C₁₁H₁₅BrO3: calcd: C, 48.02; H, 5.50; found: C, 48.32; H, 5.53.

Preparation 76

(5-nitro-biphenyl-2-yloxy)-acetic acid methyl ester

An aqueous Na₂CO₃ solution (2M, 3.79 mL) is added to a stirred solution of (2-bromo-4-nitro-phenoxy)-acetic acid methyl ester (1.06 g, 3.70 mmol), phenylboronic acid (450 mg, 3.72 mmol) and tetrakis(triphenylphosphine)palladium (0) (210 mg, 0.185 mmol) in 1,4-dioxane (10 mL) at ambient temperature under argon. The resultant mixture is heated at ~95° C. for 24 hours. At ambient temperature, 5N HCl (3.8 mL) is added to the mixture, followed by the addition of EtOAc (50 mL) and saturated aqueous NaCl solution (15 mL). The organic layer is separated, dried over MgSO₄, filtered and concentrated. The crude product is dissolved in MeOH (5 mL)/CH₂Cl₂ (20 mL) and the solution is treated dropwise with (trimethylsilyl)diazomethane (2M in hexane, 2.8 mL). After stirring for 1 hour, the mixture is concentrated and chromatographed on silica gel (gradient 50-75% CH₂Cl₂ in hexane) to give 760 mg (2.64 mmol, 71% yield) of the title compound as oil. ESIMS: m/z 288 (M+H)⁺.

Using methods similar to Preparation 76, the following compounds may be prepared and isolated.

| Prep. # | Compound | Data |
|---|---|---|
| 77 | (5-nitro-2'-chloro-biphenyl-2-yloxy)-acetic acid methyl ester | EIMS: m/z 321(M⁺, $^{35}$Cl), 323(M⁺, $^{37}$Cl). |
| 78 | (5-nitro-3'-chloro-biphenyl-2-yloxy)-acetic acid methyl ester | EIMS: m/z 321(M⁺, $^{35}$Cl), 323(M⁺, $^{37}$Cl). |
| 79 | (5-trifluoromethyl-biphenyl-2-yloxy)-acetic acid methyl ester | EIMS: m/z 310(M⁺). |
| 80 | (3'-fluoro-5-trifluoromethyl-biphenyl-2-yloxy)-acetic acid methyl ester | $^1$H NMR(CDCl₃): δ3.80(s, 3H), 4.71(s, 2H), 6.91(d, J=8.8Hz, 1H), 7.04-7.11(m, 1H), 7.33-7.44(m, 3H), 7.57(br d, J=9.2Hz, 1H), 7.60(br s, 1H). |
| 81 | (3'-chloro-5-trifluoromethyl-biphenyl-2-yloxy)-acetic acid methyl ester | EIMS: m/z 344(M⁺, $^{35}$Cl), 346(M⁺, $^{37}$Cl). |

Preparation 82

[2-(7-bromo-isoquinoline-5-sulfonylamino)-ethyl]-carbamic acid tert-butyl ester 7-Bromo-isoquinoline (22.7 g, 109 mmol) is added to a stirred chlorosulfonic acid (230 mL) solution and the resultant mixture is heated at 150° C. under nitrogen for 22 hours. The solution is cooled to ambient temperature and poured very slowly into ice (2 Kg) cooled in a −10° C. bath. While cold, the mixture is adjusted to pH ~10 with powered $Na_2CO_3$ (ca. 200 g) and 5N NaOH. The mixture is extracted with dichloromethane (1 L×2). The combined organic layers are dried over $Na_2SO_4$, filtered and concentrated in vacuo to give 16.3 g (crude yield 49%) of 7-bromo-isoquinoline-5-sulfonyl chloride as a tan solid.

A slurry of 7-bromo-isoquinoline-5-sulfonyl chloride (16.3 g, 35.5 mmol) in $CH_2Cl_2$ (200 mL) is added in small portions to a stirred solution of (2-amino-ethyl)-carbamic acid tert-butyl ester (6 mL, 37.9 mmol) and pyridine (2.79 mL, 34.5 mmol) in $CH_2Cl_2$ (100 mL) at 0° C. under nitrogen. The resultant mixture is allowed to stir at ambient temperature overnight. The mixture is diluted with another 100 mL $CH_2Cl_2$, washed with saturated aqueous $NaHCO_3$ (150 mL) solution, dried, filtered and concentrated. The dark oil is subject to column chromatography (Biotage 75 short; eluted with 10-20% $CH_3CN/CH_2Cl_2$+0.2% $NEt_3$) to give the title compound as a white solid. ESIMS: m/z 430 [(M+H)$^+$, $^{79}$Br], 432 [(M+H)$^+$, $^{81}$Br].

Preparation 83

[2-(7-phenyl-isoquinoline-5-sulfonylamino)-ethyl]-carbamic acid tert-butyl ester An aqueous $Na_2CO_3$ solution (2M, 7.22 mL) is added to a stirred solution of [2-(7-bromo-isoquinoline-5-sulfonylamino)-ethyl]-carbamic acid tert-butyl ester (3.03 g, 7.04 mmol), phenylboronic acid (0.876 g, 7.18 mmol) and tetrakis(triphenylphosphine)palladium (0) (0.407 g, 0.352 mmol) in 1,4-dioxane (36 mL) at ambient temperature under argon. The resultant mixture is heated at 95° C. for 24 hours. At ambient temperature, EtOAc (200 mL)/$CH_2Cl_2$ (50 mL) and half-saturated aqueous NaCl solution (200 mL) are added to the mixture. The organic layer is separated, dried over $MgSO_4$, filtered and concentrated. After chromatography on silica gel (gradient 0-3% $CH_3OH$ in $CH_2Cl_2$), 2.83 g (6.62 mmol, 94% yield) of the title compound is obtained as a white solid. ESIMS: m/z 428 (M+H)$^+$.

Preparation 84

7-phenyl-isoquinoline-5-sulfonic acid (2-amino-ethyl)-amide di-hydrochloride A 4N HCl solution in 1,4-dioxane (22 mL) is added to a stirred solution of [2-(7-phenyl-isoquinoline-5-sulfonylamino)-ethyl]-carbamic acid tert-butyl ester (2.50 g, 5.85 mmol) in $CH_2Cl_2$ (40 mL)/$CH_3OH$ (6 mL) at ambient temperature under nitrogen. The resultant white suspension is stirred for 4 hours. At filtration and vacuum drying at 50° C., 2.34 g (5.85 mmol, 100% yield) of the title compound is obtained as a white solid. ESIMS: m/z 328 (M+H)$^+$.

Preparation 85

[2-(1-chloro-isoquinoline-5-sulfonylamino)-ethyl]-carbamic acid tert-butyl ester Chlorosulfonic acid (40 mL) is added slowly to 1-chloro-isoquinoline (9.92 g, 60.6 mmol) at 0° C. with stirring under nitrogen. The resultant mixture is heated at 155° C. for 24 hours. Then the mixture is cooled to ambient temperature before it is poured very slowly into ice (200 g). While cold, the mixture is extracted with dichloromethane (300 mL). The organic layer is dried over $Na_2SO_4$, filtered and concentrated in vacuo to give 13.6 g (51.9 mmol, yield 86%) of 1-chloro-isoquinoline-5-sulfonyl chloride as a white powder. $^1$H NMR ($CDCl_3$): δ7.87(t, J=7.5 Hz, 1H), 8.52 (d, J=6.2 Hz, 1H), 8.59 (d, J=6.2 Hz, 1H), 8.62 (d, J=7.5 Hz, 1H), 8.82 (d, J=7.5 Hz, 1H).

Powdered 1-chloro-isoquinoline-5-sulfonyl chloride (10.0 g, 38.2 mmol) is added in portions to a stirred solution of (2-amino-ethyl)-carbamic acid tert-butyl ester (7.33 g, 45.8 mmol) and $NEt_3$ (10.7 mL, 76.4 mmol) in anhydrous $CH_2Cl_2$ (200 mL) at 0° C. under nitrogen. The resultant mixture is allowed to stir at ambient temperature for 4 hours. The mixture is concentrated and chromatographed on silica gel (gradient 0-5% $CH_3OH$ in $CH_2Cl_2$) to give 13.8 g (35.8 mmol, 94% yield) of the title compound as foam. ESIMS: m/z 386 [(M+H)$^+$, $^{35}$Cl], 388 [(M+H)$^+$, $^{37}$Cl]. Analysis for $C_{16}H_{20}ClN_3O_4S$: calcd: C, 49.80; H, 5.22; N, 10.89; found: C, 49.70; H, 5.22; N, 10.72.

Preparation 86

1-chloro-isoquinoline-5-sulfonic acid (2-amino-ethyl)-amide hydrochloride

A small stream of hydrogen chloride is bubbled through a stirred solution of [2-(1-chloro-isoquinoline-5-sulfonylamino)-ethyl]-carbamic acid tert-butyl ester (6.74 g, 17.5 mmol) in anhydrous $CH_2Cl_2$ (100 mL) at 0° C. under nitrogen for 10 minutes. The resultant white suspension is allowed to stir at ambient temperature for 1 hour. After filtration and vacuum drying at 50° C., 5.61 g (17.4 mmol, 100% yield) of the title compound is obtained as a white powder. ESIMS: m/z 286 [(M+H)$^+$, $^{35}$Cl], 288 [(M+H)$^+$, $^{37}$Cl]. Analysis for $C_{11}H_{13}Cl_2N_3O_2S.0.3H_2O$: calcd: C, 40.33; H, 4.18; N, 12.83; found: C, 40.34; H, 3.80; N, 12.43.

Preparation 87

1-chloro-isoquinoline-5-sulfonic acid (2-amino-ethyl)-amide

A 5N NaOH solution (0.937 mL) is added slowly to a stirred suspension of 1-chloro-isoquinoline-5-sulfonic acid (2-amino-ethyl)-amide hydrochloride (1.51 g, 4.69 mmol) in THF (20 mL)/$CH_3OH$ (20 mL) at ambient temperature to form a clear solution. After concentration in vacuo, the tan solid is suspended in EtOAc/$CH_3OH$ and sonicated for a few minutes. The mixture is filtered and concentrated to give 1.21 g (4.23 mmol, 90% yield) of the title compound as a tan powder. ESIMS: m/z 286 [(M+H)$^+$, $^{35}$Cl], 288 [(M+H)$^+$, $^{37}$Cl].

Preparation 88

Isoquinoline-5-sulfonic acid tert-butylamide

Powdered isoquinoline-5-sulfonyl chloride hydrochloride (1.00 g, 3.79 mmol) is added in small portions to a stirred solution of tert-butylamine (2.00 mL, 18.9 mmol) in $CH_2Cl_2$ (10 mL) at 0° C. under nitrogen. The resultant mixture is allowed to stir at ambient temperature for 1 hour. Ethyl acetate (50 mL) is added to the mixture and the mixture is washed with saturated aqueous $NaHCO_3$ (20 mL). The organic layer is dried over $MgSO_4$, filtered and concentrated.

The crude product is chromatographed on silica (gradient 0-2% $CH_3OH$ in $CH_2Cl_2$) to give 857 mg (3.24 mmol, 86% yield) of the title compound as a white solid. ESIMS: m/z 265 $(M+H)^+$. Analysis for $C_{13}H_{16}N_2O_2S$: calcd: C, 59.07; H, 6.10; N, 10.60; found: C, 59.21; H, 6.01; N, 10.67.

Preparation 89

2-benzyl-1-(3-bromo-propoxy)-4-chloro-benzene

Powdered $K_2CO_3$ (2.07 g, 15.0 mmol) is added to a stirred solution of 2-benzyl-4-chlorophenol (2.19 g, 10.0 mmol) and 1,3-dibromopropane (3.05 mL, 30.0 mmol) in anhydrous DMF (20 mL) at ambient temperature under nitrogen; The mixture is heated at 80° C. for 1 hour. At ambient temperature, EtOAc (100 mL) and water (150 mL) are added to the mixture. The organic layer is separated, dried over $MgSO_4$, filtered and concentrated. The crude product is chromatographed on silica (gradient 0-2% EtOAc in hexane) to give 2.45 g (7.21 mmol, 72% yield) of the title compound as a white solid. EIMS: m/z 338 $(M^+, {}^{35}Cl, {}^{79}Br)$, 340 $(M^+, {}^{37}Cl, {}^{37}Br$ or ${}^{35}Cl, {}^{81}Br)$, 342 $(M^+, {}^{37}Cl, {}^{81}Br)$.

Preparation 90

2-benzyl-1-(3-bromo-propoxy)-benzene

By following similar procedure as described in Preparation 89, O-alkylation of 2-benzylphenol with 1,3-dibromopropane gives the title-compound as oil. EIMS: m/z 304 $(M^+, {}^{79}Br)$, 306 $(M^+, {}^{81}Br)$.

Preparation 91

[3-(2-benzyl-4-chloro-phenoxy)-propyl]-[bis-(4-methoxy-phenyl)-methyl]-amine 1,1-di(p-anisyl)methylamine (2.06 g, 8.48 mmol) is added to a stirred solution of 2-benzyl-1-(3-bromo-propoxy)-4-chloro-benzene (2.40 g, 7.07 mmol) and diisopropylethylamine (1.85 mL, 10.6 mmol) in anhydrous 1,4-dioxane (10 mL) at ambient temperature under nitrogen. The mixture is heated at 95° C. for 24 hours. At ambient temperature, EtOAc (100 mL) and half-saturated aqueous $NaHCO_3$ solution (60 mL) are added to the mixture. The organic layer is separated, dried over $MgSO_4$, filtered and concentrated. The crude product is chromatographed on silica (gradient 5-12% EtOAc in hexane) to give 3.08 g (6.13 mmol, 87% yield) of the title compound as oil. ESIMS: m/z 502 $[(M+H)^+, {}^{35}Cl]$, 504 $[(M+H)^+, {}^{37}Cl]$.

Preparation 92

[3-(2-benzyl-phenoxy)-propyl]-[bis-(4-methoxy-phenyl)-methyl]-amine

By following similar procedure as described in Preparation 91, N-alkylation of 1,1-di(p-anisyl)methylamine with 2-benzyl-1-(3-bromo-propoxy)-benzene gives the title compound as oil. ESIMS: m/z 468 $(M+H)^+$. Analysis for $C_{31}H_{33}NO_3$: calcd: C, 79.63; H, 7.11; N, 3.00; found: C, 79.49; H, 7.17; N, 2.96.

Preparation 93

{[3-(2-benzyl-4-chloro-phenoxy)-propyl]-[bis-(4-methoxy-phenyl)-methyl]-amino}-acetonitrile Bromoacetonitrile (0.575 mL, 8.25 mmol) is added to a stirred solution of [3-(2-benzyl-4-chloro-phenoxy)-propyl]-[bis-(4-methoxy-phenyl)-methyl]-amine (2.76 g, 5.50 mmol) and diisopropylethylamine (1.44 mL, 8.25 mmol) in anhydrous 1,4-dioxane (20 mL) at ambient temperature under nitrogen. The mixture is heated at 90° C. for 4 hours. At ambient temperature, EtOAc (100 mL) and half-saturated aqueous $NaHCO_3$ solution (100 mL) are added to the mixture. The organic layer is separated, dried over $MgSO_4$, filtered and concentrated. The crude product is chromatographed on silica (gradient 5-16% EtOAc in hexane) to give 2.88 g (5.32 mmol, 97% yield) of the title compound as oil. ESIMS: m/z 541 $[(M+H)^+, {}^{35}Cl]$, 543 $[(M+H)^+, {}^{37}Cl]$. Analysis for $C_{33}H_{33}ClN_2O_3$: calcd: C, 73.25; H, 6.15; N, 5.18; found: C, 73.05; H, 6.28; N, 5.02.

Preparation 94

{[3-(2-benzyl-phenoxy)-propyl]-[bis-(4-methoxy-phenyl)-methyl]-amino}-acetonitrile By following similar procedure as described in Preparation 93, N-alkylation of [3-(2-benzyl-phenoxy)-propyl]-[bis-(4-methoxy-phenyl)-methyl]-amine with bromoacetonitrile gives the title compound as oil. FABMS: m/z 506 $(M)^+$, 507 $(M+H)^+$.

Preparation 95

$N^1$-[3-(2-benzyl-4-chloro-phenoxy)-propyl]-$N^1$-[bis-(4-methoxy-phenyl)-methyl]-ethane-1,2-diamine $LiAlH_4$ (6.88 mL, 1N in THF) is added dropwise to a stirred solution of {[3-(2-benzyl-4-chloro-phenoxy)-propyl]-[bis-(4-methoxy-phenyl)-methyl]-amino}-acetonitrile (2.48 g, 4.58 mmol) in anhydrous THF (30 mL) at ambient temperature under nitrogen. The resultant mixture is allowed to stir at ambient temperature for 20 hours. The mixture is cooled to 0° C. before it is treated dropwise with $CH_3OH$ (5 mL), then followed by the addition of $Et_2O$ (30 mL) and saturated Rochelle's salt solution (80 mL). The two-layered mixture is allowed to stir vigorously at ambient temperature under nitrogen for 1 hour. Another 60 mL $Et_2O$ is added to the mixture. The organic layer is separated, dried over $MgSO_4$, filtered and concentrated. The crude product is chromatographed on silica (gradient 0-4% 2N $NH_3/CH_3OH$ in $CH_2Cl_2$) to give 1.92 g (3.52 mmol, 77% yield) of the title compound as oil. ESIMS: m/z 545 $[(M+H)^+, {}^{35}Cl]$; 547 $[(M+H)^+, {}^{37}Cl]$.

Preparation 96

$N^1$-[3-(2-benzyl-phenoxy)-propyl]-$N^1$-[bis-(4-methoxy-phenyl)-methyl]-ethane-1,2-diamine By following similar procedure as described in Preparation 95, $LiAlH_4$ reduction of {[3-(2-benzyl-phenoxy)-propyl]-[bis-(4-methoxy-phenyl)-methyl]-amino}-acetonitrile gives the title compound (85% yield) as oil. ESIMS: m/z 511 $(M+H)^+$.

Preparation 97

2-benzyl-4-chloro-phenylamine

Diisobutylaluminum hydride (10.8 mL, 1.0M in toluene) is added dropwise to a stirred solution of (2-amino-5-chloro-phenyl)-phenyl-methanone (2.00 g, 8.63 mmol) in anhydrous $CH_2Cl_2$ (20 mL) at −78° C. under nitrogen. The resultant solution is stirred at −78° C. for 1 hour, then at ambient temperature for 1 hour. Ethyl acetate (100 mL) and saturated aqueous Rochelle's salt solution (100 mL) are added to the mixture and the resultant two-layered mixture is stirred vigorously for 1 hour. The organic layer is separated, dried over $MgSO_4$, filtered, concentrated and chromatographed on silica (gradient 10-50% EtOAc in hexane) to give 1.85 g (7.92 mmol, 92% yield) of the desired alcohol as oil. ESIMS: m/z 232 [(M−H)$^-$, $^{35}$Cl], 234 [(M−H)$^-$, $^{37}$Cl]. Analysis for $C_{13}H_{12}ClNO$: calcd: C, 66.81; H, 5.18; N, 5.99; found: C, 66.89; H, 5.26; N, 6.01.

The above alcohol (1.80 g, 7.70 mmol) is dissolved in $CH_2Cl_2$ (20 mL) and the solution is treated successively with triethylsilane (2.46 mL, 15.4 mmol) and TFA (5.93 mL, 77.0 mmol). The resultant mixture is stirred at ambient temperature for 6 hours. After dilution with EtOAc (100 mL), the mixture is washed with saturated aqueous $NaCO_3$ solution (50 mL×2), dried over $MgSO_4$, filtered, concentrated and chromatographed on silica (gradient 10-50% EtOAc in hexane) to give 1.52 g (6.98 mmol, 91% yield) of the title compound as oil. ESIMS: m/z 218 [(M+H)$^+$, $^{35}$Cl], 220 [(M+H)$^+$, $^{37}$Cl].

Preparation 98

N-(2-benzyl-4-chloro-phenyl)-2,2,2-trifluoro-acetamide

Trifluoroacetic anhydride (0.713 mL, 5.05 mmol) is added dropwise to a stirred solution of 2-benzyl-4-chloro-phenylamine (1.00 g, 4.59 mmol) in anhydrous 1,2-dichloroethane (5 mL) at ambient temperature under nitrogen. The resultant mixture is stirred for 5 minutes. Dichloromethane (20 mL) and water (10 mL) are added to the mixture. The organic layer is separated, dried over $MgSO_4$, filtered and concentrated to give 1.31 g (4.18 mmol, 91% crude yield) of the title compound as a white solid. ESIMS: m/z 312 [(M−H)$^-$, $^{35}$Cl], 314 [(M−H)$^-$, $^{37}$Cl].

Preparation 99

[(2-benzyl-4-chloro-phenyl)-(2,2,2-trifluoro-acetyl)-amino]-acetic acid methyl ester Powdered potassium carbonate (1.10 g, 7.97 mmol) is added to a stirred solution of N-(2-benzyl-4-chloro-phenyl)-2,2,2-trifluoro-acetamide (1.25 g, 3.98 mmol) and methyl bromoacetate (1.34 g, 8.76 mmol) in anhydrous DMF (5 mL). The resultant mixture is stirred at ambient temperature under nitrogen for 2 hours. After dilution with EtOAc (60 mL), the mixture is washed with water (25 mL×3), dried over $MgSO_4$, filtered, concentrated and chromatographed on-silica (gradient 0-15% EtOAc in hexane) to give 1.37 g (3.55 mmol, 89% yield) of the title compound as oil. ESIMS: m/z 386 [(M+H)$^+$, $^{35}$Cl], 388 [(M+H)$^+$, $^{37}$Cl].

Preparation 100

[2-(2-Bromo-ethoxy)-5-chloro-phenyl]-phenyl-methanone

A mixture of (5-chloro-2-hydroxy-phenyl)-phenyl-methanone (0.93 g, 4.0 mmol), δ 1,2-dibromoethane (3.5 mL, 40 mmol) and potassium carbonate (0.83 g, 6.0 mmol) in acetonitrile (10 mL) is heated at reflux under $N_2$ over weekend (about 60 hours). After cooling to room temperature, solid potassium bromide is filtered off and washed with ca. 70 mL of acetonitrile. The filtrate is evaporated, and the crude mixture purified by column chromatography ($SiO_2$, 5-12% ethyl acetate in hexanes) to afford 1.18 g (87%) of the title compound as colorless product. APCI-MS: m/z 339 [(M+H)$^+$, $^{35}$Cl, $^{79}$Br], 341 [(M+H)$^+$, $^{37}$Cl, $^{79}$Br], 343 [(M+H)$^+$, $^{37}$Cl, $^{81}$Br]. $^1$H-NMR (300 MHz; CDCl3): δ7.78 (2H d, 8.1 Hz); 7.58 (1H, br t, 7.5 Hz); 7.38-7.50 (4H, m); 6.92 (1H, d, 8.6 Hz); 4.18 (2H, t; 6.5 Hz); 3.26 (2H, t, 6.5 Hz).

Preparation 101

1-Hydroxy-isoquinoline-5-sulfonic acid (2-amino-ethyl)-amide hydrochloride

A stirred mixture of [2-(1-chloro-isoquinoline-5-sulfonylamino)-ethyl]-carbamic acid tert-butyl ester (10.8 g, 28.0 mmol) and 5N HCl (140 mL) is heated at 90° C. for 3 hours. It turns into a clear solution after 45 minutes, then becomes a white suspension 15 minutes later. The mixture is cooled to ambient temperature. After filtration and vacuum drying at 50° C., 7.34 g (86% yield) of the title compound is obtained as a white powder.

Preparation 102

1-Hydroxy-isoquinoline-5-sulfonic acid (2-amino-ethyl)-amide sodium chloride A 1N NaOH solution (5.96 mL) is added slowly to a stirred suspension of 1-hydroxy-isoquinoline-5-sulfonic acid (2-amino-ethyl)-amide hydrochloride (1.81 g, 5.96 mmol) in $CH_3OH$ (10 mL) at ambient temperature under nitrogen. The resultant mixture is allowed to stir for 30 minutes. The mixture is then concentrated at 50° C. under vacuum to give a 1.87 g of the title compound (96% yield) as a white powder.

Preparation 103

1-Chloro-isoquinoline-5-sulfonic acid (2-{[3-(2-benzyl-4-chloro-phenoxy)-propyl]-[bis-(4-methoxy-phenyl)-methyl]-amino}-ethyl)-amide Powdered 1-chloro-isoquinoline-5-sulfonyl chloride (124 mg, 0.473 mmol) is added to a stirred solution of $N^1$-[3-(2-benzyl-4-chloro-phenoxy)-propyl]-$N^1$-[bis-(4-methoxy-phenyl)-methyl]-ethane-1,2-diamine (258 mg, 0.473 mmol) and $NEt_3$ (0.198 mL, 1.42 mmol) in anhydrous $CH_2Cl_2$ (5 mL) at ambient temperature under nitrogen. The resultant mixture is allowed to stir for 1 hour. The mixture is chromatographed on silica gel (gradient 0-4% EtOAc in $CH_2Cl_2$) to give 285 mg (0.370 mmol, 78% yield) of the title compound as foam. ESIMS: m/z 768 [(M−H)$^-$, $^{35}$C, $^{35}$Cl], 770 [(M−H)$^-$, $^{35}$Cl, $^{37}$Cl], 772 [(M−H)$^-$, $^{37}$Cl, $^{37}$Cl. Analysis for $C_{42}H_{41}Cl_2N_3O_5S$: calcd: C, 65.45; H, 5.36; N, 5.45; found: C, 65.43; H, 5.27; N, 5.42.

Using a method analogous to Preparation 103, the following compounds may be prepared and isolated.

| Prep # | Compound | Data |
|---|---|---|
| 104 | Isoquinoline-5-sulfonic acid (2-{[3-(2-benzyl-4-chloro-phenoxy)-propyl]-[bis-(4-methoxy-phenyl)-methyl]-amino}-ethyl)-amide | ESIMS: m/z 736[(M+H)$^+$, $^{35}$Cl], 738[(M+H)$^+$, $^{37}$Cl]. |
| 105 | 1-Chloro-isoquinoline-5-sulfonic acid (2-{[3-(2-benzyl-phenoxy)-propyl]-[bis-(4-methoxy-phenyl)-methyl]-amino}-ethyl)-amide | ESIMS: m/z 734[(M−H)$^−$, $^{35}$Cl], 736[(M−H)$^−$, $^{37}$Cl]. |
| 106 | Isoquinoline-5-sulfonic acid (2-{[3-(2-benzyl-phenoxy)-propyl]-[bis-(4-methoxy-phenyl)-methyl]-amino}-ethyl)-amide | ESIMS: m/z 702[(M+H)$^+$. |

Preparation 107

[2-(2-Benzyl-phenoxy)-ethyl]-[2-(isoquinoline-5-sulfonylamino)-ethyl]-carbamic acid tert-butyl ester Di-tert-butyl dicarbonate (57.4 mg, 0.263 mmol) is added to a stirred solution of isoquinoline-5-sulfonic acid {2-[2-(2-benzyl-phenoxy)-ethylamino]-ethyl}-amide (67.5 mg, 0.146 mmol) in anhydrous CH$_2$Cl$_2$ (1 mL) at ambient temperature under nitrogen. The resultant solution is stirred for 1 hour. The mixture is subject to chromatography on silica (gradient 0-10% CH$_3$OH in CH$_2$Cl$_2$) to give 82 mg (0.15 mmol, 100% yield) of the title compound as a gum. ESIMS: m/z 562 (M+H)$^+$. Analysis for C$_{31}$H$_{35}$N$_3$O$_5$S: calcd: C, 66.29; H, 6.28; N, 7.48; found: C, 65.96; H, 6.23; N, 7.37.

Preparation 108

[2-(2-Benzyl-phenoxy)-ethyl]-{2-[(isoquinoline-5-sulfonyl)-methyl-amino]-ethyl}-carbamic acid tert-butyl ester Powdered K$_2$CO$_3$ (50.4 mg, 0.365 mmol) is added to a stirred solution of [2-(2-benzyl-phenoxy)-ethyl]-[2-(isoquinoline-5-sulfonylamino)-ethyl]-carbamic acid tert-butyl ester (82.0 mg, 0.146 mmol) and CH$_3$I (18.2 µL, 0.292 mmol) in anhydrous DMF (1 mL) at ambient temperature under nitrogen. The resultant solution is stirred for 2 hours. The mixture is diluted with EtOAc (10 mL), washed with water (5 mL×3), dried over MgSO$_4$, filtered and concentrated. The crude product is chromatographed on silica (gradient 0-5% CH$_3$OH in CH$_2$Cl$_2$) to give 65 mg (0.11 mmol, 77% yield) of the title compound as a gum. ESIMS: m/z 576 (M+H)$^+$.

Using a procedure similar to that described in Preparation 108, the following compounds may be prepared and isolated.

| Prep. # | Compound | Data |
|---|---|---|
| 109 | [(2-{[2-(2-Benzyl-phenoxy)-ethyl]-tert-butoxycarbonyl-amino}-ethyl)-(isoquinoline-5-sulfonyl)-amino]-acetic acid tert-butyl ester | ESIMS: m/z 676(M+H)$^+$. |
| 110 | [2-(2-Benzyl-phenoxy)-ethyl]-{2-[(2-dimethylamino-ethyl)-(isoquinoline-5-sulfonyl)-amino]-ethyl}-carbamic acid tert-butylester | ESIMS: m/z 633(M+H)$^+$. |

Preparation 111

Preparation of [2-(2-bromo-4-fluoro-phenoxy)-ethyl]-[2-(isoquinoline-5-sulfonylamino)-ethyl]-carbamic acid tert-butyl ester

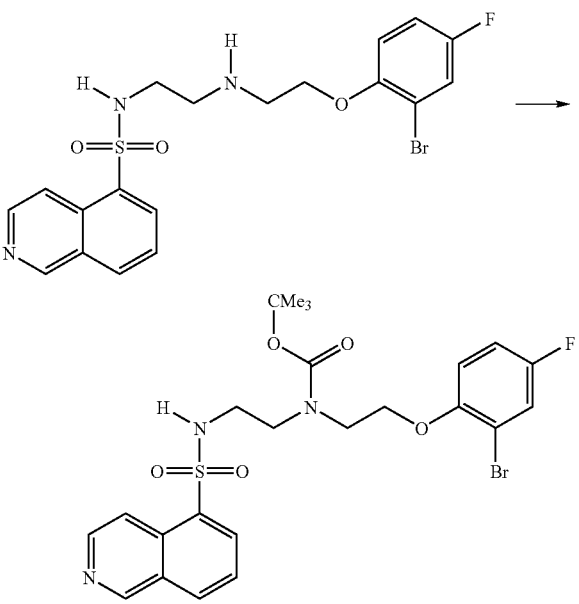

Di-tert-butyl dicarbonate (0.760 g, 3.48 mmol) is added to a stirred solution of isoquinoline-5-sulfonic acid {2-[2-(2-bromo-4-fluoro-phenyloxy)-ethylamino]-ethyl}-amide (1.36 g, 2.90 mmol) in anhydrous methylene chloride (10 mL). The mixture is allowed to stir at ambient temperature for 16 hours. After concentration and MPLC separation on silica (gradient 0-3% methanol in methylene chloride), 1.19 g (72% yield) of the title compound is obtained. ESIMS: m/z 568 [(M+H)$^+$, $^{79}$Br], 570 [(M+H)$^+$, $^{81}$Br].

Preparation 112

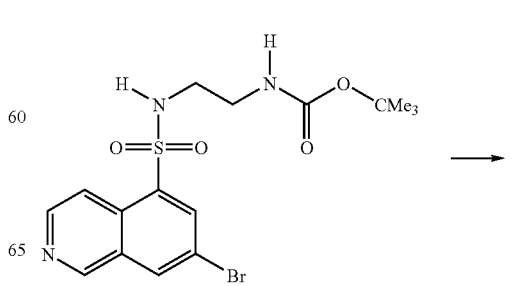

-continued

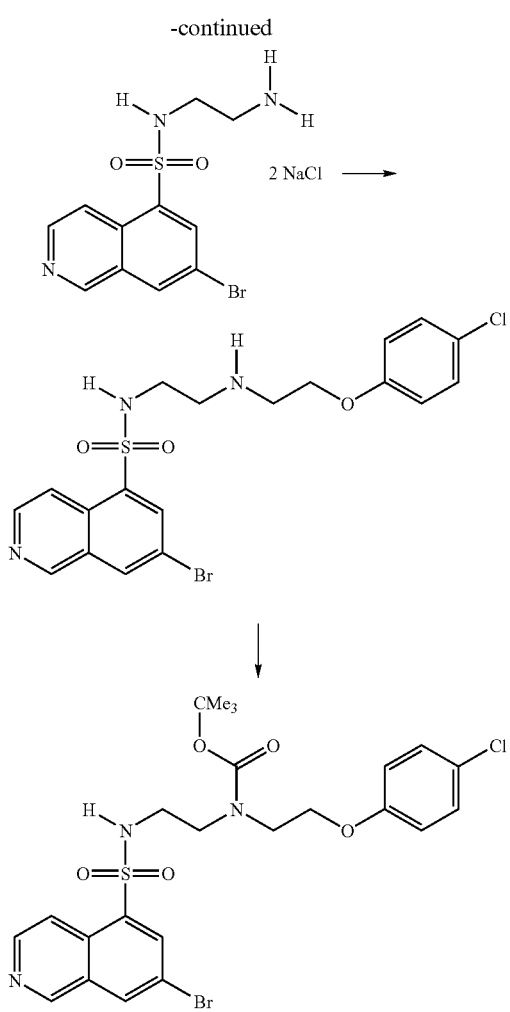

Preparation of 7-bromo-isoquinoline-5-sulfonic acid (2-amino-ethyl)-amide di-sodium chloride

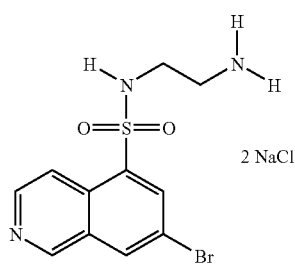

A small stream of anhydrous HCl gas is slowly bubbled through a stirred solution of [2-(7-bromo-isoquinoline-5-sulfonylamino)-ethyl]-carbamic acid tert-butyl ester (3.76 g) in methylene chloride (200 mL)/methanol (50 mL) at ambient temperature for 2 minutes. The suspension is capped with a glass stopper and stirred for 15 minutes. After concentration, the solid is dissolved in methanol (250 mL) and the solution is treated with a 5N NaOH solution (3.5 mL). The solution is concentrated to give 3.87 g (99% yield) of the title compound as a slightly yellow solid. ESIMS: m/z 330 [(M+H)+, 79Br], 332 [(M+H)+, 81Br].

Preparation of 7-bromo-isoquinoline-5-sulfonic acid {2-[2-(4-chloro-phenoxy) ethylamino]-ethyl}-amide

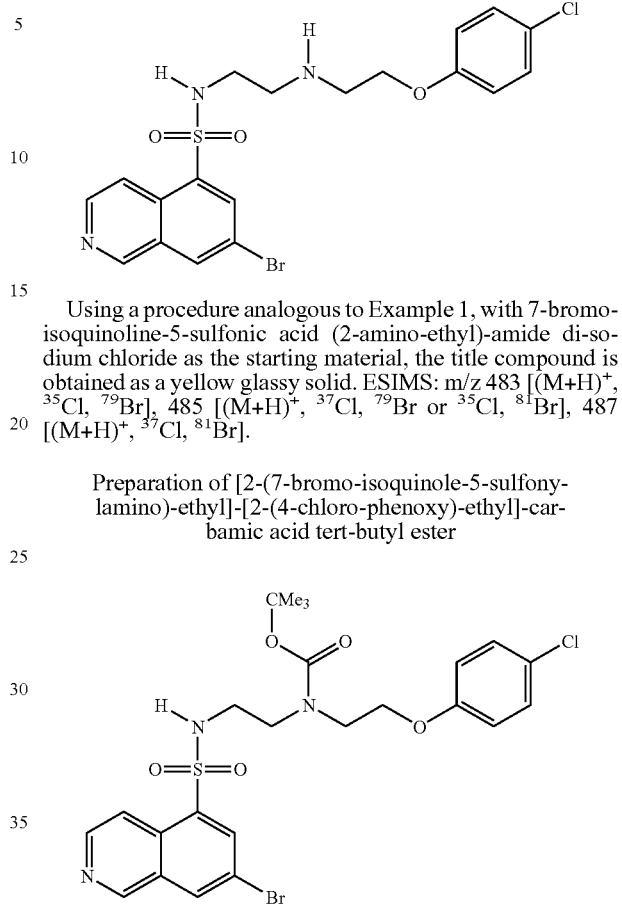

Using a procedure analogous to Example 1, with 7-bromo-isoquinoline-5-sulfonic acid (2-amino-ethyl)-amide di-sodium chloride as the starting material, the title compound is obtained as a yellow glassy solid. ESIMS: m/z 483 [(M+H)+, 35Cl, 79Br], 485 [(M+H)+, 37Cl, 79Br or 35Cl, 81Br], 487 [(M+H)+, 37Cl, 81Br].

Preparation of [2-(7-bromo-isoquinole-5-sulfonylamino)-ethyl]-[2-(4-chloro-phenoxy)-ethyl]-carbamic acid tert-butyl ester Di-tert-butyl dicarbonate (0.398 g, 1.83 mmol) is added to a stirred solution of 7-bromo-isoquinoline-5-sulfonic acid {2-[2-(4-chloro-phenoxy)-ethylamino]-ethyl}-amide (0.590 g, 1.22 mmol) in anhydrous methylene chloride (10 mL). The mixture is allowed to stir at ambient temperature for 16 hours. After concentration and MPLC separation on silica (gradient 0-3% methanol in methylene chloride), 0.669 g (94% yield) of the title compound is obtained as a white foam. ESIMS: m/z 584 [(M+H)+, 35Cl, 79Br], 586 [(M+H), 37C, 79Br or 35Cl, 81Br], 588 [(M+H)+, 37Cl, 81Br].

Preparation 113

Preparation of {2-[(7-bromo-isoquinoline-5-sulfonyl)-methyl-amino]-ethyl}-[2-(4-chloro-phenoxy)-e-carbamic acid tert-butyl ester

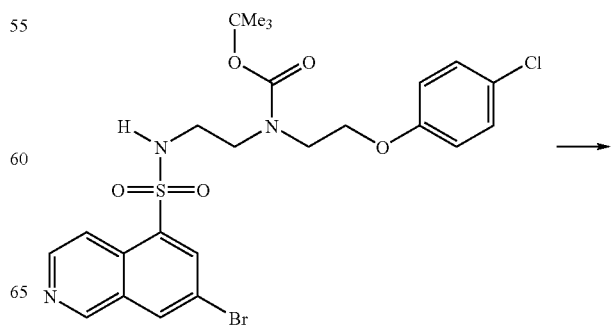

31

-continued

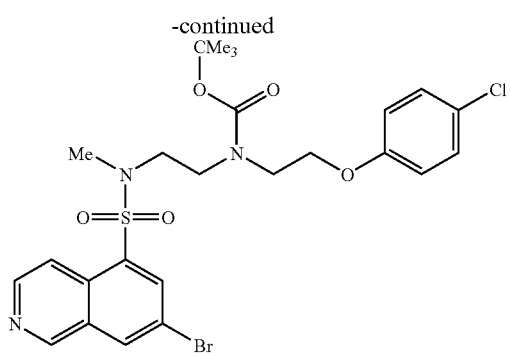

32

Methyl iodide (0.031 mL, 0.50 mmol) is added to a stirred solution of [2-(7-bromo-isoquinoline-5-sulfonylamino)-ethyl]-[2-(4-chloro-phenoxy)-ethyl]-carbamic acid tert-butyl ester (147 mg, 0.252-mmol) and potassium carbonate (87 mg, 0.63 mmol) in anhydrous DMF (2 mL). The mixture is stirred for 20 minutes. After usual work up and MPLC separation, the title compound is obtained as oil. ESIMS: m/z 598 [(M+H)$^+$, $^{35}$Cl, $^{79}$Br], 600 [(M+H)$^+$, $^{37}$Cl, $^{79}$Br or $^{35}$Cl, $^{81}$Br], 602 [(M+H)$^+$, $^{37}$Cl, $^{81}$Br].

Preparation 114

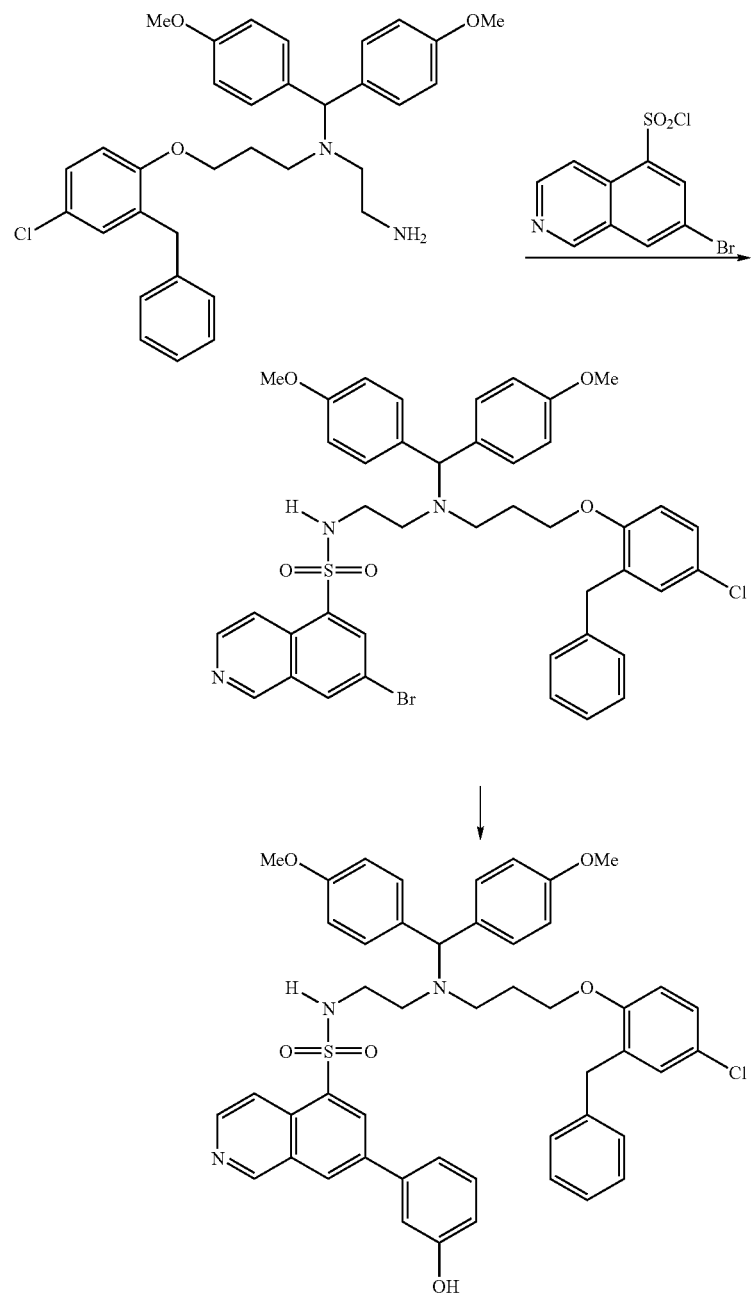

Preparation of 7-bromo-isoquinoline-5-sulfonic acid (2-{[3-(2-benzyl-4-chloro-phenoxy)-propyl]-[bis-(4-methoxy-phenyl)-methyl]-amino}-ethyl)-amide

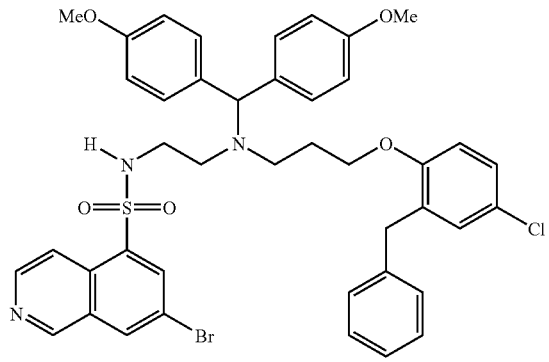

Using a procedure analogous to Preparation 103, reaction of 7-bromo-isoquinoline -5-sulfonyl chloride with $N^1$-[3-(2-benzyl-4-chloro-phenoxy)-propyl]-$N^1$-[bis-(4-methoxy-phenyl)-methyl]-ethane-1,2-diamine provides the title compound as a foam. ESIMS: m/z 814[(M+H)$^+$, $^{35}$Cl, $^{79}$Br], 816 [(M+H)$^+$, $^{37}$Cl, $^{79}$Br or $^{35}$Cl, $^{81}$Br], 818 [(M+H)$^+$, $^{37}$Cl, $^{81}$Br].

Preparation of 7-(3-hydroxy-phenyl)-isoquinoline-5-sulfonic acid (2-{[3-(2-benzyl-4-chloro-phenoxy)-propyl]-[bis-(4-methoxy-phenyl)-methyl]-amino}-ethyl)-amide

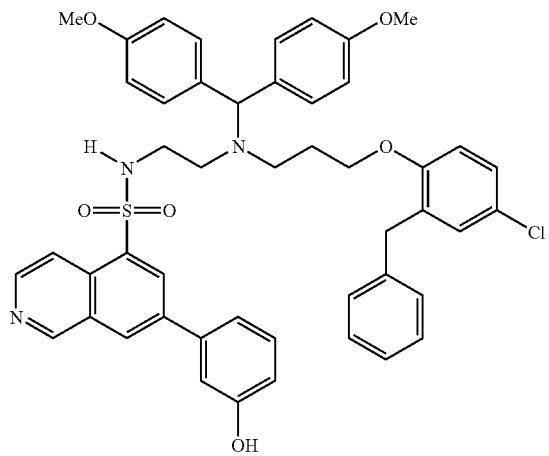

Using a procedure analogous to the preparation of Example 140, with 7-bromo-isoquinoline -5-sulfonic acid (2-{[3-(2-benzyl-4-chloro-phenoxy)-propyl]-[bis-(4-methoxy-phenyl)-methyl]-amino}-ethyl)-amide as starting material, the title compound is obtained as oil. ESIMS: m/z 828 [(M+H)$^+$, $^{35}$Cl], 830 [(M+H)$^+$, $^{37}$Cl].

Preparation 115

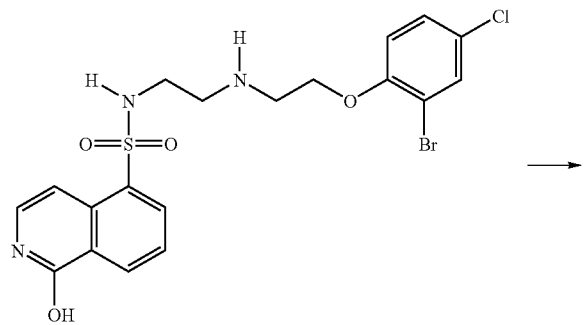

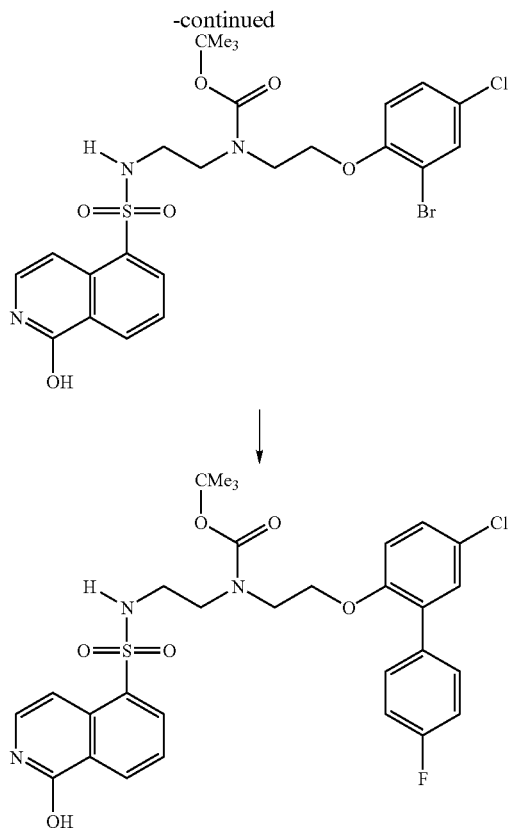

Preparation of [2-(2-bromo-4-chloro-phenoxy)-ethyl]-[2-(1-hydroxy-isoquinoline-5-sulfonylamino)-ethyl]-carbamic acid tert-butyl ester

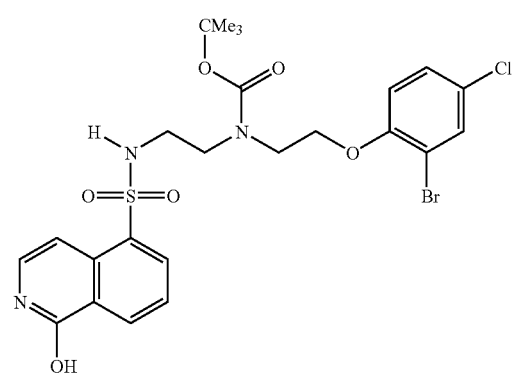

Di-tert-butyl dicarbonate (0.199 g, 0.958 mmol) is added to a stirred solution of 1-hydroxy-isoquinoline-5-sulfonic acid {2-[2-(2-bromo-4-chloro-phenoxy)-ethylamino]ethyl}-amide (0.457 g, 0.912 mmol) in anhydrous methylene chloride (10 mL)/methanol (10 mL). The mixture is allowed to stir at ambient temperature for 4 hours. After concentration and MPLC separation on silica (gradient 0-10% methanol in methylene chloride), 0.500 g (91% yield) of the title compound is obtained. ESIMS: m/z 600 [(M+H)$^+$, $^{35}$Cl, $^{79}$Br], 602 [(M+H)$^+$, $^{37}$Cl, $^{79}$Br or $^{35}$Cl, $^{81}$Br], 604 [(M+H)$^+$, $^{37}$Cl, $^{81}$Br].

Preparation of [2-(5-chloro-4'-fluoro-biphenyl-2-yloxy)-ethyl]-[2-(1-hydroxy-isoquinoline-5-sulfonylamino)-ethyl]-carbamic acid tert-butyl ester

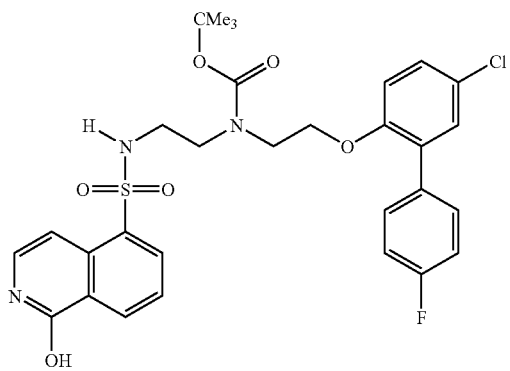

Using a procedure analogous to the preparation of Example 136, with [2-[2-bromo-4-chloro-phenoxy)-ethyl]-(2-(1-hydroxy-isoquinoline-5-sulfonylamino)-ethyl]-carbamic acid tert-butyl ester as starting material, the title compound is obtained as white foam. ESIMS: m/z 616 [(M+H)$^+$, $^{35}$Cl], 618 [(M+H)$^+$, $^{37}$Cl].

Preparation 116

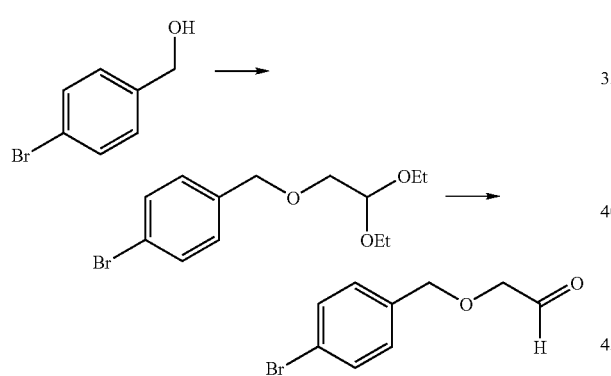

Preparation of 1-Bromo-4-(2,2-diethoxy-ethoxymethyl)-benzene

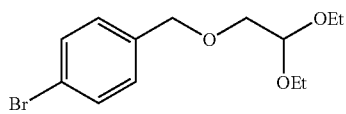

Sodium bis(trimethylsilyl)amide (12.1 mL, 1 N in THF) is added to a stirred solution of 4-bromo-benzylalcohol (2.05 g, 11.0 mmol) in dry DMF (7 mL) at ambient temperature. The mixture is stirred for 5 min before it is treated with bromoacetaldehyde diethyl acetal (1.99 mL, 13.2 mmol). The resultant mixture is allowed to stir at ambient temperature for 20 hours. Ethyl acetate (60 mL) and water (60 mL) are added to the mixture. The organic layer is separated, washed with half-saturated brine, dried, filtered and concentrated. After MPLC separation on silica (gradient 0-8% ethyl acetate in hexane), 1.86 g (56% yield) title compound is obtained as colorless oil.

Preparation of (4-Bromo-benzyloxy)-acetaldehyde

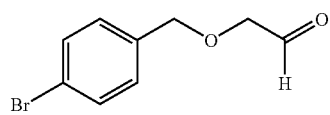

5 N HCl (20 mL) is added to a stirred solution of 1-bromo 4-(2,2-diethoxy-ethoxymethyl)-benzene (1.86 g, 6.13 mmol) in diethyl ether (20 mL) at ambient temperature. The resultant two-layered mixture is stirred vigorously under nitrogen for 16 hours. Diethyl ether (30 mL) and brine (20 mL) are added to the mixture. The organic layer is separated, washed with half-saturated brine, dried, filter and concentrated into a ~50 mL solution (35 mg/mL). $^1$H NMR (CDCl$_3$): δ9.72 (s, 1H), 7.49 (d, J=7.49 Hz, 2H), 7.24 (d, J=7.9 Hz, 2H), 4.57 (s, 2H), 4.11 (s, 2H).

Preparation 117

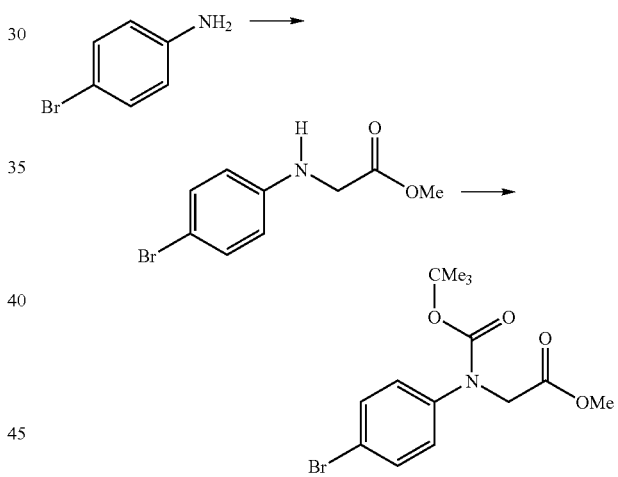

Preparation of (4-bromo-phenylamino)-acetic acid methyl ester

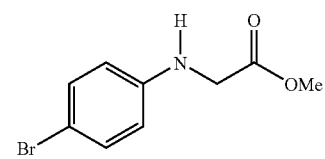

Potassium carbonate (2.41 g, 17.4 mmol) is added to a stirred solution of 4-bromo-aniline (2.00 g, 11.6 mmol) and methyl bromoacetate (1.78 g, 11.6 mmol) in dry DMF (20 mL) at ambient temperature. The mixture is heated at 100° C. for 1 hour. At ambient temperature ethyl acetate (60 mL) and water (60 mL) are added to the mixture. The organic layer is separated, washed with half-saturated brine, dried, filtered and concentrated. After MPLC separation on silica (gradient 0-15% ethyl acetate in hexane), 0.94 g (33% yield) of the title compound is obtained. $^1$H NMR (DMSO-d6): δ3.62 (s, 3H), 3.87 (d, J=6.4 Hz, 2H), 6.22 (t, J=6.4 Hz, 1H), 6.49 (d, J=8.8 Hz, 2H), 7.19 (d, J=8.8 Hz, 2H).

Preparation of [(4-bromo-phenyl)-tert-butoxycarbonyl-amino]-acetic acid methyl ester

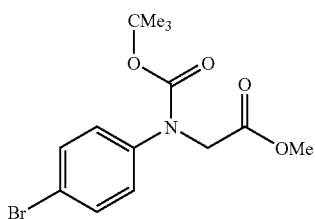

Di-tert-butyl dicarbonate (3 g) is added to a stirred solution of (4-bromo-phenylamino)-acetic acid methyl ester (1.02 g, 4.18 mmol) and 4-dimethylamino-pyridine (0.510 g, 4.18 mmol) in dry 1,4-dioxane (10 mL). The mixture is heated at 100° C. for 1.5 hours. After concentration and MPLC separation on silica (gradient 0-15% ethyl acetate in hexane), 1.21 g (84% yield) of the title compound is obtained. $^1$H NMR (CDCl$_3$): δ1.42 (s, 9H), 3.76 (s, 3H), 4.26 (s, 2H), 7.17 (br d, J=8.4 Hz, 2H), 7.44 (d, J=8.4 Hz, 2H)

Preparation 118

Synthesis of Amides

General procedure

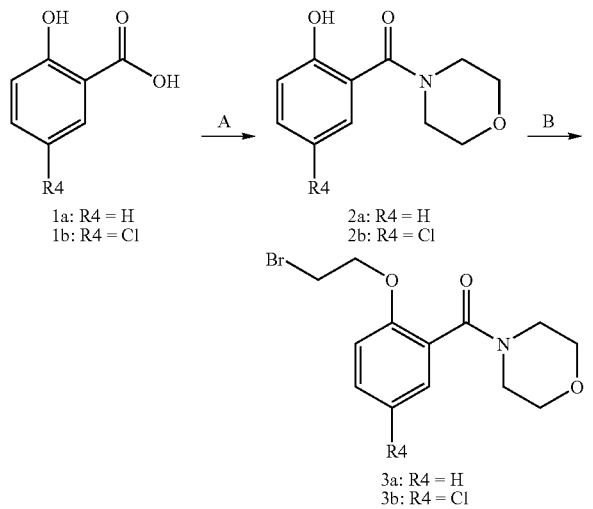

Step A

Synthesis of substituted (2-Hydroxyphenyl)morpholin-4-yl-methanones (2)

To a solution of the corresponding salicilic acid 1a, 1b (36.2 mmol) and morpholine (4.73 mL, 54.3 mmol) in DMF (70 mL), EDCI (10.42 g, 54.3 mmol), 1-hydroxybenzotriazole hydrate (HOBt) (7.33 g, 54.3 mmol), and triethylamine (7.62 mL, 54.3 mmol) were added. The reaction mixture was stirred at room temperature under argon for 2 days, and then quenched by addition of HCl 1N (50 mL). The mixture was extracted with EtOAc (2×100 mL), washed with saturated aqueous NaHCO$_3$ solution and dried over MgSO$_4$. The solvent was evaporated and the crude product 2a, 2b was used in the next step without further purification (45-70% yield).

Step B

Synthesis of substituted [2-(2-Bromoethoxy)phenyl]morpholin-4-yl-methanones (3)

Powdered K$_2$CO$_3$ (2.0 g, 14.5 mmol) was added to a stirred solution of the corresponding phenol 2a, 2b (7.25 mmol) and 1,2-dibromoethane (1.88 mL, 21.7 mmol) in anhydrous DMF (20 mL) at room temperature under argon. The mixture was heated at 80° C. overnight, cooled to room temperature, quenched by addition of water and extracted with EtOAc (2×50 mL). The organic layer was dried over MgSO$_4$ and the solvent was evaporated. The crude product 3a, 3b urified by flash chromatography in silica gel, eluent CH$_2$Cl$_2$/acetone 96:4 (25-45% yield).

Step C

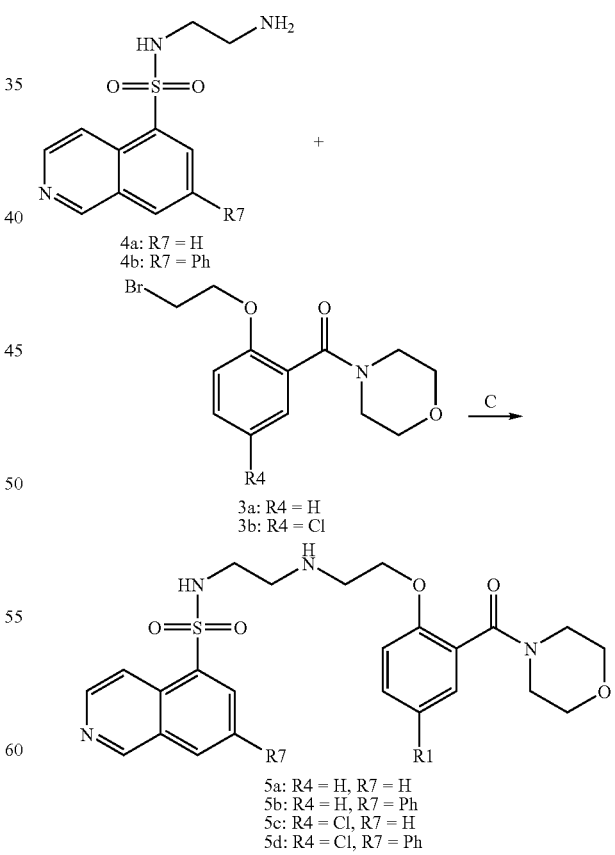

To a stirred solution of the corresponding bromo-derivative 3a, 3b (0.66 mmol) and diisopropylethylamine (345 μL, 1.98 mmol) in anhydrous 1,4-dioxane (2 mL) and MeOH (1 mL), the corresponding isoquinoline-derivative 4a, 4b (0.66 mmol) was added at room temperature under argon. The mixture was heated at 95°° C. overnight. After cooling to room temperature the reaction was quenched by addition of EtOAc (10 mL) and half-saturated aqueous NaHCO₃ solution (10 mL). The organic layer was separated, dried over MgSO₄ and concentrated. The crude product 5a, 5b, 5c, 5d was purified by flash column in silica gel, eluent: CH₂Cl₂/CH₃OH 96:4 (20-55% yield).

(All the morpholine amide targets were sent as free bases, except 5d that was converted in its corresponding dihydrochloride salt by treatment with 4 M HCl in dioxane).

Preparation 119

Synthesis of Amines

General procedure

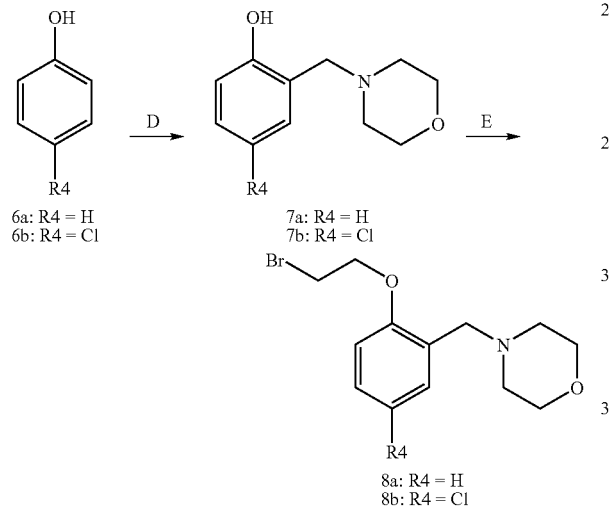

6a: R4 = H
6b: R4 = Cl

7a: R4 = H
7b: R4 = Cl

8a: R4 = H
8b: R4 = Cl

Step D

Synthesis of Substituted (2-Hydroxybenzyl)morpholines (7)

A solution of paraformaldehyde (3.24 g, 108 mmol) and morpholine (9.40 mL, 108 mmol) in ethanol (40 mL) was stirred at room temperature for 30 minutes, and then a solution of the corresponding phenol 6a, 6b (106 mmol) in 20 mL of ethanol was added and the mixture was refluxed overnight. After cooling, the solvent was evaporated, and the crude product 7a, 7b was purified by chromatography in silica gel, eluent hexane/EtOAc 9:1 (40-65% yield).

Step E

Synthesis of substituted 4-[2-(2-Bromoethoxy)benzyl]morpholines (8)

To a solution of the corresponding phenol (12.9 mmol) and tetrabutylammonium iodide (478 mg, 1.29 mmol) in THF (25 mL) at room temperature, NaH (60% in oil, 0.77 g, 19.4 mmol) was slowly added. The mixture was stirred for 30 minutes, and then 1,2-dibromoethane (3.36 mL, 38.8 mmol) was added. The mixture was stirred at room temperature under argon overnight. Water was added (50 mL) and the mixture was extracted with EtOAc (2×50 mL). The organic layer was dried over MgSO₄ and concentrated. The crude product 8a, 8b was purified by chromatography in silica gel, eluent hexane/EtOAc 6:1 (16-25% yield).

Step F

Coupling Reaction

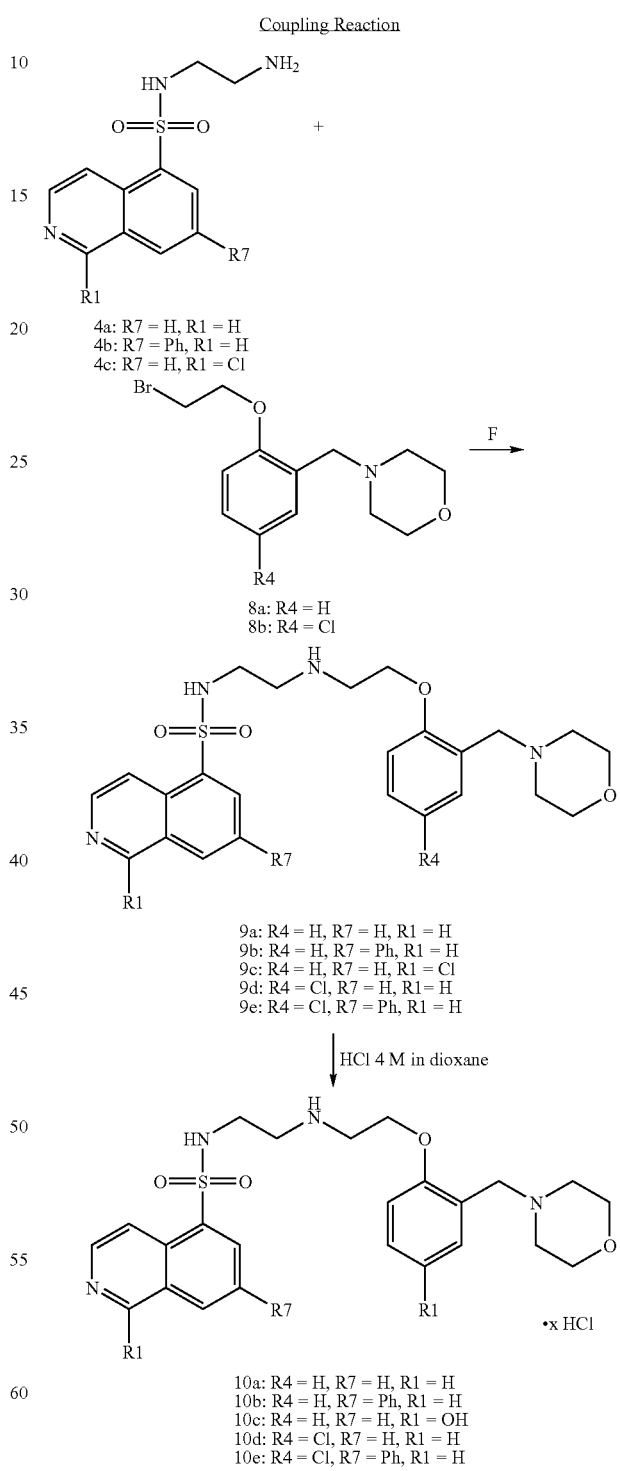

4a: R7 = H, R1 = H
4b: R7 = Ph, R1 = H
4c: R7 = H, R1 = Cl

8a: R4 = H
8b: R4 = Cl

9a: R4 = H, R7 = H, R1 = H
9b: R4 = H, R7 = Ph, R1 = H
9c: R4 = H, R7 = H, R1 = Cl
9d: R4 = Cl, R7 = H, R1 = H
9e: R4 = Cl, R7 = Ph, R1 = H

HCl 4 M in dioxane

10a: R4 = H, R7 = H, R1 = H
10b: R4 = H, R7 = Ph, R1 = H
10c: R4 = H, R7 = H, R1 = OH
10d: R4 = Cl, R7 = H, R1 = H
10e: R4 = Cl, R7 = Ph, R1 = H

To a stirred solution of the corresponding bromo-derivative 8a, 8b (0.70 mmol) and the corresponding isoquinoline-derivative 4a, 4b, 4c (0.70 mmol) in anhydrous 1,4-dioxane (2 mL) and MeOH (1 mL), triethylamine (295 µL, 2.1 mmol) was added at room temperature under argon. The mixture was heated at 95° C. overnight. After cooling to room temperature the reaction was quenched by addition of EtOAc (10 mL) and half-saturated aqueous NaHCO$_3$ solution (10 mL). The organic layer was separated, dried over MgSO$_4$ and concentrated. The crude product 9a, 9b, 9c, 9d, 9e was purified by flash column in silica gel, eluent: CH$_2$Cl$_2$/CH$_3$OH 96:4 (20-55% yield).

The corresponding hydrochloride salts 10a,b,d,e were obtained by treatment of 9a,b,d,e with HCl 4 M in dioxane at room temperature for 30 minutes. The solvent was evaporated and the salts were washed several times with Et$_2$O and dried.

10c was obtained by addition of a 6 N solution of HCl in water to a solution of 9c in THF at room temperature. The mixture was heated at 65° C. overnight, concentrated, washed several times with Et$_2$O and dried.

EXAMPLES

Example 1

Isoquinoline-5-sulfonic acid {2-[2-(2-bromo-phenoxy)-ethylamino]-ethyl}-amide di-hydrochloride

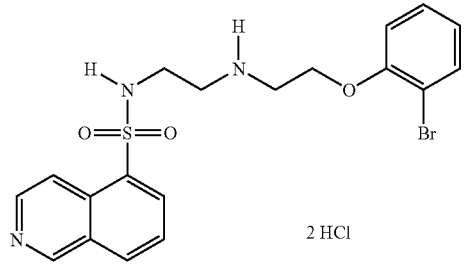

Diisobutylaluminum hydride (DIBAL-H, 1.0M in toluene, 8.32 mL) is added dropwise to a stirred solution of (2-bromo-phenoxy)-acetic acid methyl ester (1.70 g, 6.94 mmol) in anhydrous CH$_2$Cl$_2$ (15 mL) at −78° C. under nitrogen. The resultant solution is stirred at −78° C. for 1 hour. Methanol (2 mL) is added dropwise to the mixture, followed by the addition of Et$_2$O (25 mL). Cold bath is removed, and a 2.5N HCl solution (33 mL) is added in small portions to the cold mixture. The resultant two-layered solution is allowed to stir vigorously at ambient temperature for 1 hour. Ethyl ether (50 mL) and saturated aqueous NaCl solution (30 mL) are added to the mixture. The organic layer is separated, dried over MgSO$_4$, filtered and concentrated at ambient temperature to give 1.50 g of a ~50:50 mixture of (2-bromo-phenoxy)-acetaldehyde and its methyl hemiacetal as oil. The oil is diluted in Et$_2$O to form a stock solution (80 mg/mL), which is used for the subsequent reaction. $^1$H NMR (CDCl$_3$) ((2-bromo-phenoxy)-acetaldehyde): δ3.52 (s, 2H), 9.90 (s, 1H); (methyl hemiacetal): δ3.48 (s, 1H), 4.05 and 4.10 (br AB, J=9.6 Hz, 2H), 4.62 (s, 3H), 4.91 (br s, 1H).

A 5.3 mL of the above stock solution (~1.9 mmol) is added to a stirred mixture of 4 Å molecular sieve (600 mg) and isoquinoline-5-sulfonic acid (2-amino-ethyl)-amide (228 mg, 0.907 mmol) in anhydrous CH$_3$OH (5 mL) at ambient temperature under nitrogen. The resultant mixture is stirred for 16 hours. Then the mixture is cooled to 0° C. and treated with powdered sodium borohydride (75 mg, 2.0 mmol). The mixture is allowed to stir at 0° C. for 1 hour, then at ambient temperature for another 1 hour. After filtration and subsequent concentration in vacuo, the crude product is chromatographed on silica (gradient 5-25% CH$_3$OH in EtOAc) to give 341 mg (0.757 mmol, 83% yield) of the free amine product as oil. The free amine (338 mg, 0.751 mmol) is dissolved in EtOAc (15 mL) and treated dropwise with 1N HCl/Et$_2$O solution (2.25 mL) with stirring under nitrogen. The resultant white suspension is stirred for 15 minutes, filtered and dried under vacuum at 60° C. to give 375 mg (0.717 mmol, 95% yield) of the title compound as a hygroscopic white powder. ESIMS: m/z 450 [(M+H)$^+$, $^{79}$Br], 452 [(M+H)$^+$, $^{81}$Br].

Using a procedure similar to that described in Example 1 and the appropriate starting materials, the following compounds, prepared as di-hydrochloride salts, may be synthesized and isolated.

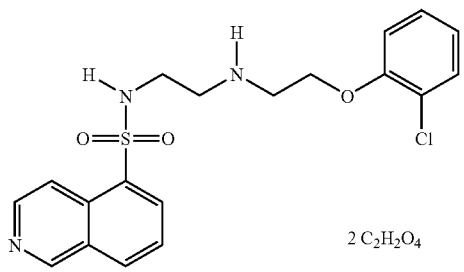

2 HCl

| Ex. # | R$^6$ | Data |
|---|---|---|
| 2 | 2-trifluoromethyl | ESIMS: m/z 440 (M + H)$^+$. Analysis for C$_{20}$H$_{22}$F$_3$Cl$_2$N$_3$O$_3$S·0.8H$_2$O: calcd: C, 45.60; H, 4.52; N, 7.98; found: C, 45.53; H, 4.27; N, 7.88. |
| 3 | 2-methoxy | ESIMS: m/z 402 (M + H)$^+$. |
| 4 | 3-bromo | ESIMS: m/z 450 [(M + H)$^+$, $^{79}$Br], 452 [(M + H)$^+$, $^{81}$Br]. |
| 5 | 3-methyl | ESIMS: m/z 386 (M + H)$^+$. |
| 6 | 3-trifluoromethyl | ESIMS: m/z 440 (M + H)$^+$. |
| 7 | 3-phenyl | ESIMS: m/z 448 (M + H)$^+$. |
| 8 | 3-methoxy | ESIMS: m/z 402 (M + H)$^+$. |
| 9 | 4-fluoro | ESIMS: m/z 390 (M + H)$^+$. |
| 10 | 4-bromo | ESIMS: m/z 450 [(M + H)$^+$, $^{79}$Br], 452 [(M + H)$^+$, $^{81}$Br]. |
| 11 | 4-iodo | ESIMS: m/z 498 (M + H)$^+$. |
| 12 | 4-trifluoromethyl | ESIMS: m/z 440 (M + H)$^+$. |
| 13 | 4-phenyl | ESIMS: m/z 448 (M + H)$^+$. |
| 14 | 4-nitro | ESIMS: m/z 417 (M + H)$^+$. |
| 15 | 4-methoxy | ESIMS: m/z 417 (M + H)$^+$. |
| 16 | 4-phenoxy | ESIMS: m/z 464 (M + H)$^+$. |

Example 17

Isoquinoline-5-sulfonic acid {2-[2-(2-chloro-phenoxy)-ethylamino]-ethyl}-amide di-oxalic acid By following the procedure as described in Example 1, DIBAL-H reduction of (2-chloro-phenoxy)-acetic acid methyl ester and subsequent reductive amination with isoquinoline-5-sulfonic acid (2-amino-ethyl)-amide (175 mg, 0.696 mmol) give 183 mg (0.451 mmol, 65% yield) of the free amine product as oil. The free amine is dissolved in EtOAc (10 mL) and treated dropwise with an EtOAc solution (10 mL) containing oxalic acid dihydrate (114 mg, 0.902 mmol) with stirring under nitrogen. The white suspension is stirred for 15 minutes, filtered and dried under vacuum at 60° C. to give 220 mg (0.375 mmol, 83% yield) of the title compound as a white powder. ESIMS: m/z 406 [(M+H)$^+$, $^{35}$Cl], 408 [(M+H)$^+$, $^{37}$Cl]. Analysis for $C_{19}H_{20}ClN_3O_3S \cdot 1.8C_2H_2O_4$: calcd: C, 47.79; H, 4.19; N, 7.40; found: C, 47.70; H, 4.03; N, 7.45.

Using a procedure similar to Example 17, with the appropriate starting materials, the following compounds may be prepared as di-oxalic acid salts.

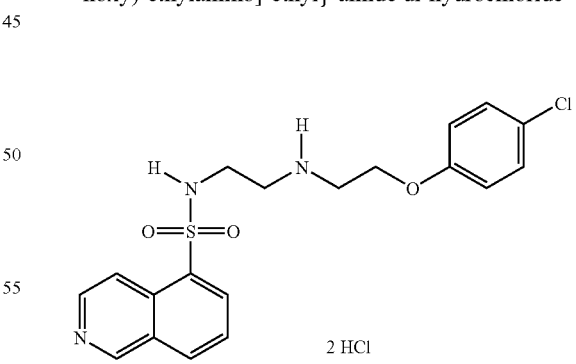

2 $C_2H_2O_4$

| Ex. # | R$^6$ | Data |
|---|---|---|
| 18 | 2-methyl | ESIMS: m/z 386 (M + H)$^+$. Analysis for $C_{20}H_{23}N_3O_3S \cdot 1.8C_2H_2O_4$: calcd: C, 51.77; H, 4.90; N, 7.67; found: C, 51.74; H, 4.81; N, 7.79. |
| 19 | 2-tert-butyl | ESIMS: m/z 428 (M + H)$^+$. |
| 20 | 2-methyl-propen-3-yl | ESIMS: m/z 426 (M + H)$^+$. |
| 21 | 2-phenyl | ESIMS: m/z 448 (M + H)$^+$. |
| 22 | 2-benzyl | ESIMS: m/z 462 (M + H)$^+$. |
| 23 | 2-(4-methyl-benzyl) | ESIMS: m/z 476 (M + H)$^+$. |
| 24 | 2-(4-methoxy-benzyl) | ESIMS: m/z 492 (M + H)$^+$. |
| 25 | 2-phenethyl | ESIMS: m/z 476 (M + H)$^+$. |
| 26 | 2-phenoxy | ESIMS: m/z 464 (M + H)$^+$. |
| 27 | 3-chloro | ESIMS: m/z 406 [(M + H)$^+$, $^{35}$Cl], 408 [(M + H)$^+$, $^{37}$Cl]. |
| 28 | 3-benzyl | ESIMS: m/z 462 (M + H)$^+$. |
| 29 | 4-methyl | ESIMS: m/z 384 (M − H)$^-$. Analysis for $C_{24}H_{27}N_3O_{11}S$: calcd: C, 50.97; H, 4.81; N, 7.43; found: C, 51.10; H, 4.68; N, 7.58. |
| 30 | 4-benzyl | ESIMS: m/z 462 (M + H)$^+$. |

Example 31

Isoquinoline-5-sulfonic acid {2-[2-(2-(phenoxy)-ethylamino]-ethyl}-amide di-hydrochloride

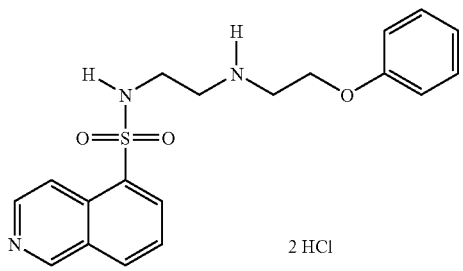

2 HCl

Diisobutylaluminum hydride (DIBAL-H, 1.0M in toluene, 20.0 mL) is added dropwise to a stirred solution of phenoxy-acetonitrile (2.22 g, 16.7 mmol) in anhydrous $CH_2Cl_2$ (18 mL) at −78° C. under nitrogen. The resultant solution is allowed to stir at 0° C. for 1 hour. Methanol (2 mL) is added dropwise to quench excess of DIBAL-H, followed by the successive addition of $Et_2O$ (40 mL) and 2N HCl (60 mL) in small portions to the cold mixture. The resultant two-layered solution is allowed to stir vigorously at ambient temperature for 1 hour. Ethyl ether (30 mL) and saturated aqueous NaCl solution (30 mL) are added to the mixture. The organic layer is separated, dried over $MgSO_4$, filtered and concentrated at ambient temperature to give 2.27 g of the crude phenoxyacetaldehyde as oil. The oil is diluted in $Et_2O$ to form a stock solution (60 mg/mL), which is used for the subsequent reaction. $^1$H NM (CDCl$_3$): δ4.57 (s, 2H), 9.87 (s, 1H).

A 6.06 mL of the above stock solution (~1.1 mmol) is added to a stirred mixture of 4 Å molecular sieve (600 mg) and isoquinoline-5-sulfonic acid (2-amino-ethyl)-amide (244 mg, 0.971 mmol) in anhydrous $CH_3OH$ (5 mL), and the resultant mixture is stirred at ambient temperature for 16 hours. The mixture is cooled to 0° C. before it is treated with powdered sodium borohydride (81 mg, 2.1 mmol). The mixture is stirred at 0° C. for 1 hour then at ambient temperature for another 1 hour. After filtration and subsequent concentration in vacuo, the crude product is chromatographed on silica (gradient 5-30% $CH_3OH$ in EtOAc) to give 156 mg (0.420 mmol, 43% yield) of the free amine product as oil. The free amine (154 mg, 0.415 mmol) is dissolved in EtOAc (15 mL) and treated dropwise with 1N HCl/$Et_2O$ solution (1.24 mL) with stirring under nitrogen. The white suspension is stirred for 15 minutes, filtered and dried under vacuum at 60° C. to give 177 mg (0.398 mmol, 96% yield) of the title compound as a hygroscopic white powder. ESIMS: m/z 372 (M+H)$^+$.

Example 32

Isoquinoline-5-sulfonic acid {2-[2-(4-chloro-phenoxy)-ethylamino]-ethyl}-amide di-hydrochloride 2 HCl By following similar procedure as described in Example 31, DIBAL-H reduction of (4-chloro-phenoxy)-acetonitrile and subsequent reductive amination with isoquinoline-5-sulfonic acid (2-amino-ethyl)-amide gives the free amine product as oil. The free amine is converted to the di-hydrochloride salt of the title compound as a hygroscopic white powder. ESIMS: m/z 406 [(M+H)$^+$, $^{35}$Cl], 408 [(M+H)$^+$, $^{37}$Cl].

Example 33

Isoquinoline-5-sulfonic acid {2-[2-(4-cyano-phenoxy)-ethylamino]-ethyl}-amide di-hydrochloride

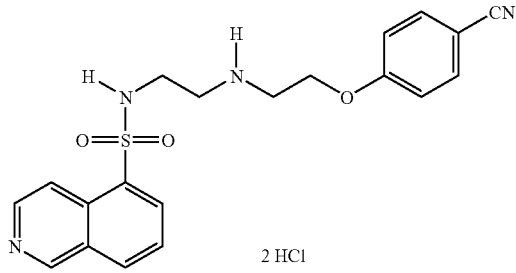

2 HCl

A 5N HCl (25 mL) solution is added to a stirred solution of 4-(2,2-diethoxy-ethoxy)-benzonitrile (2.00 g, 8.50 mmol) in Et$_2$O (25 mL). The two-layered solution is stirred vigorously at ambient temperature under nitrogen for 24 hours. Another 50 mL Et$_2$O is added to the mixture. The organic layer is separated, washed with an aqueous solution (30 mL) containing saturated NaHCO$_3$ (0.5 mL), dried over MgSO$_4$, filtered and concentrated at ambient temperature to give 1.36 g of the crude (4-cyano-phenoxy)acetaldehyde as oil. The oil is diluted in Et$_2$O to form a stock solution (25 mg/mL), which is used for the subsequent reaction. $^1$H NM (CDCl$_3$): δ4.66 (s, 2H), 9.85 (s, 1H).

A 16.8 mL of the above stock solution (~1.2 mmol) is added to a stirred mixture of 4 Å molecular sieve (600 mg) and isoquinoline-5-sulfonic acid (2-amino-ethyl)-amide (245 mg, 0.975 mmol) in anhydrous CH$_3$OH (8 mL) and the resultant mixture is stirred at ambient temperature for 16 hours. The mixture is cooled to 0° C. before it is treated with powdered sodium borohydride (81 mg, 2.1 mmol). The mixture is stirred at 0° C. for 1 hour then at ambient temperature for another 1 hour. After filtration and subsequent concentration in vacuo, the crude product is chromatographed on silica (gradient 5-30% CH$_3$OH in EtOAc) to give 328 mg (0.827 mmol, 85% yield) of the free amine product as oil. The free amine (290 mg, 0.731 mmol) is dissolved in CH$_2$Cl$_2$ (25 mL) and treated dropwise with 1N HCl/Et$_2$O solution (2.19 mL) with stirring under nitrogen. The white suspension is stirred for 15 minutes, filtered and dried under vacuum at 60° C. to give 300 mg (0.639 mmol, 87% yield) of the title compound as a hygroscopic white powder. ESIMS: m/z 397 (M+H)$^+$.

Example 34

Isoquinoline-5-sulfonic acid {2-[2-(2,4-dichloro-phenoxy)-ethylamino]-ethyl}-amide di-hydrochloride

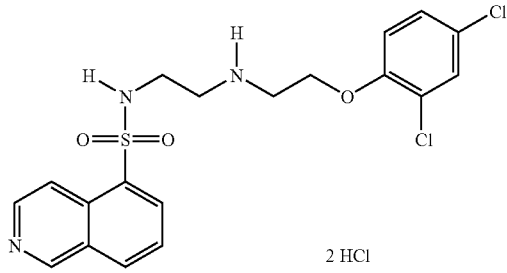

2 HCl

Diisobutylaluminum hydride (1.0M in toluene, 8.83 mL) is added dropwise to a stirred solution of (2,4-dichloro-phenoxy)-acetic acid methyl ester (1.73 g, 7.36 mmol) in anhydrous CH$_2$Cl$_2$ (15 mL) at −78° C. under nitrogen. The resultant solution is stirred at −78° C. for 1 hour. Methanol (2 mL) is added dropwise to the mixture, followed by the addition of Et$_2$O (25 mL). The cold bath is removed, and a 5N HCl solution (18 mL) is added in small portions to the cold mixture. The resultant two-layered solution is allowed to stir vigorously at ambient temperature for 1 hour. Ethyl ether (30 mL) and saturated aqueous NaCl solution (10 mL) are added to the mixture. The organic layer is separated, dried over MgSO$_4$, filtered and concentrated at ambient temperature to give 1.62 g of a ~50:50 mixture of (2,4-dichloro-phenoxy)-acetaldehyde and its methyl hemiacetal as oil. The oil is diluted in CH$_2$Cl$_2$ to form a stock solution (65 mg/m), which is used for the subsequent reaction. $^1$H NMR (CDCl$_3$) ((2,4-dichloro-phenoxy)-acetaldehyde): δ3.52 (s, 2H), 9.88 (s, 1H); (methyl hemiacetal): δ3.48 (s, 1H), 4.05-4.15 (m, 2H), 4.61 (s, 3H), 4.90 (br s, 1H).

A 5.3 mL of the above stock solution (~0.67 mmol) is added to a stirred mixture of 4 Å molecular sieve (300 mg) and isoquinoline-5-sulfonic acid (2-amino-ethyl)-amide (152 mg, 0.605 mmol) in anhydrous CH$_3$OH (4 mL), and the resultant mixture is stirred for 16 hours. The mixture is cooled to 0° C. before it is treated with powdered sodium borohydride (50 mg, 1.3 mmol). The mixture is stirred at 0° C. for 1 hour then at ambient temperature for another 1 hour. After filtration and subsequent concentration in vacuo, the crude product is chromatographed on silica (gradient 5-25% CH$_3$OH in EtOAc) to give 234 mg (0.531 mmol, 88% yield) of the free amine product as oil. The free amine (231 mg, 0.525 mmol) is dissolved in EtOAc (15 mL) and treated dropwise with 1N HCl/Et$_2$O solution (1.57 mL) with stirring under nitrogen. The white suspension is stirred for 15 minutes, filtered and dried under vacuum at 60° C. to give 244 mg (0.475 mmol, 91% yield) of the title compound as a white powder. ESIMS: m/z 440 [(M+H)$^+$, $^{35}$Cl, $^{35}$Cl], 442 [(M+H)$^+$, $^{35}$Cl, $^{37}$Cl], 444 [(M+H)$^+$, $^{37}$Cl, $^{37}$Cl].

Using a method similar to Example 34, with the appropriate starting materials, the following compounds may be prepared as dihydrochloride salts.

| Ex. # | R$^5$ | R$^6$ | Data |
|---|---|---|---|
| 35 | 4-chloro | 2-methyl | ESIMS: m/z 420 [(M + H)$^+$, $^{35}$Cl], 422 [(M + H)$^+$, $^{37}$Cl]. |
| 36 | 4-chloro | 2-(propen-3-yl) | ESIMS: m/z 446 [(M + H)$^+$, $^{35}$Cl], 448 [(M + H)$^+$, $^{37}$Cl]. |
| 37 | 4-chloro | 2-propyl | ESIMS: m/z 448 [(M + H)$^+$, $^{35}$Cl], 450 [(M + H)$^+$, $^{37}$Cl]. |
| 38 | 4-chloro | 2-cyclohexyl | ESIMS: m/z 488 [(M + H)$^+$, $^{35}$Cl], 490 [(M + H)$^+$, $^{37}$Cl]. |
| 39 | 4-chloro | 2-benzyl | ESIMS: m/z 496 [(M + H)$^+$, $^{35}$Cl], 498 [(M + H)$^+$, $^{37}$Cl]. |

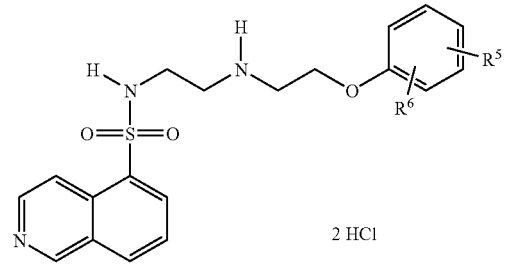

2 HCl

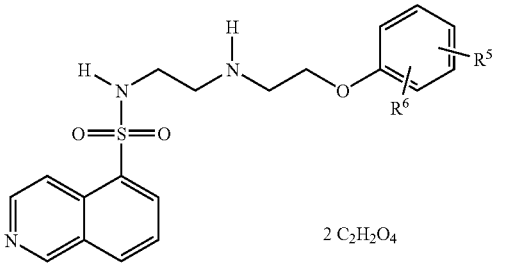

2 C$_2$H$_2$O$_4$

| Ex. # | R$^5$ | R$^6$ | Data |
|---|---|---|---|
| 40 | 4-chloro | 2-methoxy | ESIMS: m/z 436 [(M + H)$^+$, $^{35}$Cl], 438 [(M + H)$^+$, $^{37}$Cl]. |
| 41 | 4-bromo | 2-chloro | ESIMS: m/z 484 [(M + H)$^+$, $^{35}$Cl, $^{79}$Br], 486 [(M + H)$^+$, $^{35}$Cl, $^{81}$Br or $^{37}$Cl, $^{79}$Br], 488 [(M + H)$^+$, $^{37}$Cl, $^{81}$Br]. |
| 42 | 4-bromo | 2-bromo | ESIMS: m/z 528 [(M + H)$^+$, $^{79}$Br, $^{79}$Br], 530 [(M + H)$^+$, $^{79}$Br, $^{81}$Br], 532 [(M + H)$^+$, $^{81}$Br, $^{81}$Br]. |
| 43 | 4-bromo | 3-methyl | ESIMS: m/z 464 [(M + H)$^+$, $^{79}$Br], 466 [(M + H)$^+$, $^{81}$Br]. Analysis for C$_{20}$H$_{24}$BrCl$_2$N$_3$O$_3$S·0.5H$_2$O: calcd: C, 43.97; H, 4.61; N, 7.69; found: C, 44.00; H, 4.47; N, 7.52. |
| 44 | 4-bromo | 2-nitro | ESIMS: m/z 495 [(M + H)$^+$, $^{79}$Br], 482 [(M + H)$^+$, $^{81}$Br]. |
| 45 | 4-bromo | 2-methoxy | ESIMS: m/z 480 [(M + H)$^+$, $^{79}$Br], 482 [(M + H)$^+$, $^{81}$Br]. |
| 46 | 4-nitro | 2-chloro | ESIMS: m/z 451 [(M + H)$^+$, $^{35}$Cl], 453 [(M + H)$^+$, $^{37}$Cl]. |
| 47 | 4-chloro | 2-(3-methylsulfonyl-amino)-phenyl | ESIMS: m/z 575 [(M + H)$^+$, $^{35}$Cl], 577 [(M + H)$^+$, $^{37}$Cl]. |
| 49 | 4-chloro | 2-bromo | ESIMS: m/z 484 [(M + H)$^+$, $^{35}$Cl, $^{79}$Br], 486 [(M + H)$^+$, $^{37}$Cl, $^{79}$Br or $^{35}$Cl, $^{81}$Br], 488 [(M + H)$^+$, $^{37}$Cl, $^{81}$Br]. |
| 50 | 4-chloro | 2-(4-chloro-benzyl) | ESIMS: m/z 530 [(M + H)$^+$, $^{35}$Cl, $^{35}$Cl], 532 [(M + H)$^+$, $^{35}$Cl, $^{37}$Cl], 534 [(M + H)$^+$, $^{37}$Cl, $^{37}$Cl]. |
| 51 | 4-chloro | 2-(2,4-dichloro-benzyl) | ESIMS: m/z 564 [(M + H)$^+$, $^{35}$Cl, $^{35}$Cl, $^{35}$Cl], 566 [(M + H)$^+$, $^{35}$Cl, $^{35}$Cl, $^{37}$Cl], 568 [(M + H)$^+$, $^{35}$Cl, $^{37}$Cl, $^{37}$Cl], 570 [(M + H)$^+$, $^{37}$Cl, $^{37}$Cl, $^{37}$Cl]. |
| 52 | 4-chloro | 2-(isoxazol-5-yl) | ESIMS: m/z 473 [(M + H)$^+$, $^{35}$Cl], 475 [(M + H)$^+$, $^{37}$Cl]. |
| 53 | 4-chloro | 3-chloro | ESIMS: m/z 440 [(M + H)$^+$, $^{35}$Cl, $^{35}$Cl], 442 [(M + H)$^+$, $^{35}$Cl, $^{37}$Cl], 444 [(M + H)$^+$, $^{37}$Cl, $^{37}$Cl]. |
| 54 | 4-chloro | 3-methyl | ESIMS: m/z 420 [(M + H)$^+$, $^{35}$Cl], 422 [(M + H)$^+$, $^{37}$Cl]. Analysis for C$_{20}$H$_{22}$ClN$_3$O$_3$S·2C$_2$H$_2$O$_4$: calcd: C, 48.04; H, 4.37; N, 7.00; found: C, 48.24; H, 4.27; N, 7.33. |
| 55 | 4-chloro | 2-phenyl | ESIMS: m/z 482 [(M + H)$^+$, $^{35}$Cl], 484 [(M + H)$^+$, $^{37}$Cl]. |
| 56 | 4-chloro | 2-(3-fluoro-phenyl) | ESIMS: m/z 500 [(M + H)$^+$, $^{35}$Cl], 502 [(M + H)$^+$, $^{37}$Cl]. Analysis for C$_{25}$H$_{23}$ClFN$_3$O$_3$S·2C$_2$H$_2$O$_4$: calcd: C, 51.22; H, 4.00; N, 6.18; found: C, 50.83; H, 4.13; N, 6.12. |
| 57 | 4-chloro | 2-(2-chloro-phenyl) | ESIMS: m/z 516 [(M + H)$^+$, $^{35}$Cl, $^{35}$Cl], 518 [(M + H)$^+$, $^{35}$Cl, $^{37}$Cl], 520 [(M + H)$^+$, $^{37}$Cl, $^{37}$Cl]. |
| 58 | 4-chloro | 2-(3-chloro-phenyl) | ESIMS: m/z 516 [(M + H)$^+$, $^{35}$Cl, $^{35}$Cl], 518 [(M + H)$^+$, $^{35}$Cl, $^{37}$Cl], 520 [(M + H)$^+$, $^{37}$Cl, $^{37}$Cl]. |
| 59 | 4-chloro | 2-(4-chloro-phenyl) | ESIMS: m/z 516 [(M + H)$^+$, $^{35}$Cl, $^{35}$Cl], 518 [(M + H)$^+$, $^{35}$Cl, $^{37}$Cl], 520 [(M + H)$^+$, $^{37}$Cl, $^{37}$Cl]. |
| 60 | 4-chloro | 2-(furan-2-yl) | ESIMS: m/z 472 [(M + H)$^+$, $^{35}$Cl], 474 [(M + H)$^+$, $^{37}$Cl]. |
| 61 | 4-chloro | 2-(thiophen-2-yl) | ESIMS: m/z 488 [(M + H)$^+$, $^{35}$Cl], 490 [(M + H)$^+$, $^{37}$Cl]. |
| 62 | 4-chloro | 2-(thiophen-3-yl) | ESIMS: m/z 488 [(M + H)$^+$, $^{35}$Cl], 490 [(M + H)$^+$, $^{37}$Cl]. |
| 63 | 4-nitro | 2-phenyl | ESIMS: m/z 493 (M + H)$^+$. Analysis for C$_{29}$H$_{28}$N$_4$O$_{13}$S·1.4H$_2$O: calcd: C, 49.91; H, 4.45; N, 8.03; found: C, 49.73, H, 4.09; N, 7.75. |
| 64 | 4-nitro | 2-(2-chloro-phenyl) | ESIMS: m/z 527 [(M + H)$^+$, $^{35}$Cl], 529 [(M + H)$^+$, $^{37}$Cl]. Analysis for C$_{29}$H$_{27}$ClN$_4$O$_{13}$S·0.5H$_2$O: calcd: C, 48.64; H, 3.94; N, 7.82; found: C, 48.42; H, 3.83; N, 7.72. |
| 65 | 4-nitro | 2-(3-chloro-phenyl) | ESIMS: m/z 527 [(M + H)$^+$, $^{35}$Cl], 529 [(M + H)$^+$, $^{37}$Cl]. Analysis for C$_{29}$H$_{27}$ClN$_4$O$_{13}$S·1H$_2$O: calcd: C, 48.04; H, 4.03; N, 7.73; found: C, 48.07; H, 3.87; N, 7.76. |
| 66 | 4-trifluoro-methyl | 2-chloro | ESIMS: m/z 474 [(M + H)$^+$, $^{35}$Cl], 476 [(M + H)$^+$, $^{37}$Cl]. Analysis for C$_{20}$H$_{19}$ClF$_3$N$_3$O$_3$S·1.8C$_2$H$_2$O$_4$: calcd: C, 44.57; H, 3.58; N, 6.61; found: C, 44.49; H, 3.68; N, 6.77. |

Example 48

Isoquinoline-5-sulfonic acid {2-[2-(4-bromo-2-isoxazol-5-yl-phenoxy)-ethylamino]-ethyl}-amide

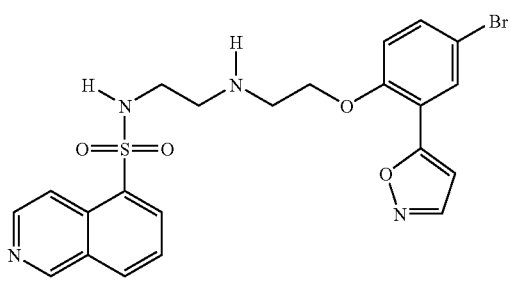

By following a similar procedure as described in Example 34, DIBAL-H reduction of (4-bromo-2-isoxazol-5-yl-phenoxy)-acetic acid methyl ester, and subsequent reductive amination with isoquinoline-5-sulfonic acid (2-amino-ethyl)-amide gives the free amine of the title compound as a white solid. ESIMS: m/z 517 [(M+H)$^+$, $^{79}$Br], 519 [(M+H)$^+$, $^{81}$Br].

Using an analogous procedure to that described in Example 17, with the appropriate starting materials, the following compounds may be prepared as the di-oxalic acid salts.

-continued

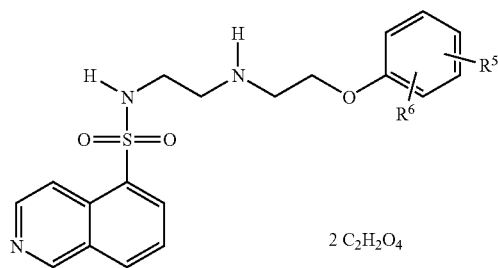

2 C₂H₂O₄

| Ex. # | R⁵ | R⁶ | Data |
|---|---|---|---|
| 67 | 4-trifluoromethyl | 2-phenyl | ESIMS: m/z 516 (M + H)⁺. Analysis for C₂₆H₂₄F₃N₃O₃S·1.3C₂H₂O₄: calcd: C, 54.30; H, 4.24; N, 6.64; found: C, 54.29; H, 4.19; N,6.82. |
| 68 | 4-trifluoromethyl | 2-(3-fluorophenyl) | ESIMS: m/z 534 (M + H)⁺. Analysis for C₃₀H₂₇F₄N₃O₁₁S·0.6H₂O: calcd: C, 49.74; H, 3.92; N, 5.80; found: C, 49.64; H, 3.67; N, 5.72. |
| 69 | 4-trifluoromethyl | 2-(3-chlorophenyl) | ESIMS: m/z 550 [(M + H)⁺, ³⁵Cl], 552 [(M + H)⁺, ³⁷Cl]. Analysis for C₃₀H₂₇ClF₃N₃O₁₁S·0.2H₂O: calcd: C, 49.11; H, 3.76; N, 5.73; found: C, 49.03; H, 3.70; N, 5.69. |

By a method analogous to Example 34, with the appropriate starting materials, the following compounds may be prepared as di-oxalic acid salts.

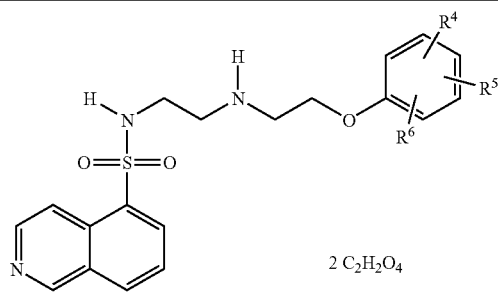

2 C₂H₂O₄

| Ex. # | R⁴ | R⁵ | R⁶ | Data |
|---|---|---|---|---|
| 70 | 6-methyl | 4-chloro | 2-methyl | ESIMS: m/z 434 [(M + H)⁺, ³⁵Cl], 436 [(M + H)⁺, ³⁷Cl]. Analysis for C₂₅H₂₈ClN₃O₁₁S: calcd: C, 48.90; H, 4.60; N, 6.84; found: C, 48.65; H, 4.66; N, 6.63. |
| 71 | 6-methyl | 4-chloro | 2-chloro | ESIMS: m/z 454 [(M + H)⁺, ³⁵Cl, ³⁵Cl], 456 [(M + H)⁺, ³⁵Cl, ³⁷Cl], 458 [(M + H)⁺, ³⁷Cl, ³⁷Cl]. |
| 72 | 5-methyl | 4-chloro | 2-isopropyl | ESIMS: m/z 462 [(M + H)⁺, ³⁵Cl], 464 [(M + H)⁺, ³⁷Cl]. Analysis for C₂₇H₃₂ClN₃O₁₁S·0.4H₂O: calcd: C, 49.95; H, 5.09; N, 6.47; found: C, 50.02; H, 5.10; N, 6.36. |

By a method analogous to Example 34, with the appropriate starting materials, the following compounds may be prepared as di-hydrochloric acid salts.

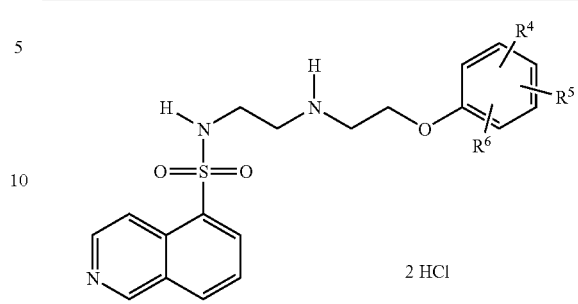

2 HCl

| Ex. # | R⁴ | R⁵ | R⁶ | Data |
|---|---|---|---|---|
| 73 | 6-methyl | 4-bromo | 2-methyl | ESIMS: m/z 478 [(M + H)⁺, ⁷⁹Br], 480 [(M + H)⁺, ⁸¹Br]. Analysis for C₂₁H₂₆BrCl₂N₃O₃S·1H₂O: calcd: C, 44.30; H, 4.96; N, 7.38; found: C, 44.28; H, 4.75; N, 7.35. |
| 74 | 3-methyl | 4-bromo | 5-methyl | ESIMS: m/z 478 [(M + H)⁺, ⁷⁹Br], 480 [(M + H)⁺, ⁸¹Br]. Analysis for C₂₁H₂₆BrCl₂N₃O₃S·1H₂O: calcd: C, 44.73; H, 4.90; N, 7.45; found: C, 44.59; H, 4.63; N, 7.32. |

Example 75

Isoquinoline-5-sulfonic acid {2-[2-(benzofuran-5-yloxy)-ethylamino]-ethyl}-amide di-hydrochloride

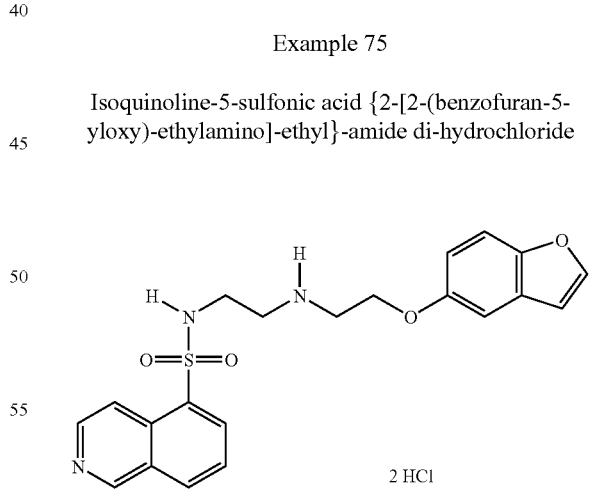

2 HCl

By following similar procedure as described in Example 34, DIBAL-H reduction of (benzofuran-5-yloxy)-acetic acid methyl ester and subsequent reductive amination with isoquinoline-5-sulfonic acid (2-amino-ethyl)-amide gives the free amine product as a gum. The free amine is converted to the di-hydrochloride salt of the title compound as a white powder. EIMS: m/z 412 (M+H)⁺.

Example 76

Isoquinoline-5-sulfonic acid {2-[2-(benzo[1,3]dioxol-5-yloxy)-ethylamino]-ethyl}-amide di-hydrochloride

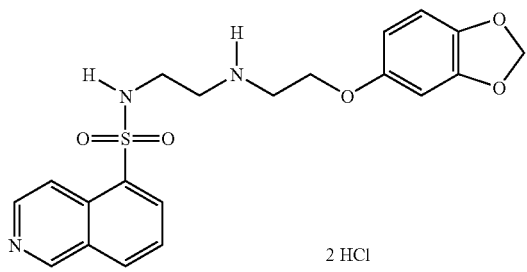

2 HCl

By following similar procedure as described in Example 34, DIBAL-H reduction of (benzo[1,3]dioxol-5-yloxy)-acetic acid methyl ester and subsequent reductive amination with isoquinoline-5-sulfonic acid (2-amino-ethyl)-amide give the free amine product as a gum. The free amine is converted to the di-hydrochloride salt of the title compound as a white powder. ESIMS: m/z 416 (M+H)$^+$.

Example 77

Isoquinoline-5-sulfonic acid {2-[2-(4-chloro-naphthalen-1-yloxy)-ethylamino]-ethyl}-amide di-oxalic acid

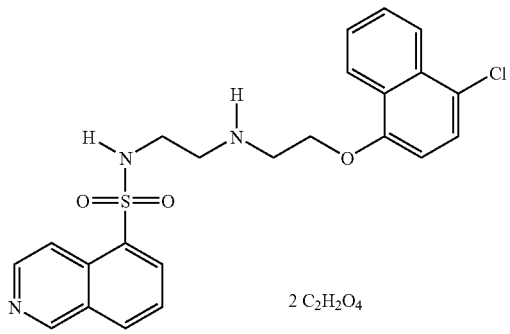

2 C$_2$H$_2$O$_4$

By following similar procedure as described in Example 34, DIBAL-H reduction of (4-chloro-naphthalen-1-yloxy)-acetic acid methyl ester and subsequent reductive amination with isoquinoline-5-sulfonic acid (2-amino-ethyl)-amide gives the free amine product as a gum. The free amine is converted to the di-oxalic acid salt of the title compound as a white powder. ESIMS: m/z 456 [(M+H)$^+$, $^{35}$Cl], 458 [(M+H)$^+$, $^{37}$Cl].

Example 78

Isoquinoline-5-sulfonic acid {2-[2-(4-bromo-2-methyl-phenoxy)-ethylamino]-ethyl}-amide di-hydrochloride

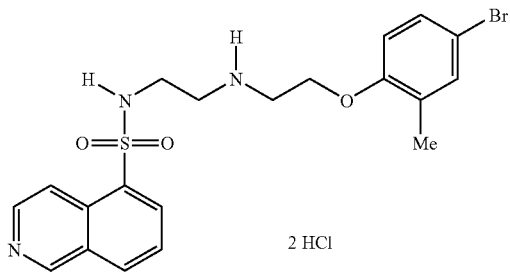

2 HCl

A 5N HCl (15 mL) solution is added to a stirred solution of 4-bromo-1-(2,2-dimethoxy-ethoxy)-2-methyl-benzene (1.40 g, 5.09 mmol) in Et$_2$O (25 mL). The two-layered solution is stirred vigorously at ambient temperature under nitrogen for 2 days. Et$_2$O (50 mL) and saturated aqueous NaCl solution (25 mL) are added to the mixture. The organic layer is separated, washed with a half-saturated aqueous NaCl solution (30 mL) containing saturated NaHCO$_3$ (0.5 mL), dried over MgSO$_4$, filtered and concentrated at ambient temperature to give 1.36 g of the crude (4-bromo-2-methyl-phenoxy)acetaldehyde as oil. The oil is diluted in Et$_2$O to form a stock solution (67 mg/mL), which is used for the subsequent reaction.

A 7.4 mL of the above stock solution (~1.1 mmol) is added to a stirred mixture of 4 Å molecular sieve (600 mg) and isoquinoline-5-sulfonic acid (2-amino-ethyl)-amide (247 mg, 0.983 mmol) in anhydrous CH$_3$OH (8 mL), and the resultant mixture is stirred at ambient temperature for 16 hours. The mixture is cooled to 0° C. before it is treated with powdered sodium borohydride (82 mg, 2.2 mmol). The mixture is stirred at 0° C. for 1 hour then at ambient temperature for another 1 hour. After filtration and subsequent concentration in vacuo, the gummy product is chromatographed on silica (gradient 5-30% CH$_3$OH in EtOAc) to give 326 mg (0.702 mmol, 71% yield) of the free amine product as oil. The free amine (324 mg, 0.698 mmol) is dissolved in CH$_2$Cl$_2$ (25 mL) and treated dropwise with 1N HCl/Et$_2$O solution (2.09 mL) with stirring under nitrogen. The white suspension is stirred for 15 minutes, filtered and dried under vacuum at 60° C. to give 345 mg (0.642 mmol, 92% yield) of the title compound as a white powder. ESIMS: m/z 464 [(M+H)$^+$, $^{79}$Br], 466 [(M+H)$^+$, $^{81}$Br]. Analysis for C$_{20}$H$_{24}$BrCl$_2$N$_3$O$_3$S.1.4H$_2$O: calcd: C, 42.70; H, 4.80; N, 7.47; found: C, 42.42; H, 4.44; N, 7.36.

Example 79

7-Phenyl-isoquinoline-5-sulfonic acid {2-[2-(4-chloro-phenoxy)-ethylamino]-ethyl}-amide di-hydrochloride

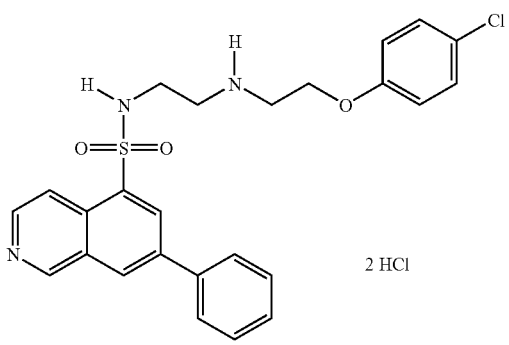

2 HCl

A 1.96 mL of (4-chloro-phenoxy)-acetaldehyde stock solution (~0.46 mmol) is added to a stirred mixture of 7-phenyl-isoquinoline-5-sulfonic acid (2-amino-ethyl)-amide di-hydrochloride (152 mg, 0.380 mmol), 4 Å molecular sieve (300 mg) and NEt$_3$ (0.212 mL, 1.52 mmol) in anhydrous CH$_3$OH (4 mL) at ambient temperature under nitrogen. The resultant mixture is stirred for 16 hours. Then the mixture is cooled to 0° C. before it is treated with powdered sodium borohydride (43.1 mg, 1.14 mmol). The mixture is stirred at 0° C. for 1 hour, then at ambient temperature for another 1 hour. After filtration and subsequent concentration in vacuo, the crude product is chromatographed on silica (gradient 5-25% CH₃OH in EtOAc) to give 104 mg of the free amine product as a gum (0.216 mmol, 57% yield). The free amine (102 mg, 0.212 mmol) is dissolved in EtOAc (15 mL) and treated dropwise with 1N HCl/Et₂O solution (0.635 mL) with stirring under nitrogen. The white suspension is stirred for 15 minutes, filtered and dried under vacuum at 60° C. to give 112 mg (0.202 mmol, 95% yield) of the title compound as a white powder. ESIMS: m/z 482 [(M+H)$^+$, $^{35}$Cl], 484 [(M+H)$^+$, $^{37}$Cl].

Using a procedure analogous to Example 79, with the appropriate starting materials, the following compounds may be prepared as the di-hydrochloric acid salts.

| Ex. # | R$^5$ | R$^6$ | Data |
|---|---|---|---|
| 80 | chloro | chloro | ESIMS: m/z 516 [(M + H)$^+$, $^{35}$Cl, $^{35}$Cl], 518 [(M + H)$^+$, $^{35}$Cl, $^{37}$Cl], 520 [(M + H)$^+$, $^{37}$Cl, $^{37}$Cl]. Analysis for C$_{25}$H$_{25}$Cl$_4$N$_3$O$_3$S·0.4H$_2$O: calcd: C, 50.33; H, 4.36; N, 7.04; found: C, 50.33; H, 4.02; N, 6.90. |
| 81 | chloro | benzyl | ESIMS: m/z 572 [(M + H)$^+$, $^{35}$Cl], 574 [(M + H)$^+$, $^{37}$Cl]. |
| 82 | trifluoro-methyl | H | ESIMS: m/z 516 (M + H)$^+$. Analysis for C$_{26}$H$_{26}$F$_3$Cl$_2$N$_3$O$_3$S·0.9H$_2$O: calcd: C, 51.64; H, 4.63; N, 6.95; found: C, 51.33; H, 4.24; N, 6.78. |
| 83 | nitro | H | ESIMS: m/z 493 (M + H)$^+$. |
| 84 | bromo | methyl | ESIMS: m/z 540 [(M + H)$^+$, $^{79}$Br], 542 [(M + H)$^+$, $^{81}$Br]. |
| 85 | bromo | H | ESIMS: m/z 526 [(M + H)$^+$, $^{79}$Br], 528 [(M + H)$^+$, $^{81}$Br]. |
| 86 | chloro | 2-chloro-phenyl | ESIMS: m/z 592 [(M + H)$^+$, $^{35}$Cl, $^{35}$Cl], 594 [(M + H)$^+$, $^{35}$Cl, $^{37}$Cl] |
| 87 | chloro | 3-trifluoro-methyl-phenyl | ESIMS: m/z 626 [(M + H)$^+$, $^{35}$Cl], 628 [(M + H)$^+$, $^{37}$Cl] |
| 88 | chloro | 2-phenyl-(3'-methyl-sulfonyl-amino) | ESIMS: m/z 651 [(M + H)$^+$, $^{35}$Cl], 653 [(M + H)$^+$, $^{37}$Cl]. |

Using a procedure analogous to Example 79, with the appropriate starting materials, the following compounds may be prepared as the di-oxalic acid salts.

| Ex. # | R$^4$ | R$^5$ | R$^6$ | Data |
|---|---|---|---|---|
| 89 | H | chloro | methyl | ESIMS: m/z 496 [(M + H)$^+$, $^{35}$Cl], 498 [(M + H)$^+$, $^{37}$Cl]. Analysis for C$_{30}$H$_{30}$ClN$_3$O$_{11}$S·0.7H$_2$O: calcd: C, 52.32; H, 4.60; N, 6.10; found: C, 52.41; H, 4.58; N, 5.77. |
| 90 | H | chloro | propyl | ESIMS: m/z 524 [(M + H)$^+$, $^{35}$Cl], 526 [(M + H)$^+$, $^{37}$Cl]. |
| 91 | H | chloro | 4-chloro-benzyl | ESIMS: m/z 606 [(M + H)$^+$, $^{35}$Cl, $^{35}$Cl], 608 [(M + H)$^+$, $^{35}$Cl, $^{37}$Cl], 610 [(M + H)$^+$, $^{37}$Cl, $^{37}$Cl]. Analysis for C$_{36}$H$_{33}$Cl$_2$N$_3$O$_{11}$S: calcd: C, 54.97; H, 4.23; N, 5.34; found: C, 54.77; H, 4.11; N, 5.49. |
| 92 | H | chloro | isoxazol-5-yl | ESIMS: m/z 549 [(M + H)$^+$, $^{35}$Cl], 551 [(M + H)$^+$, $^{37}$Cl]. |
| 93 | H | chloro | phenyl | ESIMS: m/z 558 [(M + H)$^+$, $^{35}$Cl], 560 [(M + H)$^+$, $^{37}$Cl]. Analysis for C$_{35}$H$_{32}$ClN$_3$O$_{11}$S·0.5H$_2$O: calcd: C, 56.26; H, 4.45; N, 5.62; found: C, 56.35; H, 4.60; N, 5.53. |
| 94 | methyl | chloro | isopropyl | ESIMS: m/z 538 [(M + H)$^+$, $^{35}$Cl], 540 [(M + H)$^+$, $^{37}$Cl]. Analysis for C$_{29}$H$_{32}$ClN$_3$O$_3$S·1.9C$_2$H$_2$O$_4$: calcd: C, 55.55; H, 5.09; N, 5.93; found: C, 55.75; H, 5.13; N, 5.95. |
| 95 | H | H | benzyl | ESIMS: m/z 538 [(M + H)$^+$, $^{35}$Cl], 540 [(M + H)$^+$, $^{37}$Cl]. Analysis for C$_{36}$H$_{35}$N$_3$O$_{11}$S: calcd: C, 60.24; H, 4.92; N, 5.85; found: C, 59.97; H, 5.22; N, 5.71. |

Example 96

1-Hydroxy-isoquinoline-5-sulfonic acid {2-[2-(2-trifluoromethyl-phenoxy)-ethylamino]-ethyl}-amide hydrochloride

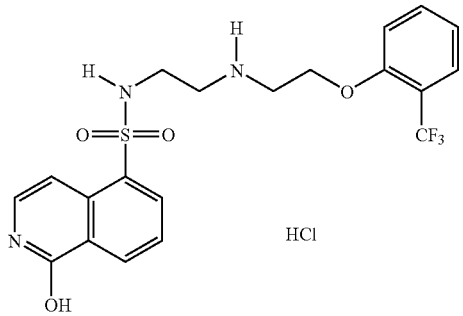

A 4.2 mL of the (2-trifluoromethyl-phenoxy)-acetaldehyde stock solution (~0.69 mmol) is added to a stirred mixture of 1-chloro-isoquinoline-5-sulfonic acid (2-aminoethyl)-amide hydrochloride (200 mg, 0.621 mmol), 4 Å molecular sieve (400 mg) and $NEt_3$ (0.19 mL, 1.4 mmol) in anhydrous $CH_3OH$ (5 mL) at ambient temperature under nitrogen. The resultant mixture is stirred for 16 hours. The mixture is cooled to 0° C. before it is treated with powdered sodium borohydride (53 mg, 1.4 mmol). The mixture is stirred at 0° C. for 1 hour and at ambient temperature for another 1 hour. After filtration and subsequent concentration in vacuo, the crude product is chromatographed on silica (gradient 0-5% $CH_3OH$ in $CH_2Cl_2$) to give 92 mg (0.19 mmol, 31% yield) of 1-chloro-isoquinoline-5-sulfonic acid {2-[2-(2-trifluoromethyl-phenoxy)-ethylamino]-ethyl}-amide. ESIMS: m/z 474 [(M+H)$^+$, $^{35}$Cl], 476 [(M+H)$^+$, $^{37}$Cl].

A 0.6 mL 5N HCl solution is added to a stirred solution of 1-chloro-isoquinoline-5-sulfonic acid {2-[2-(2-trifluoromethyl-phenoxy)-ethylamino]-ethyl}-amide (70 mg, 0.15 mmol) in THF (1 mL) at ambient temperature under nitrogen. The resultant mixture is heated at 65° C. for 16 hours. At ambient temperature, the mixture is concentrated. The crude product is dissolved in a small amount of $MeOH/CH_2Cl_2$ before it is treated with $Et_2O$ to form a white suspension. After filtration and vacuum drying, 24 mg (0.49 mmol, 33% yield) of the title compound is obtained as a white powder. ESIMS: m/z 456 (M+H)$^+$.

Using a procedure similar to that described in Example 96, with the appropriate starting materials, the following compounds may be prepared as the hydrochloride salts.

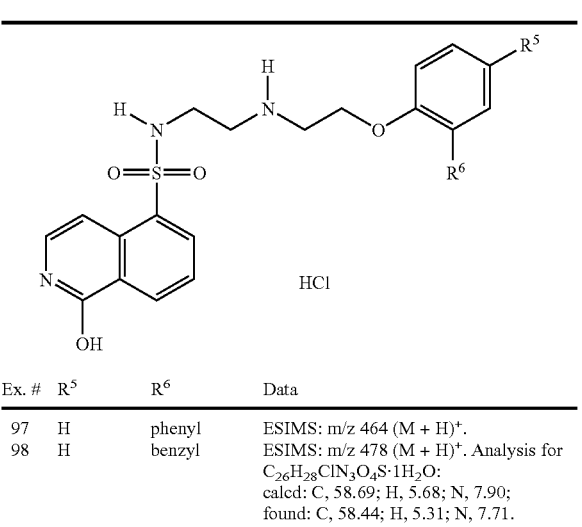

| Ex. # | R$^5$ | R$^6$ | Data |
|---|---|---|---|
| 97 | H | phenyl | ESIMS: m/z 464 (M + H)$^+$. |
| 98 | H | benzyl | ESIMS: m/z 478 (M + H)$^+$. Analysis for $C_{26}H_{28}ClN_3O_4S \cdot 1H_2O$: calcd: C, 58.69; H, 5.68; N, 7.90; found: C, 58.44; H, 5.31; N, 7.71. |

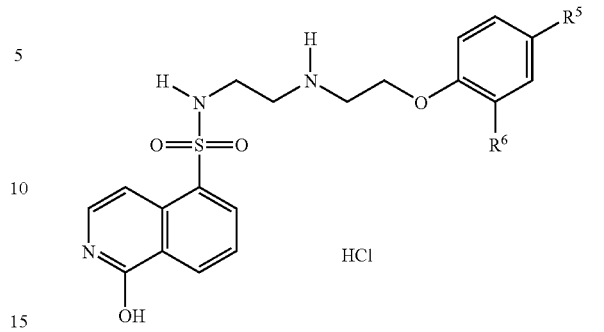

| Ex. # | R$^5$ | R$^6$ | Data |
|---|---|---|---|
| 99 | chloro | H | ESIMS: m/z 422 [(M + H)$^+$, $^{35}$Cl], 424 [(M + H)$^+$, $^{37}$Cl]. Analysis for $C_{19}H_{21}Cl_2N_3O_4S \cdot 1H_2O$: calcd: C, 47.90; H, 4.87; N, 8.82; found: C, 47.91; H, 4.63; N, 8.76. |
| 100 | bromo | H | ESIMS: m/z 466 [(M + H)$^+$, $^{79}$Br], 468 [(M + H)$^+$, $^{81}$Br]. |
| 101 | trifluoromethyl | H | ESIMS: m/z 456 (M + H)$^+$. Analysis for $C_{20}H_{21}ClF_3N_3O_4S \cdot 1H_2O$: calcd: C, 47.11; H, 4.55; N, 8.24; found: C, 47.08; H, 4.19; N, 8.25. |
| 102 | methoxy | H | ESIMS: m/z 418 (M + H)$^+$. Analysis for $C_{20}H_{24}ClN_3O_5S \cdot 0.8H_2O$: calcd: C, 51.29; H, 5.51; N, 8.97; found: C, 51.35; H, 5.14; N, 8.87. |
| 103 | chloro | 3-fluorophenyl | ESIMS: m/z 516 [(M + H)$^+$, $^{35}$Cl], 518 [(M + H)$^+$, $^{37}$Cl]. Analysis for $C_{25}H_{24}Cl_2FN_3O_4S \cdot 0.4H_2O$: calcd: C, 53.65; H, 4.47; N, 7.51; found: C, 53.75; H, 4.31; N, 7.38. |
| 104 | chloro | 2-chlorophenyl | ESIMS: m/z 532 [(M + H)$^+$, $^{35}$Cl, $^{35}$Cl], 534 [(M + H)$^+$, $^{35}$Cl, $^{37}$Cl], 536 [(M + H)$^+$, $^{37}$Cl, $^{37}$Cl]. |
| 105 | chloro | 3-chlorophenyl | ESIMS: m/z 532 [(M + H)$^+$, $^{35}$Cl, $^{35}$Cl], 534 [(M + H)$^+$, $^{35}$Cl, $^{37}$Cl], 536 [(M + H)$^+$, $^{37}$Cl, $^{37}$Cl]. |
| 106 | chloro | benzyl | ESIMS: m/z 512 [(M + H)$^+$, $^{35}$Cl], 514 [(M + H)$^+$, $^{37}$Cl]. |
| 107 | chloro | 4-chlorobenzyl | ESIMS: m/z 546 [(M + H)$^+$, $^{35}$Cl, $^{35}$Cl], 548 [(M + H)$^+$, $^{35}$Cl, $^{37}$Cl], 550 [(M + H)$^+$, $^{37}$Cl, $^{37}$Cl]. Analysis for $C_{26}H_{26}Cl_3N_3O_4S \cdot 0.4H_2O$: calcd: C, 52.92; H, 4.58; N, 7.12; found: C, 52.93; H, 4.39; N, 6.93. |
| 108 | trifluoromethyl | phenyl | ESIMS: m/z 532 (M + H)$^+$. Analysis for $C_{26}H_{25}ClF_3N_3O_4S \cdot 0.8H_2O$: calcd: C, 53.62; H, 4.60; N, 7.21; found: C, 53.52; H, 4.31; N, 7.24. |
| 109 | nitro | phenyl | ESIMS: m/z 507 (M − H)$^-$. |
| 110 | Nitro | 3-chlorophenyl | ESIMS: m/z 543 (M + H)$^+$. |
| 110A | chloro | 2-phenyl-(3'-methylsulfonylamino) | ESIMS: m/z 591 [(M + H)$^+$, $^{35}$Cl], 593 [(M + H)$^+$, $^{37}$Cl]. |

Example 111

1-Hydroxy-isoquinoline-5-sulfonic acid {2-[2-(5,2'-dichloro-biphenyl-2-yloxy)-ethylamino]-ethyl}-amide hydrochloride

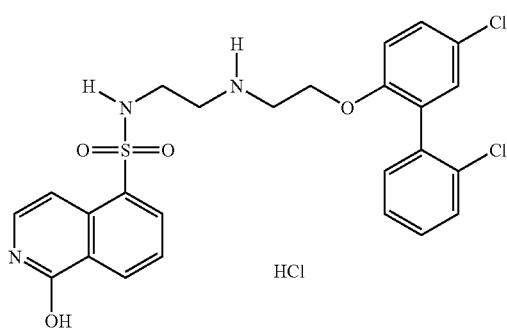

A 6.0 mL of the (5,2'-dichloro-biphenyl-2-yloxy)-acetaldehyde stock solution (1.88 mmol) is added to a stirred mixture of 1-hydroxy-isoquinoline-5-sulfonic acid (2-aminoethyl)-amide sodium chloride (438 mg, 1.34 mmol) and 4 Å molecular sieve (400 mg) in anhydrous $CH_3OH$ (8 mL) at ambient temperature under nitrogen. The resultant mixture is stirred for 16 hours. After being cooled to 0° C., the mixture is treated with powdered sodium borohydride (112 mg, 2.95 mmol), then stirred at 0° C. for 1 hour and at ambient temperature for another 1 hour. After filtration and subsequent concentration in vacuo, the crude product is chromatographed on silica (gradient 5-15% $CH_3OH$ in EtOAc) to give the desired product as a gum. It is dissolved in EtOAc (15 mL), filtered and concentrated to give 493 mg (0.926 mmol, 69% yield) of the free amine as a white solid. The free amine is dissolved in EtOAc (3,0 mL) and subsequently treated dropwise with 1N HCl/$Et_2O$ (8 mL) to give a white suspension. After filtration and vacuum drying at 50° C., 470 mg (0.8.26 mmol, 89% yield) of the title compound is obtained as a white powder. ESIMS: m/z 532 [$(M+H)^+$, $^{35}Cl$, $^{35}Cl$], 534 [$(M+H)^+$, $^{35}Cl$, $^{37}Cl$], 536 [$(M+H)^+$, $^{37}Cl$, $^{37}Cl$].

Example 112

Isoquinoline-5-sulfonic acid (2-{[2-(2-benzyl-phenoxy)-ethyl]-methyl-amino}-ethyl)-tert-butyl-amide di-oxalic acid

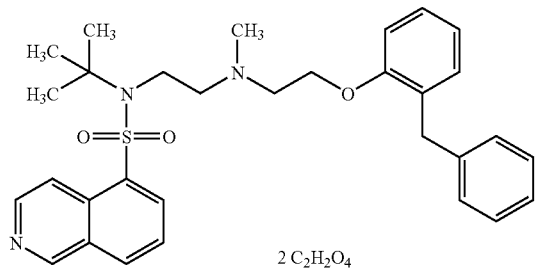

Powdered $Cs_2CO_3$ (368 mg, 1.13 mmol) is added to a stirred solution of isoquinoline-5-sulfonic acid tert-butylamide (100 mg, 0.378 mmol) and [2-(2-benzyl-phenoxy)-ethyl]-(2-chloro-ethyl)-methyl-amine hydrochloride (129 mg, 0.378 mmol) in dry DMF (1 mL) at ambient temperature under nitrogen. The resultant mixture is heated at 90° C. for 2 hours. At ambient temperature, EtOAc (10 mL) is added to the mixture and the mixture is washed with water (5 mL×3). The organic layer is dried over $MgSO_4$, filtered and concentrated. The crude product is chromatographed on silica (gradient 0-50% EtOAc in $CH_2Cl_2$) to give 140 mg (0.263 mmol, 70% yield) of the product as a gum. Some product (36.8 mg, 0.0692 mmol) is dissolved in EtOAc (2.5 mL) and treated with a 2.5 mL EtOAc solution containing oxalic acid (17.5 mg, 0.138 mmol). The solution is concentrated to give 49.0 mg of the title compound as a white solid. ESIMS: m/z 532 $(M+H)^+$.

Example 113

Isoquinoline-5-sulfonic acid (2-{[2-(2-benzyl-phenoxy)-ethyl]-methyl-amino}-ethyl)-amide di-oxalic acid

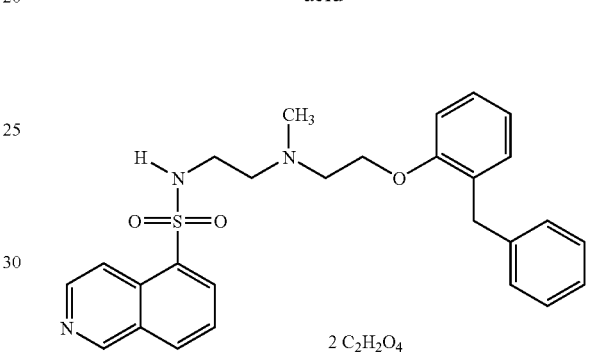

Triethylsilane (0.149 mL, 0.932 mmol) is added to a stirred trifluoroacetic acid (2 mL) solution containing the free amine of isoquinoline-5-sulfonic acid (2-{[2-(2-benzyl-phenoxy)-ethyl]-methyl-amino}-ethyl)-tert-butyl-amide di-oxalic acid (99.1 mg, 0.186 mmol). The resultant solution is heated at 65° C. under nitrogen for 24 hours. After concentration and subsequent chromatography on silica (gradient 0-50% EtOAc in $CH_2Cl_2$, then 10% 4.2N $NMe_3$/EtOH in $CH_2Cl_2$), 52.1 mg (0.110 mmol, 59% yield) of the product is obtained as a gum. Subsequently, it is converted to the di-oxalic acid salt of the title compound as a white solid. ESIMS: m/z 476 $(M+H)^+$.

Example 114

Isoquinoline-5-sulfonic acid {2-[2-(2-benzyl-phenoxy)-ethylamino]-ethyl}-methyl-amide di-hydrochloride

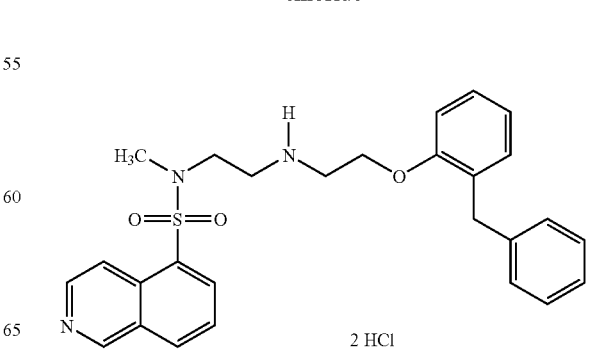

A 4N HCl (in 1,4-dioxane, 3 mL) solution is added to a stirred solution of [2-(2-benzyl-phenoxy)-ethyl]-{2-[(isoquinoline-5-sulfonyl)-methyl-amino]-ethyl}-carbamic acid tert-butyl ester (65.0 mg, 0.113 mmol) in anhydrous CH$_2$Cl$_2$ (1 mL) at ambient temperature under nitrogen. The resultant solution is stirred for 2 hours. The mixture is concentrated and the product is treated with CH$_3$OH/EtOAc to form a white suspension. After filtration and vacuum drying, 52.5 mg (0.0957 mmol, 85% yield) of the title compound is obtained as a white solid. ESIMS: m/z 476 (M+H)$^+$.

Example 115

[{2-[2-(2-Benzyl-phenoxy)-ethylamino]-ethyl}-(isoquinoline-5-sulfonyl)-amino]-acetic acid di-hydrochloride

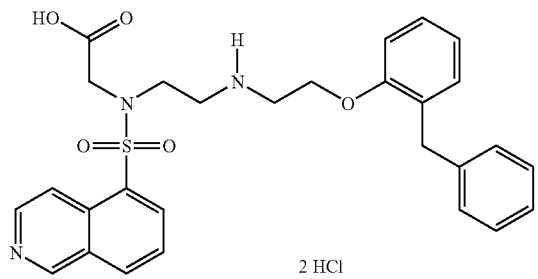

2 HCl

By following similar procedure as described in Example 114, acidic deprotection of [(2-{[2-(2-benzyl-phenoxy)-ethyl]-tert-butoxycarbonyl-amino}-ethyl)-(isoquinoline-5-sulfonyl)-amino]-acetic acid tert-butyl ester (65.0 mg, 0.0962 mmol) gives 42.5 mg (75% yield) of the title compound as a white solid. ESIMS: m/z 520 (M+H)$^+$.

Example 116

Isoquinoline-5-sulfonic acid {2-[2-(2-benzyl-phenoxy)-ethylamino]-ethyl}-(2-dimethylamino-ethyl)-amide tri-hydrochloride

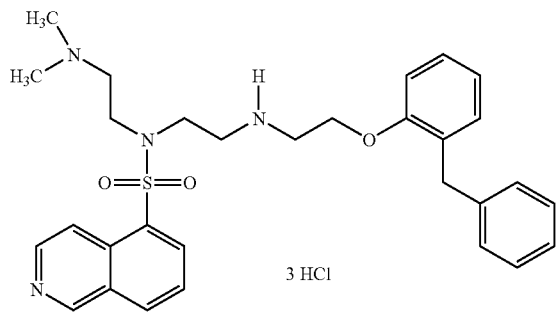

3 HCl

By following similar procedure as described in Example 114, acidic deprotection of [2-(2-benzyl-phenoxy)-ethyl]-{2-[(2-dimethylamino-ethyl)-(isoquinoline-5-sulfonyl)-amino]-ethyl}-carbamic acid tert-butyl ester (71.3 mg, 0.113 mmol) gives 71.5 mg (99% yield) of the title compound as a tan foam. ESIMS: m/z 533 (M+H)$^+$.

Example 117

1-Hydroxy-isoquinoline-5-sulfonic acid {2-[3-(2-benzyl-4-chloro-phenoxy)-propylamino]-ethyl}-amide hydrochloride

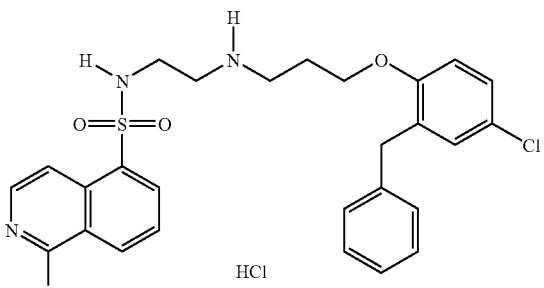

HCl

Trifluoroacetic acid (0.252 mL, 3.27 mmol) is added to a stirred solution of 1-chloro-isoquinoline-5-sulfonic acid (2-{[3-(2-benzyl-4-chloro-phenoxy)-propyl]-bis-(4-methoxyphenyl)-methyl]-amino}-ethyl)-amide (252 mg, 0.327 mmol) and triethylsilane (0.104 mL, 0.654 mmol) in anhydrous CH$_2$Cl$_2$ (5 mL) at ambient temperature under nitrogen. The resultant mixture is stirred for 30 minutes, then concentrated to give the crude product as TFA salt.

The crude product is dissolved in 1,4-dioxane (8 mL) and treated with 5N HCl (5 mL) and the resultant mixture is stirred at 70° C. under nitrogen for 4 hours. After concentration in vacuo and subsequent chromatography on silica (gradient 0-10% 2M NH$_3$/CH$_3$OH in CH$_2$Cl$_2$), the 1-OH product is obtained as gum. It is dissolved in EtOAc (12 mL) and treated dropwise with 1N HCl (0.7 mL, in Et$_2$O) to form a white suspension. After filtration and vacuum drying at 60° C., 147 mg (0.279 mmol, 90% yield) of the title compound is obtained as foam. ESIMS: m/z 526 [(M+H)$^+$, $^{35}$Cl], 528 [(M+H)$^+$, $^{37}$Cl].

Using a method similar to Example 117 and the appropriate starting materials, the following compounds may be prepared as the hydrochloride or di-oxalic acid salts.

| Ex. # | R$^1$ | R$^5$ | Data |
|---|---|---|---|
| 118 | H | chloro | Prepared as di-oxalic acid salt. ESIMS: m/z 510 [(M + H)$^+$, $^{35}$Cl], 512 [(M + H)$^+$, $^{37}$Cl]. Analysis for C$_{31}$H$_{32}$ClN$_3$O$_{11}$S: calcd: C, 53.95; H, 4.67; N, 6.09; found: C, 53.97; H, 4.67; N, 6.08. |
| 119 | hydroxy | H | Prepared as hydrochloride salt. ESIMS: m/z 492 (M + H)$^+$. |

-continued

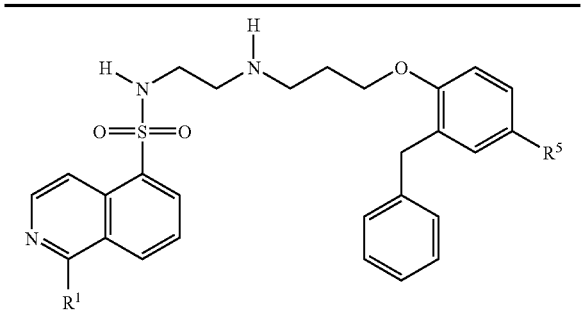

| Ex. # | R[1] | R[5] | Data |
|---|---|---|---|
| 120 | H | H | Prepared as di-oxalic acid salt. ESIMS: m/z 476 (M + H)+. Analysis for $C_{31}H_{33}ClN_3O_{11}S$: calcd: C, 56.79; H, 5.07; N, 6.41; found: C, 56.67; H, 4.90; N, 6.43. |

Example 121

Isoquinoline-5-sulfonic acid {2-[2-(4-bromo-phenyl-sulfanyl)-ethylamino]-ethyl}-amide di-hydrochloride

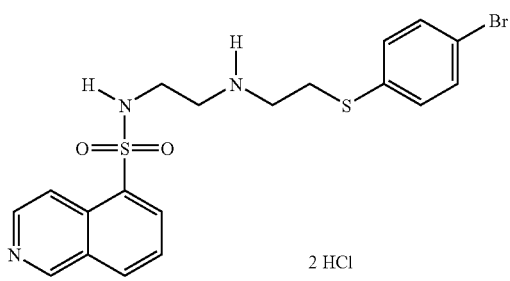

Using the procedure described in Example 1, DIBAL-H reduction of (4-bromo-phenylsulfanyl)-acetic acid methyl ester and subsequent reductive amination with isoquinoline-5-sulfonic acid (2-amino-ethyl)-amide gives the free amine product as a gum (39% yield). The free amine is converted to the HCl salt of the title compound (89% yield) as a hygroscopic white powder. ESIMS: m/z 466 [(M+H)+, [79]Br], 468 [(M+H)+, [81]Br]. Analysis for $C_{19}H_{22}BrCl_2N_3O_2S\cdot1.4H_2O$: calcd: C, 40.42; H, 4.43; N, 7.44; found: C, 40.20; H, 4.22; N, 7.36.

Example 122

Isoquinoline-5-sulfonic acid {2-[2-(4-bromo-benzenesulfonyl)-ethylamino]-ethyl}-amide

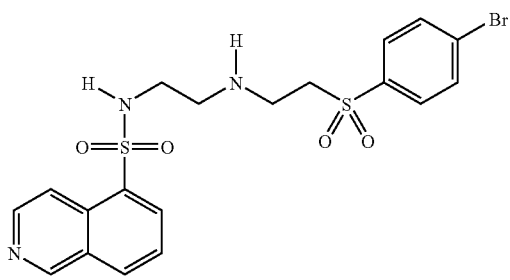

A stirred mixture of isoquinoline-5-sulfonic acid {2-[2-(4-bromo-phenylsulfanyl)-ethylamino]-ethyl}-amide (73.0 mg, 0.157 mmol) and oxone (289 mg, 0.470 mmol) in $CH_3OH$ (5 mL)/$H_2O$ (1.3 mL) is allowed to stir at ambient temperature for 30 minutes to form a suspension. After filtration, the white solid is sonicated in $H_2O$ (10 mL), then filtered to give a tan solid of the title compound. ESIMS: m/z 498 [(M+H)+, [79]Br], 500 [(M+H)+, [81]Br].

Example 123

Isoquinoline-5-sulfonic acid (2-{2-[(4-chloro-phenyl)-methyl-amino]-ethylamino}-ethyl)-amide di-oxalic acid

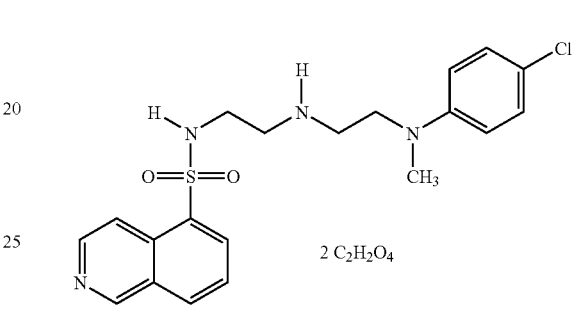

By following a similar procedure as described in Example 1, DIBAL-H reduction of [(4-chloro-phenyl)-methyl-amino]-acetic acid methyl ester (aqueous Rochelle's salt work-up) and subsequent reductive amination with isoquinoline-5-sulfonic acid (2-amino-ethyl)-amide gives the free amine product as a gum (60% yield). The free amine is converted to the oxalic acid salt of the title compound (99% yield) as a white powder. ESIMS: m/z 419 [(M+H)+, [35]Cl], 421 [(M+H)+, [37]Cl].

Example 124

Isoquinoline-5-sulfonic acid {2-[2-(2-benzyl-4-chloro-phenylamino)-ethylamino]-ethyl}-amide di-oxalic acid

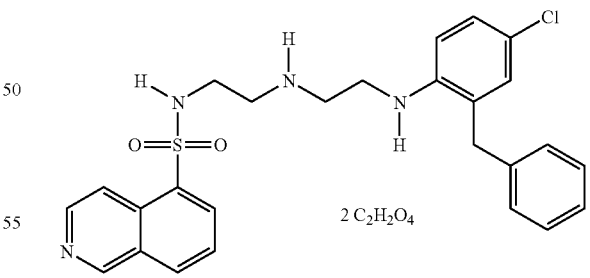

By following similar procedure as described in Example 1, DIBAL-H reduction of [(2-benzyl-4-chloro-phenyl)-(2,2,2-trifluoro-acetyl)-amino]-acetic acid methyl ester (aqueous Rochelle's salt work-up) and subsequent reductive amination with isoquinoline-5-sulfonic acid (2-amino-ethyl)-amide gives the free amine product as a yellowish gum (3% yield). The free amine is converted to the oxalic acid salt of the title compound (99% yield) as a yellowish solid. ESIMS: m/z 495 [(M+H)+, [35]Cl], 497 [(M+H)+, [37]Cl].

Example 125

Isoquinoline-5-sulfonic acid {2-[2-(2-benzoyl-4-chloro-phenoxy)-ethylamino]-ethyl}-amide di-hydrochloride

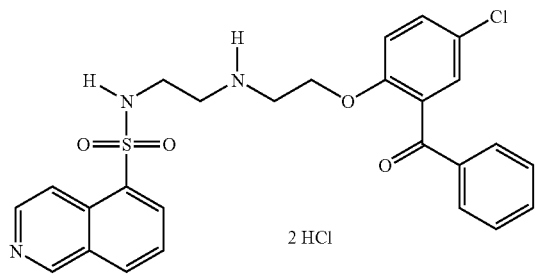

2 HCl

A solution of isoquinoline-5-sulfonic acid (2-aminoethyl)-amide (20 mg, 0.080 mmol), [2-(2-bromo-ethoxy)-5-chloro-phenyl]-phenyl-methanone (29 mg (0.085 mmol) and potassium carbonate (18 mg, 0.13 mmol) in anhydrous DMF (0.12 mL) is stirred at ambient temperature for 14 hours. After dilution with 10% MeOH in CHCl$_3$, the mixture is poured into 10 mL of water and extracted three times with 10% MeOH in CHCl$_3$. The extracts are dried over Na$_2$SO$_4$ and evaporated. The crude residue is purified by column chromatography to afford 27 mg (66%) of the free amine product. APCI-MS: m/z 510 [(M+H)$^+$, $^{35}$Cl], 512 [(M+H)$^+$, $^{37}$Cl]. APCI-MS: [M−H]$^−$: m/z 508, 510. $^1$H-NMR (300 MHz; CDCl$_3$): δ9.34 (1H, s); 8.63 (1H, d, 6.2 Hz); 8.42 (2H, t, 7.0 Hz); 8.20 (1H, d, 8.1 Hz); 7.73 (2H, d, 7.8 Hz); 7.67-7.75 (3H, m); 7.36-7.51 (5H,m); 6.85 (1H, d, 8.6 Hz); 3.80 (2H, t, 4.6 Hz); 2.82 (2H, t, 5.5 Hz); 2.40 (2H, t, 4.6 Hz); 2.35 (2H, t, 5.5 Hz).

A 20 mg portion of this material is dissolved in ethyl acetate and treated with 0.5 mL of 2M HCl in Et$_2$O. After stirring for 30 minutes, the solid is collected by filtration, washed with 2% methanol in chloroform and dried under vacuum to afford 17 mg of hydrochloride salt of the title compound as a white solid; $^1$H-NMR (300 MHz; d$_4$-MeOH): δ9.89 (1H, br s); 9.04 (1H, br d, 6.2 Hz); 8.73-8.80 (3H, m); 8.13 (1H, t, 8.1 Hz); 7.79 (2H, d, 7.3 Hz); 7.66 (1H, br t, 7.4 Hz); 7.60 (1H, dd, 8.9 and 2.5 Hz); 7.51 (2H, t, 7.3 Hz); 7.38 (1H, d, 2.6 Hz); 7.28 (1H, d, 8.9 Hz); 4.39 (2H, t, 4.7 Hz); 3.32 (2H; t, 5.4 Hz); 3.13 (4H, br s).

Example 126

Isoquinoline-5-sulfonic acid {2-[2-(2-bromo-4-fluoro-phenyloxy)-ethylamino]-ethyl}-amide

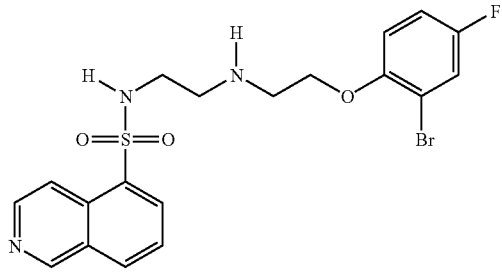

By following a similar procedure as described in Example 1, DIBAL-H reduction of (2-bromo-4-fluoro-phenoxy)-acetic acid methyl ester, and subsequent reductive amination with isoquinoline-5-sulfonic acid (2-amino-ethyl)-amide gives the free amine of the title compound as a white foam. ESIMS: m/z 468 [(M+H)$^+$, $^{79}$Br], 470 [(M+H)$^+$, $^{81}$Br].

Example 127

Isoquinoline-5-sulfonic acid {2-[2-(2-bromo-4-methyl-phenyloxy)-ethylamino]-ethyl}-amide

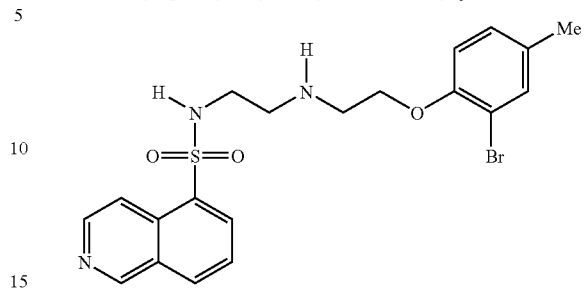

By following a similar procedure as described in Example 1, DIBAL-H reduction of (2-bromo-4-methyl-phenoxy)-acetic acid methyl ester, and subsequent reductive amination with isoquinoline-5-sulfonic acid (2-amino-ethyl)-amide gives the free amine of the title compound as a clear gum. ESIMS: m/z 464 [(M+H)$^+$, $^{79}$Br], 466 [(M+H)$^+$, $^{81}$Br].

Example 128

Isoquinoline-5-sulfonic acid {2-[2-(4-chloro-2-(3-trifluoromethyl-benzyl)-phenyloxy)-ethylamino]-ethyl}-amide

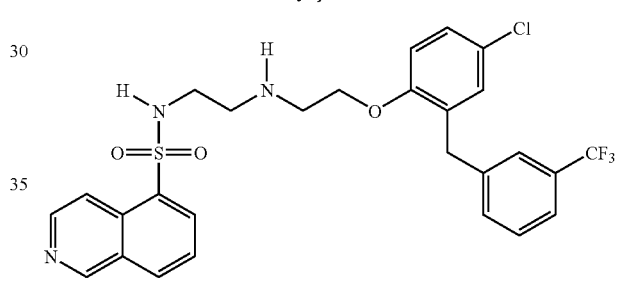

By following a similar procedure as described in Example 1, DIBAL-H reduction of [4-chloro-2-(3-trifluoromethyl-benzyl)-phenyloxy]-acetic acid methyl ester, and subsequent reductive amination with isoquinoline-5-sulfonic acid (2-amino-ethyl)-amide gives the free amine of the title compound as a clear gum. ESIMS: m/z 564 [(M+H)$^+$, $^{35}$Cl], 566 [(M+H)$^+$, $^{37}$Cl].

Example 129

Isoquinoline-5-sulfonic acid {2-[2-(2-(3-trifluorophenyl)-phenoxy)-ethylamino]-ethyl}-amide di-oxalic acid

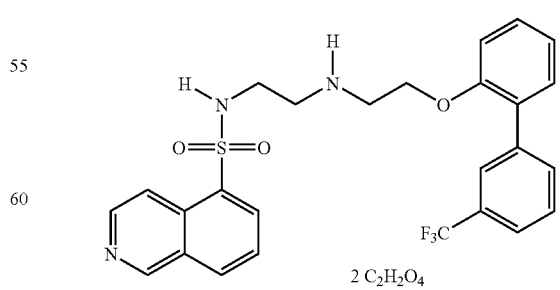

2 C$_2$H$_2$O$_4$

By following a similar procedure as described in Example 17, the title compound is obtained as a white powder. ESIMS: m/z 516 (M+H)$^+$.

Using an analogous procedure to that described in Example 17, with the appropriate starting materials, the following compounds may be prepared as the di-oxalic acid salt.

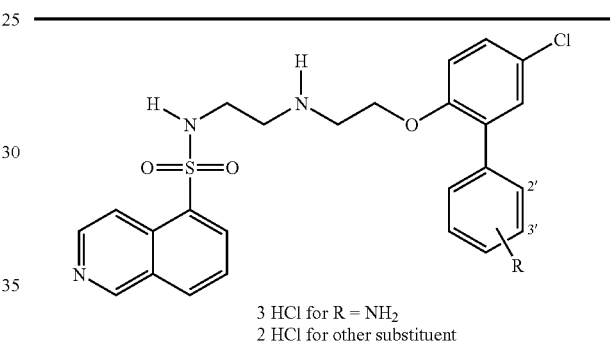

| Ex. # | R$^5$ | R$^6$ | Data |
|---|---|---|---|
| 130 | 4-chloro | 2-(5-chloro-thien-2-yl) | ESIMS: m/z 522 [(M + H)$^+$, $^{35}$Cl, $^{35}$Cl], 524 [(M + H)$^+$, $^{35}$Cl, $^{37}$Cl], 526 [(M + H)$^+$, $^{37}$Cl, $^{37}$Cl]. |
| 131 | 4-chloro | 2-(3-phenyl-phenyl) | ESIMS: m/z 558 [(M + H)$^+$, $^{35}$Cl], 560 [(M + H)$^+$, $^{37}$Cl]. |
| 132 | 4-chloro | 2-(3-trifluoro-methyl-phenyl) | ESIMS: m/z 550 [(M + H)$^+$, $^{35}$Cl], 552 [(M + H)$^+$, $^{37}$Cl]. |
| 133 | 4-chloro | 2-(4-trifluoro-methyl-phenyl) | ESIMS: m/z 550 [(M + H)$^+$, $^{35}$Cl], 552 [(M + H)$^+$, $^{37}$Cl]. |
| 134 | 4-fluoro | 2-phenyl | ESIMS: m/z 466 (M + H)$^+$. |
| 135 | 4-fluoro | 2-(3-chloro-phenyl) | ESIMS: m/z 500 [(M + H)$^+$, $^{35}$Cl], 502 [(M + H)$^+$, $^{37}$Cl]. |
| 136 | 4-fluoro | 2-(3-fluoro-phenyl) | ESIMS: m/z 484 (M + H)$^+$. |
| 137 | 4-fluoro | 2-(3-trifluoro-methyl-phenyl) | ESIMS: m/z 534 (M + H)$^+$. |
| 138 | 4-nitro | 2-(3-trifluoro-methyl-phenyl) | ESIMS: m/z 561 (M + H)$^+$. |
| 139 | 4-tri-fluoro-methyl | 2-(3-trifluoro-methyl-phenyl) | ESIMS: m/z 584 (M + H)$^+$. |

Example 140

Isoquinoline-5-sulfonic acid {2-[2-(5,2'-difluoro-biphenyl-2-yloxy)-ethylamino]-ethyl}-amide di-hydrochloric acid

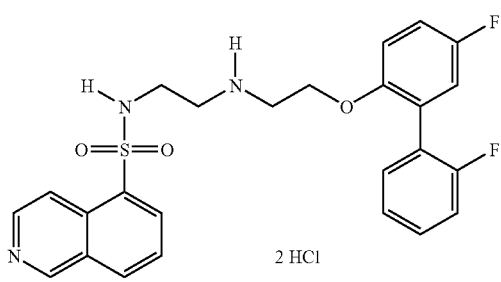

Aqueous sodium carbonate (0.18 mL, 2.0 M) is added to a stirred solution of [2-(2-bromo-4-fluoro-phenoxy)-ethyl]-[2-(isoquinoline-5-sulfonylamino)-ethyl]-carbamic acid tert-butyl ester (0.101 g, 0.179 mmol), 2-fluorophenyl boronic acid (26 mg, 0.19 mmol), Pd(dppb)$_2$Cl$_2$ (43 mg, 0.072 mmol) in DMF (3 mL)/MeOH (0.8 mL). The resultant mixture is heated at 80° C. under argon for 16 hours. At ambient temperature ethyl acetate (10 mL) and brine (3 mL) are added to the mixture, the organic layer is separated, dried, filtered and concentrated. After MPLC separation on silica (gradient 0-1% methanol in methylene chloride), 90 mg (86% yield) of the BOC-protected title compound is obtained. The precursor is dissolved in methylene chloride (10 mL), then a small stream of anhydrous HCl gas is bubbled through the solution for 1 minute. The solution is capped with a glass stopper and allowed to stir for 1 hour to form a suspension. After filtration and drying, 70 mg (86% yield) of the title compound is obtained as a solid. ESIMS: m/z 484 (M+H)$^+$.

Using a method similar to the preparation of example 140, with isoquinoline-5-sulfonic acid {2-[2-(2-bromo-4-chloro-phenyloxy)-ethylamino]-ethyl}-amide as starting material, the following compounds may be prepared as di- or tri-hydrochloride salts.

| Ex. # | R | Data |
|---|---|---|
| 141 | 2'-OH | ESIMS: m/z 498 [(M + H)$^+$, $^{35}$Cl], 500 [(M + H)$^+$, $^{37}$Cl]. |
| 142 | 3'-OH | ESIMS: m/z 498 [(M + H)$^+$, $^{35}$Cl], 500 [(M + H)$^+$, $^{37}$Cl]. |
| 143 | 4'-OH | ESIMS: m/z 498 [(M + H)$^+$, $^{35}$Cl], 500 [(M + H)$^+$, $^{37}$Cl]. |
| 144 | 3'-NH$_2$ | ESIMS: m/z 497 [(M + H)$^+$, $^{35}$Cl], 499 [(M + H)$^+$, $^{37}$Cl]. |
| 145 | 4'-NH$_2$ | ESIMS: m/z 497 [(M + H)$^+$, $^{35}$Cl], 499 [(M + H)$^+$, $^{37}$Cl]. |
| 146 | 2'-methoxy | ESIMS: m/z 512 [(M + H)$^+$, $^{35}$Cl], 514 [(M + H)$^+$, $^{37}$Cl]. |
| 147 | 3'-methoxy | ESIMS: m/z 512 [(M + H)$^+$, $^{35}$Cl], 514 [(M + H)$^+$, $^{37}$Cl]. |
| 148 | 4'-methoxy | ESIMS: m/z 512 [(M + H)$^+$, $^{35}$Cl], 514 [(M + H)$^+$, $^{37}$Cl]. |
| 149 | 3'-(morpholinocarbonyl) | ESIMS: m/z 595 [(M + H)$^+$, $^{35}$Cl], 597 [(M + H)$^+$, $^{37}$Cl]. |
| 150 | 4'-(morpholinocarbonyl) | ESIMS: m/z 595 [(M + H)$^+$, $^{35}$Cl], 597 [(M + H)$^+$, $^{37}$Cl]. |
| 151 | 3'-(hydroxycarbonyl) | ESIMS: m/z 526 [(M + H)$^+$, $^{35}$Cl], 528 [(M + H)$^+$, $^{37}$Cl]. |
| 152 | 4'-(hydroxycarbonyl) | ESIMS: m/z 526 [(M + H)$^+$, $^{35}$Cl], 528 [(M + H)$^+$, $^{37}$Cl]. |
| 153 | 4'-(isopropyl-aminocarbonyl) | ESIMS: m/z 567 [(M + H)$^+$, $^{35}$Cl], 569 [(M + H)$^+$, $^{37}$Cl]. |

Using a method similar to Example 34, with the appropriate starting materials, the following compounds may be prepared as dihydrochloride salts.

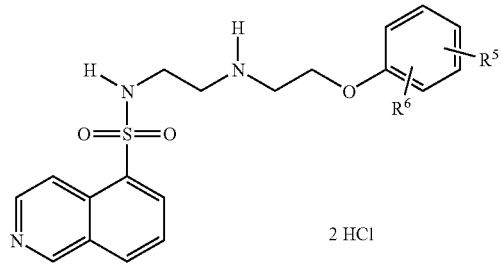

| Ex. # | R⁵ | R⁶ | Data |
|---|---|---|---|
| 154 | 4-fluoro | 2-(3-nitro-phenyl) | ESIMS: m/z 511 (M + H)⁺. |
| 155 | 4-chloro | 2-(3-nitro-phenyl) | ESIMS: m/z 527 [(M + H)⁺, ³⁵Cl], 529 [(M + H)⁺, ³⁷Cl]. |
| 156 | 4-chloro | 2-(4-nitro-phenyl) | ESIMS: m/z 527 [(M + H)⁺, ³⁵Cl], 529 [(M + H)⁺, ³⁷Cl]. |
| 157 | 4-tri-fluoro-methyl | 2-(3-nitro-phenyl) | ESIMS: m/z 561 (M + H)⁺. |

Example 158

7-Phenyl-isoquinoline-5-sulfonic acid {2-[2-(4-chloro-2-(4-methoxy-phenyl)-phenoxy)-ethylami-ethyl}-amide

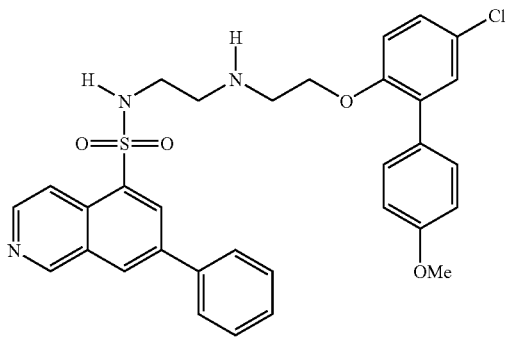

Using a procedure analogous to Example 79, the title compound is obtained, as a white powder. ESIMS: m/z 588 [(M+H)⁺, ³⁵Cl], 590 [(M+H)⁺, ³⁷Cl].

Example 159

7-(3-Hydroxy-phenyl)-isoquinoline-5-sulfonic acid {2-[2-(4-chloro-phenoxy)-ethylamino]-ethyl}-amide di-hydrochloric acid

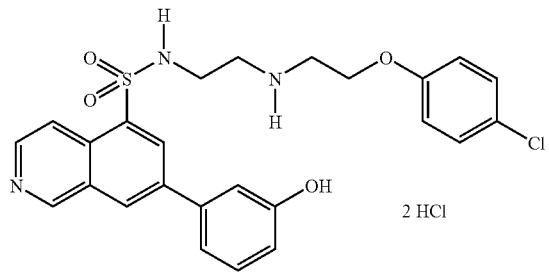

Using a procedure analogous to example 140, with [2-(7-bromo-isoquinoline-5-sulfonylamino)-ethyl]-[2-(4-chloro-phenoxy)-ethyl]-carbamic acid tert-butyl ester as starting material, the title compound is obtained as a yellow powder. ESIMS: m/z 498 [(M+H)⁺, ³⁵Cl], 500 [(M+H)⁺, ³⁷Cl].

Example 160

7-(3-Hydroxy-phenyl)-isoquinoline-5-sulfonic acid {2-[2-(4-chloro-phenoxy)-ethylamino]-ethyl}-methyl-amide di-hydrochloric acid

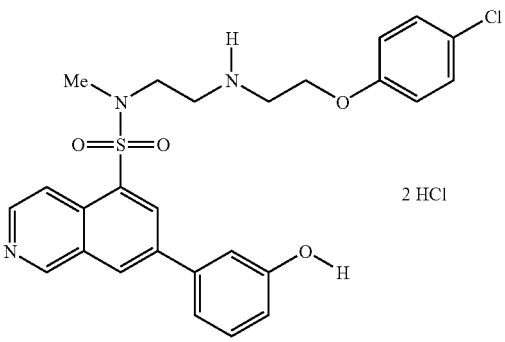

Using a procedure analogous to the preparation of example 140, with (2-[(7-bromo-isoquinoline-5-sulfonyl)-methyl-amino]-ethyl)-[2-(4-chloro-phenoxy)-ethyl]-carbamic acid tert-butyl ester as starting material, the title compound is obtained as a yellow solid. ESIMS: m/z 512 [(M+H)⁺, ³⁵Cl], 514 [(M+H)⁺, ³⁷Cl].

Example 161

7-(3-Hydroxy-phenyl)-isoquinoline-5-sulfonic acid (2-dimethylamino-ethyl)-{2-[2-(4-nitro-phenoxy)-ethylamino]-ethyl}-amide tri-hydrochloric acid

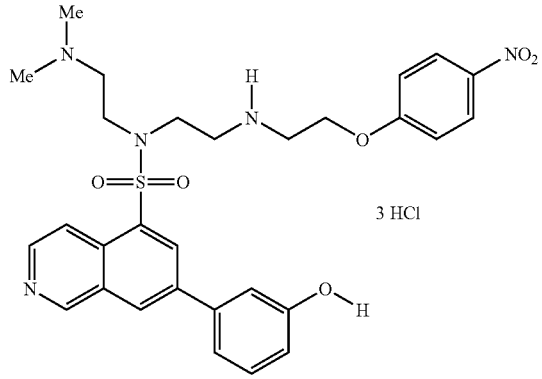

Using a procedure analogous to the preparation of example 160, the title compound is obtained as a yellow solid. ESIMS: m/z 580 (M+H)⁺.

Example 162

7-(3-Hydroxy-phenyl)-isoquinoline-5-sulfonic acid {2-[3-(2-benzyl-4-chloro-phenoxy)-propylam-ethyl}-amide di-hydrochloric acid

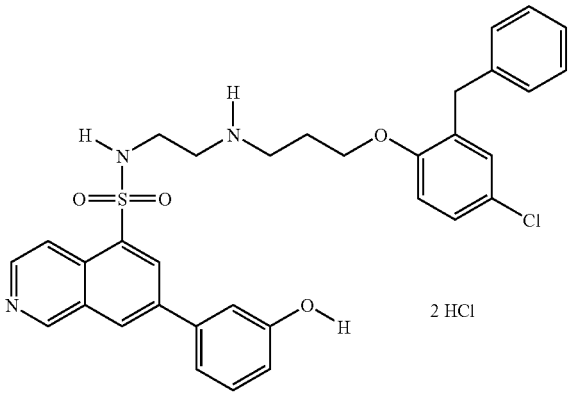

Using a procedure analogous to Example 117, with 7-(3-hydroxy-phenyl)-isoquinoline-5-sulfonic acid (2-{[3-(2-benzyl-4-chloro-phenoxy)-propyl]-[bis-(4-methoxy-phenyl)-methyl]-amino}-ethyl)-amide as starting material, the title compound is obtained as a yellow foam. ESIMS: m/z 602 [(M+H)$^+$, $^{35}$Cl], 604 [(M+H)$^+$, $^{37}$Cl].

Using a procedure similar to that described in Example 96, with the appropriate starting materials, the following compounds may be prepared as the hydrochloride salts.

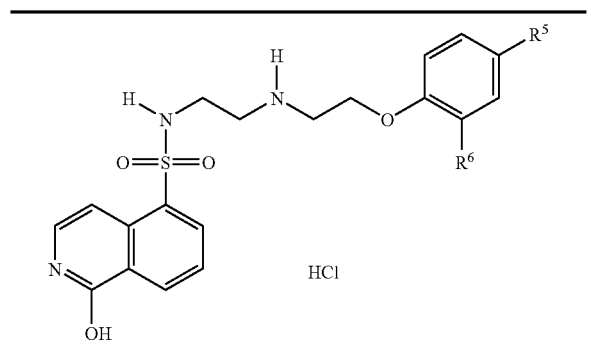

| Ex. # | R$^5$ | R$^6$ | Data |
|---|---|---|---|
| 163 | fluoro | Phenyl | ESIMS: m/z 482 (M + H)$^+$. |
| 164 | fluoro | 3-chloro-phenyl | ESIMS: m/z 516 [(M + H)$^+$, $^{35}$Cl], 518 [(M + H)$^+$, $^{37}$Cl]. |
| 165 | chloro | 3-(phenyl)-phenyl | ESIMS: m/z 574 [(M + H)$^+$, $^{35}$Cl], 576 [(M + H)$^+$, $^{37}$Cl]. |
| 166 | trifluoromethyl | 3-fluoro-phenyl | ESIMS: m/z 550 (M + H)$^+$. |
| 167 | methyl | 3-trifluoromethyl-phenyl | ESIMS: m/z 546 (M + H)$^+$. |
| 168 | nitro | 2-chloro-phenyl | ESIMS: m/z 543 [(M + H)$^+$, $^{35}$Cl], 545 [(M + H)$^+$, $^{37}$Cl]. |

Using a procedure similar to that described in Example 111, with the appropriate starting materials, the following compounds may be prepared as the hydrochloride salts.

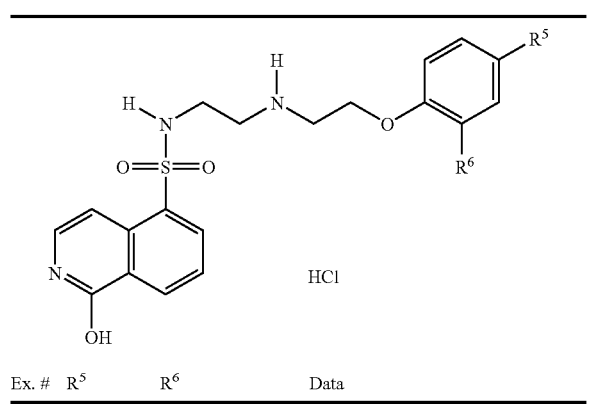

| Ex. # | R$^5$ | R$^6$ | Data |
|---|---|---|---|
| 169 | H | 3-trifluoromethyl-phenyl | ESIMS: m/z 532 (M + H)$^+$. |
| 170 | H | phenoxy | ESIMS: m/z 480 (M + H)$^+$. |
| 171 | fluoro | 3-fluoro-phenyl | ESIMS: m/z 500 (M + H)$^+$. |
| 172 | fluoro | 3-trifluoromethyl-phenyl | ESIMS: m/z 550 (M + H)$^+$. |

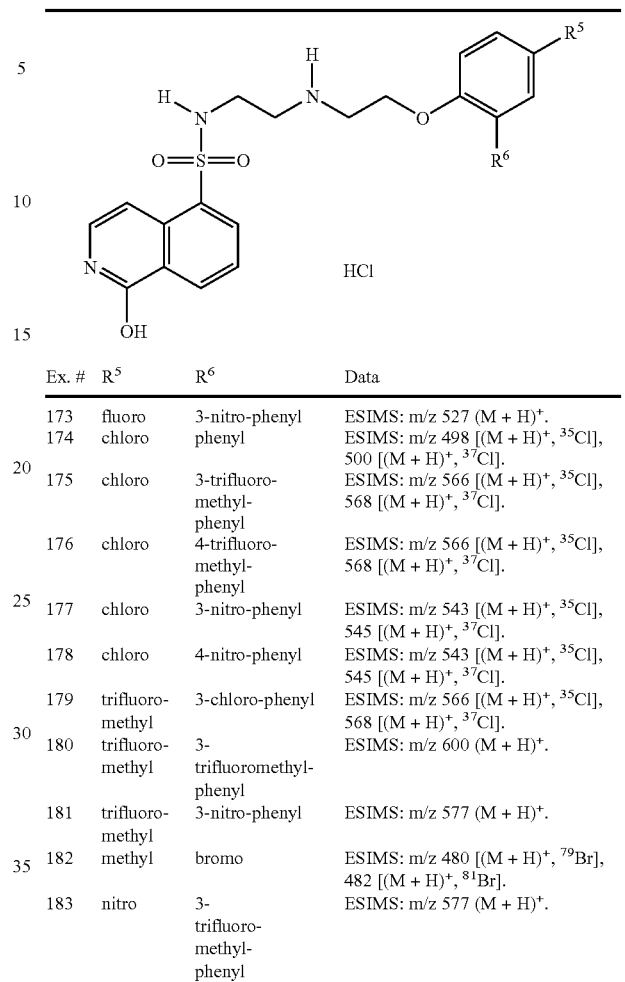

| Ex. # | R$^5$ | R$^6$ | Data |
|---|---|---|---|
| 173 | fluoro | 3-nitro-phenyl | ESIMS: m/z 527 (M + H)$^+$. |
| 174 | chloro | phenyl | ESIMS: m/z 498 [(M + H)$^+$, $^{35}$Cl], 500 [(M + H)$^+$, $^{37}$Cl]. |
| 175 | chloro | 3-trifluoromethyl-phenyl | ESIMS: m/z 566 [(M + H)$^+$, $^{35}$Cl], 568 [(M + H)$^+$, $^{37}$Cl]. |
| 176 | chloro | 4-trifluoromethyl-phenyl | ESIMS: m/z 566 [(M + H)$^+$, $^{35}$Cl], 568 [(M + H)$^+$, $^{37}$Cl]. |
| 177 | chloro | 3-nitro-phenyl | ESIMS: m/z 543 [(M + H)$^+$, $^{35}$Cl], 545 [(M + H)$^+$, $^{37}$Cl]. |
| 178 | chloro | 4-nitro-phenyl | ESIMS: m/z 543 [(M + H)$^+$, $^{35}$Cl], 545 [(M + H)$^+$, $^{37}$Cl]. |
| 179 | trifluoromethyl | 3-chloro-phenyl | ESIMS: m/z 566 [(M + H)$^+$, $^{35}$Cl], 568 [(M + H)$^+$, $^{37}$Cl]. |
| 180 | trifluoromethyl | 3-trifluoromethyl-phenyl | ESIMS: m/z 600 (M + H)$^+$. |
| 181 | trifluoromethyl | 3-nitro-phenyl | ESIMS: m/z 577 (M + H)$^+$. |
| 182 | methyl | bromo | ESIMS: m/z 480 [(M + H)$^+$, $^{79}$Br], 482 [(M + H)$^+$, $^{81}$Br]. |
| 183 | nitro | 3-trifluoromethyl-phenyl | ESIMS: m/z 577 (M + H)$^+$. |

Example 184

1-Hydroxy-isoquinoline-5-sulfonic acid {2-[2-(2-bromo-4-chloro-phenoxy)-ethylamino]-ethyl}-amide

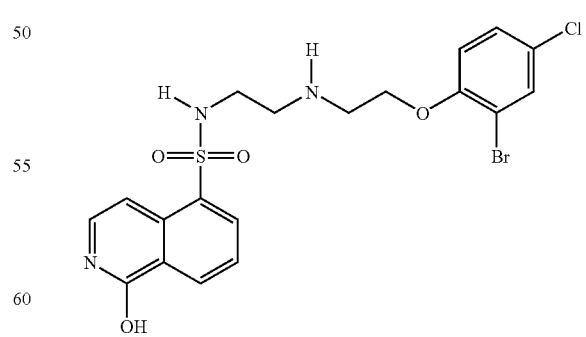

Using a procedure analogous to Example 111, the title compound is obtained as a white solid. ESIMS: m/z 500 [(M+H)$^+$, $^{35}$Cl, $^{79}$Br], 502 [(M+H)$^+$, $^{37}$Cl, $^{79}$Br or $^{35}$Cl, $^{81}$Br], 504 [(M+H)$^+$, $^{37}$Cl, $^{81}$Br].

Example 185

1-Hydroxy-isoquinoline-5-sulfonic acid {2-[2-(5-chloro-4'-fluoro-biphenyl-2-yloxy)-ethyla -ethyl}-amide

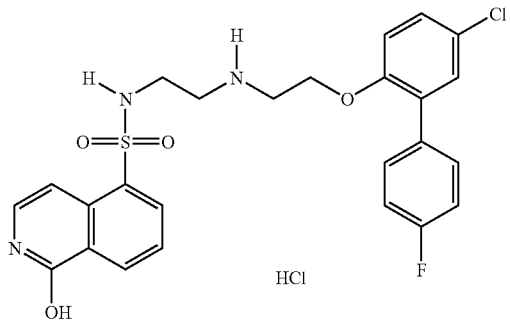

Using a procedure analogous to the preparation of Example 140, with [2-(5-chloro-4'-fluoro-biphenyl-2-yloxy)-ethyl]-[2-(1-hydroxy-isoquinoline-5-sulfonylamino)-ethyl]-carbamic acid tert-butyl ester as starting material, the title compound is obtained as a white solid. ESIMS: m/z 516 [(M+H)⁺, ³⁵Cl], 518 [(M+H)⁺, ³⁷Cl].

Using a method similar to the preparation of Example 185, with the appropriate starting material, the following compounds may be prepared as hydrochloride salt.

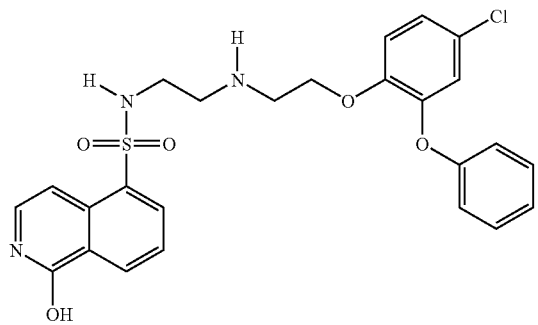

| Ex. # | R¹ | R² | Data |
|---|---|---|---|
| 186 | chloro | 4'-chloro | ESIMS: m/z 532 [(M + H)⁺, ³⁵Cl, ³⁵Cl], 534 [(M + H)⁺, ³⁵Cl, ³⁷Cl], 536 [(M + H)⁺, ³⁷Cl, ³⁷Cl]. |
| 187 | Methyl | 3'-trifluoromethyl | ESIMS: m/z 546 (M + H)⁺. |

Example 188

1-Hydroxy-isoquinoline-5-sulfonic acid {2-[2-(4-chloro-2-phenoxy-phenoxy)-ethylamino]-ethyl}-amide

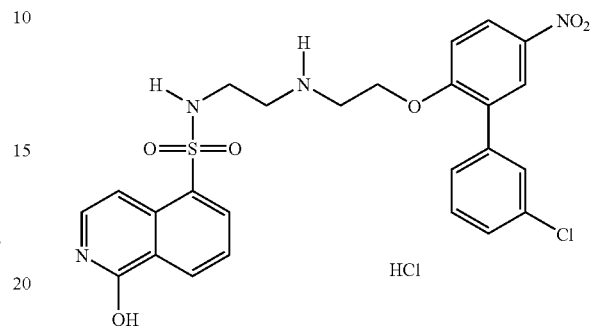

Using a procedure analogous to Example 111, the title compound is obtained as a white powder. ESIMS: m/z 514 [(M+H)⁺, ³⁵Cl], 516 [(M+H)⁺, ³⁷Cl].

Example 189

1-Hydroxy-isoquinoline-5-sulfonic acid {2-[2-(3'-chloro-5-nitro-biphenyl-2-yloxy)-ethylam -ethyl)-amide hydrochloric acid

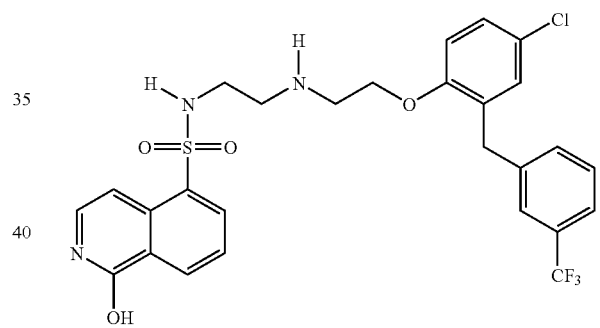

Using a procedure analogous to Example 96, the title compound is obtained as a white powder. ESIMS: m/z 543 [(M+H)⁺, ³⁵Cl], 545 [(M+H)⁺, ³⁷Cl].

Example 190

1-Hydroxy-isoquinoline-5-sulfonic acid (2-{2-[4-chloro-2-(3-trifluoromethyl-benzyl)-phenoxy -ethylamino}-ethyl)-amide

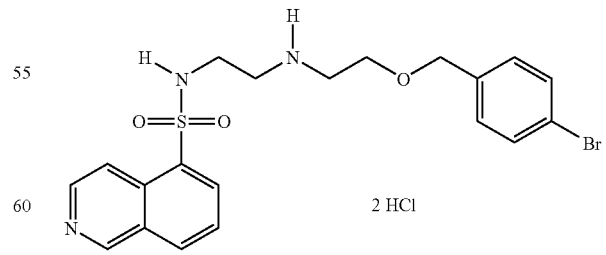

Using a procedure analogous to Example 111, the title compound is obtained as a white foam. ESIMS: m/z 580 [(M+H)⁺, ³⁵Cl], 582 [(M+H)⁺, ³⁷Cl].

Example 191

Isoquinoline-5-sulfonic acid {2-[2-(4-bromo-benzyloxy)-ethylamino]-ethyl}-amide di-hydrochloric acid Using a procedure analogous to Example 34 (see preparation 116), reductive amination of (4-bromo-benzyloxy)-acetaldehyde with isoquinoline-5-sulfonic acid (2-aminoethyl)-amide gives the title compound as a white solid. ESIMS: m/z 464 [(M+H)⁺, ⁷⁹Br], 466 [(M+H)⁺, ⁸¹Br].

Using a procedure similar to that described in Example 114, with the appropriate starting materials, the following compounds may be prepared as the hydrochloride salts.

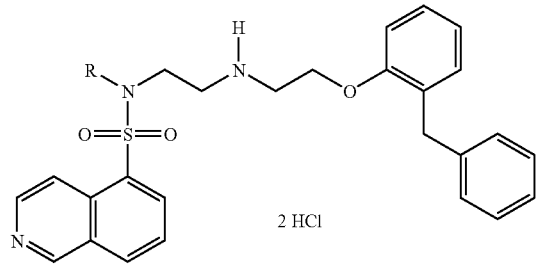

| Ex. # | R | Data |
|---|---|---|
| 192 | ethyl | ESIMS: m/z 490 (M + H)+. |
| 193 | 2,2,2-trifluoro-ethyl | ESIMS: m/z 544 (M + H)+. |
| 194 | propen-3-yl | ESIMS: m/z 502 (M + H)+. |
| 195 | 2-(methyl)-propen-3-yl | ESIMS: m/z 516 (M + H)+. |
| 196 | benzyl | ESIMS: m/z 552 (M + H)+. |
| 197 | methoxycarbonylmethyl | ESIMS: m/z 534 (M + H)+. |

Example 198

2-[(2-[2-(2-Benzyl-phenoxy)-ethylamino]-ethyl}-(isoquinoline-5-sulfonyl)-amino]-acetamide di-oxalic acid

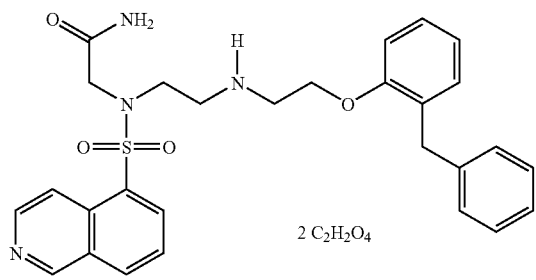

Using a procedure analogous to Example 114, the free amine product is obtained as a gum and subsequently converted to di-oxalic acid salt as a yellow solid. ESIMS: m/z 519 (M+H)+.

Example 199

Isoquinoline-5-sulfonic acid {2-[2-(4-trifluoromethyl-phenylsulfanyl)-ethylamino]-ethyl}-amide di-hydrochloric acid

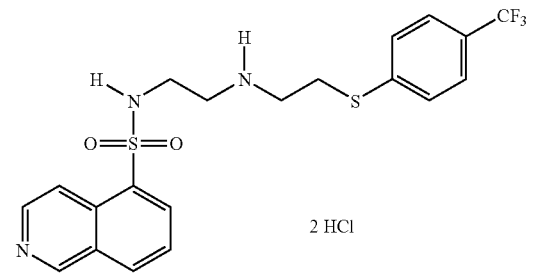

Using a procedure analogous to Example 121, the title compound is obtained as a tan solid. ESIMS: m/z 456 (M+H)+.

Example 200

1-Hydroxy-isoquinoline-5-sulfonic acid {2-[2-(4-bromo-phenylsulfanyl)-ethylamino]-ethyl}-amide hydrochloric acid

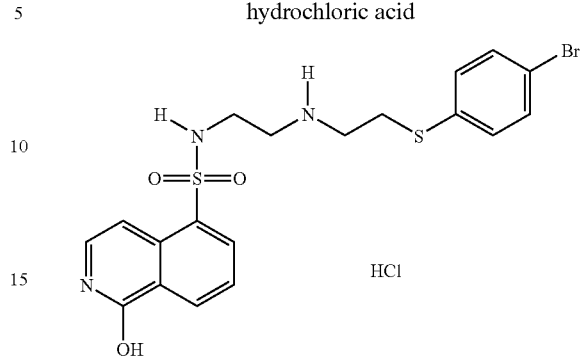

Using a procedure analogous to Example 96, the title compound is obtained as a tan solid. ESIMS: m/z 482 [(M+H)+, 79Br], 484 [(M+H)+, 81Br].

Using a procedure similar to that described in Example 123, with the appropriate starting materials, the following compounds may be prepared as the oxalate salts.

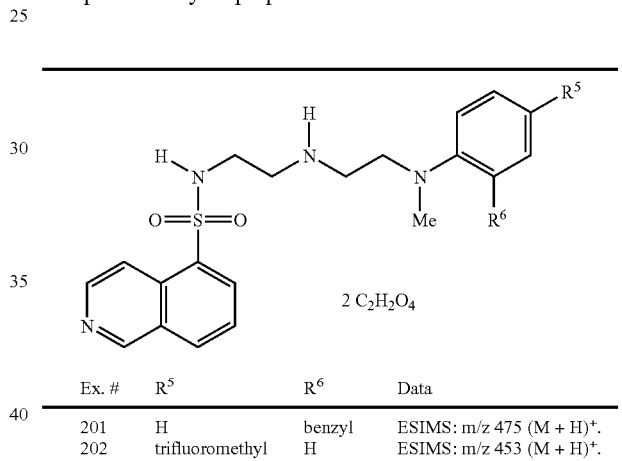

| Ex. # | $R^5$ | $R^6$ | Data |
|---|---|---|---|
| 201 | H | benzyl | ESIMS: m/z 475 (M + H)+. |
| 202 | trifluoromethyl | H | ESIMS: m/z 453 (M + H)+. |

Example 203

(4-Bromo-phenyl)-{2-[2-(isoquinoline-5-sulfonylamino)-ethylamino]-ethyl}-carbamic acid tert-butyl ester

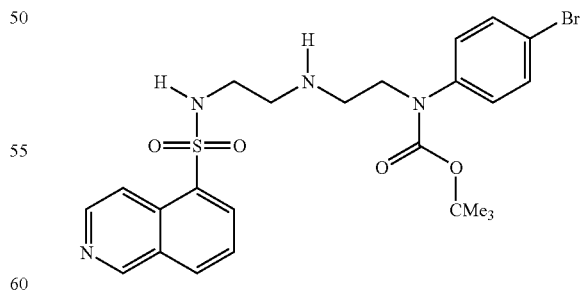

By following similar procedure as described in Example 1, DIBAL-H reduction of [(4-bromo-phenyl)-tert-butoxycarbonyl-amino]-acetic acid methyl ester (aqueous Rochelle's salt work-up) and subsequent reductive amination with isoquinoline-5-sulfonic acid (2-amino-ethyl)-amide gives the free amine product as a solid (71% yield). ESIMS: m/z 549 [(M+H)+, 79Br], 551 [(M+H)+, 81Br].

Example 204

Isoquinoline-5-sulfonic acid {2-[2-(4-bromo-phenylamino)-ethylamino]-ethyl}-amide tri-hydrochloric acid

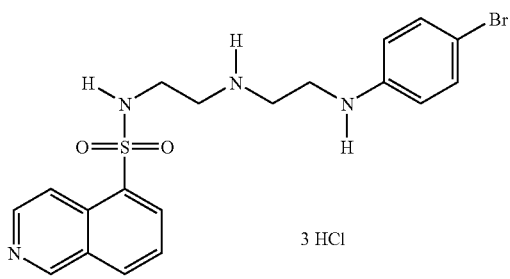

3 HCl

A 1N HCl in diethyl ether solution (3 mL) is added to a stirred solution of (4-bromo-phenyl)-{2-[2-(isoquinoline-5-sulfonylamino)-ethylamino]-ethyl}-carbamic acid tert-butyl ester (138 mg, 0.251 mmol) in methylene chloride (3 mL). The mixture is allowed to stir for 4 hours to form a suspension. After concentration, methylene chloride (3 mL) is added to the solid. The suspension is sonicated and filtered to give 124 mg (89% yield) of the title compound as a solid. ESIMS: m/z 449 [(M+H)$^+$, $^{79}$Br], 451 [(M+H)$^+$, $^{81}$Br].

Example 205

Isoquinoline-5-sulfonic acid (2-{2-[benzyl-(4-bromo-phenyl)-amino]-ethylamino}-ethyl)-amide di-oxalic acid

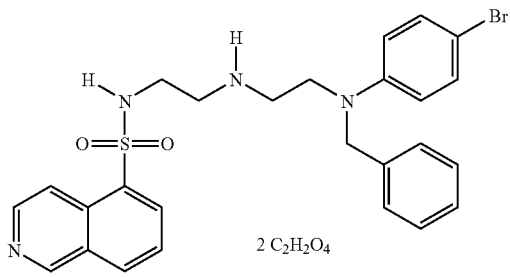

2 C$_2$H$_2$O$_4$

Using a procedure analogous to Example 123, the title compound is obtained as a yellowish solid. ESIMS: m/z 539 [(M+H)$^+$, $^{79}$Br], 541 [(M+H)$^+$, $^{81}$Br].

Example 206

1-Hydroxy-isoquinoline-5-sulfonic acid (2-{2-[methyl-(4-trifluoromethyl-phenyl)-amino]-ethylamino}-di-hydrochloric acid

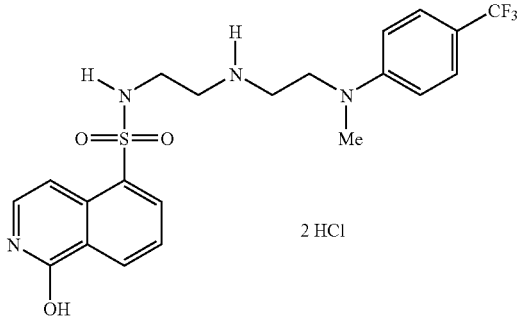

2 HCl

Using a procedure analogous to Example 96, the title compound is obtained as a yellowish solid. ESIMS: m/z 469 (M+H)$^+$.

The following compounds were made according to the procedures shown in

Preparation 118

| Ex. # | Compound Name | R$^1$ | R$^2$ | Data |
|---|---|---|---|---|
| 207 | Isoquinoline-5-sulfonic acid-(2-{2-[2-(morpholine-4-carbonyl)-phenoxy]-ethylamino-ethyl)-amide | H | H | ESIMS: m/z 485 [M + H]$^+$. |
| 208 | 7-Phenyl-isoquinoline-5-sulfonic acid-(2-{2-[2-(morpholine-4-carbonyl)-phenoxy]-ethylamino-ethyl)-amide | H | phenyl | ESIMS: m/z 561 [M + H]$^+$. |
| 209 | Isoquinoline-5-sulfonic acid-(2-{2-[4-chloro-2-(morpholine-4-carbonyl)-phenoxy]-ethylamino-ethyl)-amide | Cl | H | ESIMS: m/z 519 |
| 210 | 7-Phenyl-isoquinoline-5-sulfonic acid-(2-{2-[4-chloro-2-(morpholine-4-carbonyl)-phenoxy]-ethylamino-ethyl)-amide dihydrochloride | Cl | phenyl | ESIMS: m/z 595 [M + H]$^+$. |

The following compounds were made according to the procedures shown in

Preparation 119

| Ex. # | Compound Name | R4 | R7 | R1 | Data |
|---|---|---|---|---|---|
| 211 | Isoquinoline-5-sulfonic acid-{2-[2-(2-morpholin-4-ylmethyl-phenoxy)-ethylamino]-ethyl-amide trihydrochloride | H | H | H | ESIMS: m/z 471 [M + H]$^+$. |

-continued

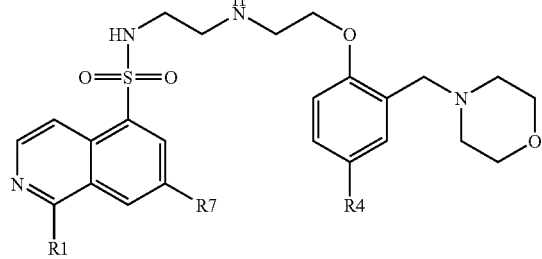

| Ex. # | Compound Name | R4 | R7 | R1 | Data |
|---|---|---|---|---|---|
| 212 | 7-Phenyl-isoquinoline-5-sulfonic acid-{2-[2-(2-morpholin-4-ylmethyl-phenoxy)-ethylamino]-ethyl}-amide trihydrochloride | H | Phenyl | H | ESIMS: m/z 547 [M + H]+. |
| 213 | 1-Hydroxy-isoquinoline-5-sulfonic acid-{2-[2-(2-morpholin-4-ylmethyl-phenoxy)-ethylamino]-ethyl}-amide dihydrochloride | H | H | OH | ESIMS: m/z 487 [M + H]+. |
| 214 | Isoquinoline-5-sulfonic acid-{2-[2-(4-chloro-2-morpholin-4-ylmethyl-phenoxy)-ethylamino]ethyl}-amide trihydrochloride | Cl | H | H | ESIMS: m/z 505 [M + H]+. |
| 215 | 7-Phenyl-isoquinoline-5-sulfonic acid-{2-[2-(2-morpholin-4-ylmethyl-phenoxy)-ethylamino]-ethyl}-amide trihydrochloride | Cl | Phenyl | H | ESIMS: m/z 581 [M + H]+. |

Example 216

1-Chloro-isoquinoline-5-sulfonic acid {2-[2-(5-chloro-3'-methylsulfonylamino-biphenyl-2-yloxy)-ethylamino]-ethyl}-amide di-hydrochloride

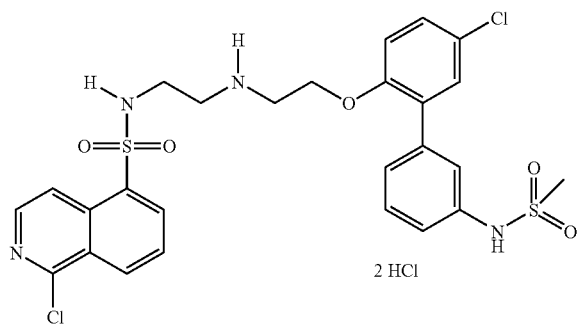

1-Chloro-5-(ethylenediaminesulfonamido)-isoquinoline-HCl salt (107 mg, 0.3 mmol) was dissolved in CH$_2$Cl$_2$/MeOH (15 ml, 5:1). Triethylamine (87 mg, 0.8 mmol), and N-[5'-Chloro-2'-(2-oxo-ethoxy)-biphenyl-3-yl]-methanesulfonamide (122 mg, 0.36 mmol) were added successively at room temperature. The mixture was stirred overnight. The resulting imine was reduced with sodium borohydride (50 mg, 1.3 mmol). After two hours, the reaction was concentrated under reduced pressure. The residue was diluted with water and ethyl acetate. The water phase was extracted with ethyl acetate and the combined organic layer was washed with brine and concentrated. Column-chromatography on silicagel afforded the desired compound (55 mg, 30% yield). ESIMS: m/z 609 [(M+H)+, $^{35}$Cl], 611 [(M+H)+, $^{37}$Cl].

Example 217

7-Phenyl-isoquinoline-5-sulfonic acid-{2-[2-(4-methylsulfonyl-phenoxy)-ethylamino-propyl}-amide,

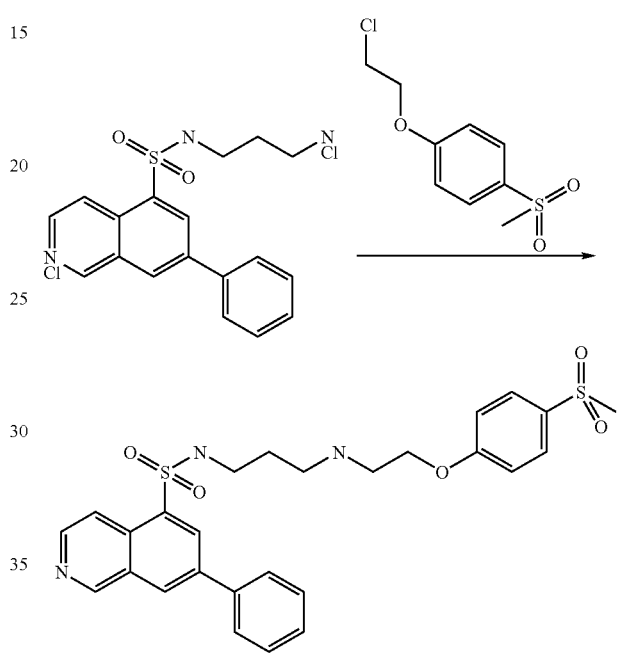

A mixture of amine (HCl salt) (200 mg, 0.5 mmol) and chloride (167.35 mg, 0.5 mmol) in DMF (3.0 mL)/Et$_3$N (0.2 mL) was heated to 60° C. with stirring for 48 hours. It was diluted with CH$_3$OH and passed prewashed SCX column, which was washed with a mixture of CH$_3$OH/CH$_2$Cl$_2$ (1:1), then NH$_3$ (2.0 M in CH$_3$OH) and concentrated. The residue was subjected to HPLC purification to 27.4 mg of the white solid.

$^1$H NMR (DMSO-d$_6$, 400 MHz) δ: 2.56 (2H, t, J=5.15 Hz), 2.71 (2H, t, J=5.71 Hz), 2.98 (2H, t, J=6.15 Hz), 3.17 (3H, s), 3.93 (2H, t, J=5.71 Hz), 7.07 (2H, d, J=8.79 Hz), 7.51 (1H, t, J=7.47 Hz), 7.60 (2H, t, J=7.47 Hz), 7.83 (2H, d, J=9.67 Hz), 7.90 (2H, d, J=8.79 Hz), 8.49 (1H, d, 3=6.15 Hz), 8.62 (1H, d, J=1.76 Hz), 8.71 (1H, d, J=5.71 Hz), 8.76 (1H, d, J=0.88 Hz), 9.55 (1H, d, J=0.88 Hz).

IS-MS, m/e 526.65 (m+1)

The compounds of the present invention can be administered alone or in the form of a pharmaceutical composition, that is, combined with pharmaceutically acceptable carriers, or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, for purposes of stability, convenience of crystallization, increased solubility, and the like.

Thus, the present invention provides pharmaceutical compositions comprising a compound of the Formula (I) and a pharmaceutically acceptable diluent.

The compounds of Formula (I) can be administered by a variety of routes. In effecting treatment of a patient afflicted with disorders described herein, a compound of Formula (I) can be administered in any form or mode that makes the compound bioavailable in an effective amount, including oral and parenteral routes. For example, compounds of Formula (I) can be administered orally, by inhalation, or by the subcutaneous, intramuscular, intravenous, transdermal, intranasal, rectal, occular, topical, sublingual, buccal, or other routes. Oral administration is generally preferred for treatment of the disorders described herein. However, oral administration is not the only preferred route. For example, the intravenous route may be preferred as a matter of convenience or to avoid potential complications related to oral administration. When the compound of Formula (I) is administered through the intravenous route, an intravenous bolus or slow infusion is preferred.

One skilled in the art of preparing formulations can readily select the proper form and mode of administration depending upon the particular characteristics of the compound selected, the disorder or condition to be treated, the stage of the disorder or condition, and other relevant circumstances. (Remington's Pharmaceutical Sciences, 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as povidone, hydroxypropyl cellulose, microcrystalline cellulose, gum tragacanth or gelatin; excipients such as dicalcium phosphate, starch, or lactose; disintegrating agents such as alginic acid, Primogel, corn starch and the like; lubricants such as talc, hydrogenated vegetable oil, magnesium stearate or Sterotex; glidants such as colloidal silicon dioxide; and sweetening agents, such as sucrose, aspartame, or saccharin, or a flavoring agent, such as peppermint, methyl salicylate or orange flavoring, may be added. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, coatings. Thus, tablets or pills may be coated with sugar, shellac, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

The compounds of Formula (I) are inhibitors of Akt1 activity. The inhibitory activity of the compounds of Formula (I) may be demonstrated by the methods below.

Akt1 Phosphorylation Assay

The assay described measures the phosphorylation of Crosstide by active human Akt1 and other Akt isoforms. Crosstide contains a consensus sequence derived from Akt substrates GSK3b and forkhead transcription factors (FKs). The $^{33}$P-labeled Crosstide substrate is captured by phosphocellulose membrane filter plates.

Enzyme and Substrate

Active human recombinant Akt1 (full-length) purified from Sf9 insect cells is from Upstate Biotechnology, Inc. (Cat. #14-276, 405 µg/ml). Crosstide substrate, $NH_2$-GR-PRTSSFAEG-COOH (M.W.1164) is purchased from Multiple Peptide System (Cat. # L59/GR145-153).

Standard Assay Solutions

Solution (A): 20% DMSO (dimethylsulphoxide) or Compound in 20% DMSO; Solution (B): Assay Buffer Mix: 31.25 µM Crosstide, 37.5 mM $MgCl_2$, 87.5 mM HEPES, pH 7.3, 50 µM ATP γ-$^{33}$P-ATP, 0.05 µCi/µl; Solution (C): Akt Kinase Mix: 31.25 mM HEPES, pH 7.3; 1 mM DTT, 25 nM UBI Akt1.

Procedure for Phosphocellulose Filter-Binding Assay

Ten µl of Solution (A) are first mixed with 20 µl Solution (B). The enzymatic reaction is initiated by adding 20 µl Solution (C) to the mixture. (Final concentration or amount in a 50-µl reaction mix: 4% DMSO or various compound concentration in 4% DMSO; 12.5 µM Crosstide; 15 mM $MgCl_2$; 35 mM HEPES, pH7.3; 20 µM ATP; 1 µCi γ-$^{33}$P-ATP; 0.4 mM DTT; 10 nM UBI Akt1.) The reactions are performed in 96-well microtiter plates.

After 30 minutes at room temperature, the reaction is terminated by adding 80 µl of 10% $H_3PO_4$. An aliquot of 100 µl from each well is transferred to the phosphocellulose filter plate (Millipore MultiScreen, Catalog #MAPHN0B50). After 30 minutes, the reaction mix is filtered with a Millipore manifold following by 3 washes with 0.5% $H_3PO_4$ The filter is then vacuum-dried and the plate is fitted onto a Packard carrier. 100 µl/well Microscint20 are added and the contents are counted in a Packard Top Count. Representative compounds of Formula (I) selected from compounds described herein as EXAMPLES were tested in the above assay and were demonstrated to have $IC_{50}$ values of $\leq 2$ µM.

PKA Phosphorylation Assay

This procedure describes an assay for measuring the phosphorylation of Crosstide, which is a substrate for PKA, by active protein kinase A (PKA). The $^{33}$P-labeled Crosstide substrate is captured by phosphocellulose membrane filter plates;

Enzyme and Substrate

Active catalytic subunit of PKA purified from bovine heart is purchased from Sigma (Cat. # P2645). Crosstide substrate, $NH_2$-GRPRTSSFAEG-COOH (M.W. 1164), is from Multiple Peptide Systems (Cat. #L59/GR145-153).

Standard Assay Solutions

Solution (A): 20% DMSO or Compound in 20% DMSO; Solution (B): Assay Buffer Mix: 500 µM Crosstide, 25 mM $MgCl_2$, 150 mM HEPES, pH 7.3; 50 µM ATP, γ-$^{33}$P-ATP, 0.025 µCi/µl; Solution (C): PKA Kinase Mix: 25 mM Tris, pH 8; 0.01% Triton X-100; 0.1 mM EGTA, 2.5% glycerol; 0.125 mM DTT and 0.05 U/μl PKA.

Procedure for Phosphocellulose Filter-Binding Assay

Ten μl of Solution A are first mixed with 20 μl Solution B. The enzymatic reaction is initiated by adding 20 μl Solution C to the mixture. (Final concentration/amount in 50-μl reaction: 4% DMSO or various compound concentration; 200 μM Crosstide, 10 mM $MgCl_2$; 60 mM HEPES, pH 7.3; 20 μM ATP; 0.5 μCi γ-$^{33}$P ATP; 10 mM Tris, pH 8; 0.004% Triton X-100; 0.04 mM EGTA; 1% glycerol; 0.05 mM DT and 1 unit PKA). The reactions are performed in 96-well microtiter plates. After 30 minutes at room temperature, the reaction is terminated by adding 80 μl of 10% $H_3PO_4$. An aliquot of 100 μl from each well is transferred to the phosphocellulose filter plate (Millipore MultiScreen, Catalog #MAPHN0B50). After 30 minutes, the reaction mix is filtered with a Millipore manifold following by 3 washes with 0.5% $H_3PO4$. The filter is then vacuum-dried, and the plate is fitted onto a Packard carrier. 100 μl/well Microscint20 are added and the contents are counted in a Packard Top Count.

Cell-Based Target Inhibition Assay

As substrates of Akt, the family of forkhead transcription factors (FKs) includes three members: FKHRL1, FKHR and AFX. They share a high degree of sequence homology and are involved in the transcription of pro-apoptotic genes. There are three sites for phosphorylation by Akt: T32/S253/S315 in FKHRL1, T24/S256/S318 in FKHR and T28/S193/S258 in AFX. When phosphorylated, FKs are translocated from nucleus to cytoplasm, thus rendered non-functional.

The following experimental protocol is designed to validate the mechanism of action of Akt inhibitors in cells by measuring the level of inhibition of FK phosphorylation. Ideally, an Akt inhibitor should inhibit the level of FK phosphorylation in a dose-dependent manner, with little effect on the level of phospho-Akt, total Akt or total FE.

Akt1 activity requires phophorylation at residues T308 and S473. The status of phospho-S473 is used to monitor level of phospho-Akt. Complete inactivation of FK proteins as transcription factors requires phosphoryaltion of three sites, T32, S253 and S315. The status of phospho-T32 is used to monitor the level of phospho-FK in cells.

Procedure for the Immunoblot-Based Target Inhibition Assay in Cells

Cell Lines:

(a) Cancer cell lines with elevated phospho-Akt as a result of loss of PTEN activity. They include but are not limited to the following: breast cancer: MDA-MB-468, MDA-MB-436, HCT1937, and BT549 (PTEN–/–); prostate cancer: PC3, LNCaP and its derivatives, LN T1.16, LN T2.9 (PTEN–/–); glioblastoma: U87MG, DBTRG005MG (PTEN–/–). (b) Cancer cell lines with elevated phospho-Akt as a result of reduced PTEN activity. They include but are not limited to the following: Ovarian cancer: A2780 (PTEN+/–). (c) Cancer cell lines with deregulated PI3-kinase activity. They include but are not limited to the following: ovarian cancer: OVCAR3, SKOV3.

For mechanism-validation of the activity of an Akt inhibitor, MDA-MB-468 and U87MG are routinely used. A2780, LNCaP and PC3 have also been used in studies with select sets of Akt inhibitors and shown to respond similarly as MDA-MB-468. Other cell lines having features of (a), (b) and/or (c) above may also be used.

Antibodies:

Primary antibodies include anti-Akt antibody for total Akt (Cell Signaling, cat. # 9272), anti-phospho-S473 Akt (Cell Signaling, Cat. # 92711); anti-FKHRL1 (Upstate Biotechnology, Cat. # 06-951), anti-phospho-T32 FKHRL1 (Upstate Biotechnology, cat. #06-952). Goat anti-rabbit IgO (H+L)-HRP conjugate (BioRad, Cat. # 170-6515) is used as the secondary antibody.

Experimental Protocol:

(A) Treatment of Cells with Akt1 Inhibitors and Preparation of Cell Lysates:

Target cells (e.g. MDA-MB-468, U87MG, American Type Culture Collection, ATCC) from an exponentially growing culture are plated at $2 \times 10^6$ per 10-cm plate in 10 ml culture media and incubated at 37° C. On the day of treatment, the overnight culture media is replaced with 10 ml of fresh media. Serial dilutions of test compounds are made in 100% DMSO. The volume of each dilution added to the culture should be less than 50 μl so that final DMSO concentration does not exceed 0.5%. An equivalent volume of DMSO is added to the sham-treated control, and a positive control prepared in the same manner is also included. After 30 minutes of treatment, the media is removed. After washing with ice-cold PBS (phosphate-buffered saline), cells are lysed with 100 μl of RIPA buffer (50 mM TRIS pH 7.4, 150 mM NaCl, 1 mM EDTA, 1% NP-40, 0.25% sodium deoxycholate, 1 mM NaF, 1 mM $Na_2VO_4$, and Roche Protease Inhibitor Cocktail tablet, Cat. # 1.836170). After removal of the particular fraction, the protein concentration in the cytoplasmic extracts is determined using Pierce BCA assay in microtiter format with BSA as a standard. After adjusting protein concentration, aliquots of the cell lysates are mixed with 4× gel sample buffer (3:1) and stored in –80° C. freezer. (4× gel sample buffer contains 0.25M Tris-HCl, pH 6.8; 40% glycerol; 8% sodium dodecyl sulfate, 0.02% bromophenol blue; and 1.0M 2-mercaptoethanol)

(B) Electrophoresis and Immunoblotting Procedures:

After brief heating at 100° C., equal amounts of cell lysates in gel sample buffer are loaded on 8-16% gradient gels. Electrophoresis is performed by standard procedure. Separated proteins in the gels are transferred to 0.2-micron nitrocellulose membranes using Invitrogen Transfer Buffer (Invitrogen, Cat. #LC3675) adjusted to contain 20% methanol. The blots are blocked with 5% non-fat Carnation milk in TBS/Tween 20 and probed with the primary antibody diluted in 5% milk in TBS/Tween overnight at 4° C. After washings with TBS/Tween, the secondary antibody diluted in 5% milk in TBS/Tween 20 and incubated for 60 min at room temperature. The blots are washed with TBS/Tween and water, and then immersed in Pierce Super Signal West Durra Extended Duration chemiluminescent substrate (Pierce, Cat. # 34075), following vendor's procedure. X-ray films are then exposed to the blots for a short time (10-120 seconds). The intensity of the protein bands of interest is scanned with a Flour-S-Multilmager and quantityOne Software (BioRad).

In Vitro Anti-Proliferation Assay

This following assay measures quantitatively the effect of Akt1 inhibitors on the proliferation and survival of target-relevant human cancer cell lines in culture. The assay employs alamarBlue™ dye as an indicator of viable cells. The model cell lines chosen are those with elevated phospho-Akt activity that arises as a result of defects in the tumor suppressor, Pten.

Cell Lines:

(a) Cancer cell lines with elevated phospho-Akt as a result of loss of PTEN activity. They include but are not limited to the following: breast cancer: MDA-MB-468, MDA-MB-436, HCT1937, and BT549 (PTEN−/−); prostate cancer: PC3, LNCaP and its derivatives, LN T1.16, LN T2.9 (PTEN−/−); glioblastoma: U87MG, DBTRG005MG (PTEN−/−). (b) Cancer cell lines with elevated phospho-Akt as a result of reduced PTEN activity: They include but are not limit to the following: Ovarian cancer: A2780 (PTEN+/−) and (c) Cancer cell lines with deregulated PI3-kinase activity: They include but are not limited to the following: ovarian cancer: OVCAR3, SKOV3.

For the anti-proliferation studies with Akt1 inhibitors, MDA-MB-468 and U87MG are used routinely. The results from studies with both cell lines are usually in good accord. A2780, LNCaP and PC3 have also been used in studies with select sets of Akt inhibitors and shown to respond similarly as MDA-MB-468 and U87MG. Other cancer cell lines having features of (a), (b) and/or (c) above may also be used.

Procedure for alamarBlue™ Cell Proliferation Assay

Target cells (e.g. MDA-MB-468, U87MG) from an exponentially growing culture are plated at 5-10,000 cells/100 μl per well in a 96-well cell culture plate and incubated overnight at 37° C. in a CO₂ incubator. On the day of treatment, 100 μl of serially diluted test compounds are added to the cells in triplicate, with a final DMSO concentration not exceeding 0.5%. Samples containing DMSO only and a positive control prepared in a similar manner are included as controls. Cells are incubated in a CO₂ incubator at 37° C. for 72 hours. To measure viable cells quantitatively, 20 μl of alamarBlue™ (Trek Diagnostic Systems, Inc., cat. # 00-100) per well is added to the cells, and the incubation continues for 4-5 hours. (Other indicators for viable cells may also be used.) Fluorescence is measured with excitation wavelength at 595 nm in SpectraFluor Plus (TeCan Instruments).

In Vivo Tumor Growth Inhibition Assay

Tumor Models:
Xenografts derived from any of the following can be used: (a) Cancer cell lines with elevated phospho-Akt as a result of loss of PTEN activity. They include but are not limited to the following: breast cancer: MDA-MB-468, MDA-MBA-436, HCT1937, and BT549 (PTEN−/−); prostate cancer: PC3, LNCaP and its derivatives, LN T1.16, LN T2.9 (PTEN−/−); glioblastoma: U87MG, DBTRG005MG (PTEN−/−). (b) Cancer cell lines with elevated phospho-Akt as a result of reduced PTEN activity: They include but are not limit to the following: Ovarian cancer: A2780 (PTEN+/−) and (c) Cancer cell lines with dysregulated-PI3-kinase activity: They include but are not limited to the following: ovarian cancer: OVCAR3, SKOV3.

For the in vivo tumor growth inhibition studies, xenografts derived from U87MG are used routinely. A2780 xenografts have also been used. In addition, any in vivo tumor model having features of (a), (b) and/or (c) above may also be used.

Experimental Protocol for In Vivo Tumor Inhibition Studies

Approximately 5-10×10⁶ tumor cells are implanted subcutaneously into both flanks of CD1 nu/nu mice (or intraperitoneally, if appropriate) on Day-1. Treatment typically begins on Day-2. The inhibitor and vehicle are administered daily by intraperitoneal injection or by intravenous infusion. Body weight and tumor size are monitored every two days until tumors in the vehicle control group reach the size of 600-1000 mm³, typically 4-5 weeks after the tumor cells are implanted for the tumor cell lines used.

What is claimed is:
1. A compound of Formula (I):

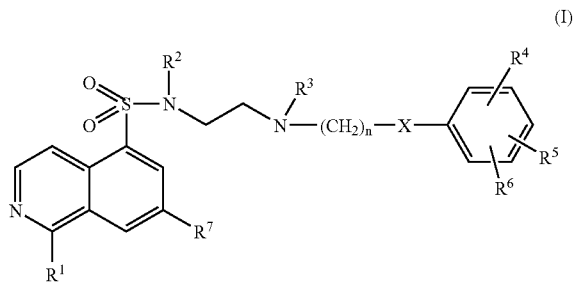

wherein:
R¹ is hydrogen, halo, amino or hydroxy;
R² is hydrogen, $C_1$-$C_4$ alkyl, or $C_2$-$C_4$ alkenyl,
  wherein said $C_1$-$C_4$ alkyl is optionally substituted with carboxyl, trifluoro, benzyl, acetamide, $C_1$-$C_4$ alkoxycarbonyl, substituted $C_1$-$C_4$alkoxycarbonyl, wherein the substitution is $C_1$-$C_2$ alkyl, or —$NR^9R^{10}$,
  wherein $R^9$ and $R^{10}$ are each independently hydrogen or $C_1$-$C_4$ alkyl;
R³ is hydrogen, or $C_1$-$C_4$ alkyl;
R⁴ is hydrogen, halo, $C_1$-$C_4$ alkyl, or $C_1$-$C_4$ alkoxy;
R⁵ is hydrogen, halo, $C_1$-$C_4$ alkyl, $C_1$-$C_4$ alkoxy, trifluoromethyl, or nitro, or R⁴ and R⁵, together with the carbon atoms to which they are attached, form a benzo-fused ring;
R⁶ is selected from the group consisting of hydrogen, halo, $C_1$-$C_4$ alkyl, $C_2$-$C_4$ alkenyl, $C_1$-$C_4$ alkoxy, trifluoromethyl, nitro, cyano, $C_3$-$C_6$ cycloalkyl, phenyl, phenoxy, phenethyl, benzyl, benzoyl, isoxazolyl, furyl, thienyl, and methylsulfonyl;
  wherein said $C_1$-$C_4$ alkyl group may be substituted by N-morpholino, piperidine, pyrrolidine, or $NR^9R^{10}$;
  wherein said thienyl group may be substituted by halo or $C_1$-$C_4$ alkyl;
  and wherein said phenyl, benzoyl or benzyl group may be substituted with one to two substituents independently selected from the group consisting of halo, $C_1$-$C_4$ alkyl, $C_1$-$C_4$ alkoxy, $CF_3$, amino, nitro, hydroxy, methylsulfonylamino, sulfonamido, and $C(O)R^{11}$;
  wherein $R^{11}$ is selected from the group comprising N-morpholino, hydroxy or $NR^9R^{10}$;
X is —O—, —S(O)$_p$—, or —NR⁸—;
n is 2 or 3;
p is 0, 1, or 2;
R⁷ is hydrogen, methyl, ethynyl, phenyl, thienyl or pyrazole;
  wherein said phenyl, thienyl or pyrazole may be substituted by hydroxy, halo or amino;
R⁸ is hydrogen, $C_1$-$C_4$ alkyl, benzyl or tert-butyl ester;
or a pharmaceutically acceptable salt thereof.
2. A compound of claim 1, wherein:
R¹ is hydrogen, or hydroxy;
R² is hydrogen, $C_1$-$C_4$ alkyl, or $C_2$-$C_4$ alkenyl,
  wherein said $C_1$-$C_4$ alkyl is optionally substituted with carboxyl, $C_1$-$C_4$ alkoxycarbonyl, or —$NR^9R^{10}$;
  $R^9$ and $R^{10}$ are each independently hydrogen or $C_1$-$C_4$ alkyl;
R³ is hydrogen, or $C_1$-$C_4$ alkyl;
R⁴ is hydrogen, halo, $C_1$-$C_4$ alkyl, or $C_1$-$C_4$ alkoxy;

$R^5$ is hydrogen, halo, $C_1$-$C_4$ alkyl, $C_1$-$C_4$ alkoxy, trifluoromethyl, or nitro;
  or $R^4$ and $R^5$, together with the carbon atoms to which they are attached, form a benzo-fused ring;
$R^6$ is selected from the group consisting of hydrogen, halo, $C_1$-$C_4$ alkyl, $C_2$-$C_4$ alkenyl, $C_1$-$C_4$ alkoxy, trifluoromethyl, nitro, cyano, $C_3$-$C_6$ cycloalkyl, phenyl, phenoxy, phenethyl, benzyl, benzoyl, isoxazolyl, furyl, and thienyl;
  wherein said phenyl or benzyl groups is optionally substituted with one to two substituents independently selected from the group consisting of halo, $C_1$-$C_4$ alkyl, and $C_1$-$C_4$ alkoxy;
X is —O—, —S(O)$_p$—, or —NR$^8$—;
n is 2 or 3;
p is 0, 1, or 2;
$R^7$ is hydrogen or phenyl;
$R^8$ is hydrogen or $C_1$-$C_4$ alkyl;
or a pharmaceutically acceptable salt thereof.

3. The compound of claim 2 wherein $R^3$ is hydrogen.

4. The compound of claim 3 wherein n is 2.

5. The compound of claim 4 wherein $R^6$ is halo, $C_1$-$C_4$alkyl, nitro, trifluoromethyl, benzoyl, ortho-phenyl, or ortho-benzyl, which phenyl or benzyl is optionally substituted with one to two substituents independently selected from the group consisting of halo, $C_1$-$C_4$ alkyl, $C_1$-$C_4$ alkoxy, nitro and sulfonamido.

6. The compound of claim 5 wherein X is O.

7. The compound of claim 6 wherein $R^2$ is hydrogen or $C_1$-$C_4$ alkyl.

8. The compound of claim 7 wherein $R^1$ is hydrogen or hydroxy.

9. The compound of claim 8 wherein $R^1$ is hydrogen.

10. The compound of claim 9 wherein $R^7$ is phenyl or hydroxyphenyl.

11. The compound of claim 9 wherein $R^7$ is 3-hydroxyphenyl or 4-hydroxyphenyl.

12. A pharmaceutical composition comprising the compound of claim 1, or a pharmaceutically acceptable salt thereof, in combination with a pharmaceutically acceptable carrier, excipient, or diluent.

* * * * *